US011754557B2

(12) United States Patent
Lee et al.

(10) Patent No.: US 11,754,557 B2
(45) Date of Patent: Sep. 12, 2023

(54) METHOD AND APPARATUS FOR ANALYSIS OF PROTEIN-PROTEIN INTERACTION

(71) Applicant: Proteina Co., Ltd., Seoul (KR)

(72) Inventors: Hong Won Lee, Seoul (KR); Youjin Na, Seongnam-si (KR)

(73) Assignee: PROTEINA, INC., Daejeon (KR)

(*) Notice: Subject to any disclaimer, the term of this patent is extended or adjusted under 35 U.S.C. 154(b) by 674 days.

(21) Appl. No.: 16/496,381

(22) PCT Filed: Apr. 19, 2018

(86) PCT No.: PCT/KR2018/004580
§ 371 (c)(1),
(2) Date: Sep. 20, 2019

(87) PCT Pub. No.: WO2018/194406
PCT Pub. Date: Oct. 25, 2018

(65) Prior Publication Data
US 2020/0386747 A1 Dec. 10, 2020

(30) Foreign Application Priority Data

Apr. 19, 2017 (KR) ........................ 10-2017-0050681
Mar. 26, 2018 (KR) ........................ 10-2018-0034749

(51) Int. Cl.
| G01N 33/543 | (2006.01) |
| G01N 21/64 | (2006.01) |
| G01N 33/50 | (2006.01) |
| G01N 33/58 | (2006.01) |
| G01N 33/68 | (2006.01) |

(52) U.S. Cl.
CPC ... G01N 33/54306 (2013.01); G01N 21/6428 (2013.01); G01N 33/5011 (2013.01); G01N 33/582 (2013.01); G01N 33/6845 (2013.01); G01N 2021/6439 (2013.01); G01N 2333/4703 (2013.01); G01N 2333/71 (2013.01); G01N 2500/20 (2013.01)

(58) Field of Classification Search
CPC ........ G01N 33/54306; G01N 21/6428; G01N 33/5011; G01N 33/582; G01N 2333/4703; G01N 2333/71; G01N 2500/20
See application file for complete search history.

(56) References Cited

U.S. PATENT DOCUMENTS

| 7,659,368 B2 | 2/2010 | Fitzpatrick et al. |
| 7,666,606 B2 | 2/2010 | Waldo et al. |
| 9,377,462 B2* | 6/2016 | Yoon ..................... G01N 33/574 |
| 2005/0182242 A1* | 8/2005 | Snyder ................. C07K 1/1077 |
| | | 435/7.1 |
| 2007/0282095 A1* | 12/2007 | Hosokawa .............. A61P 43/00 |
| | | 530/381 |
| 2014/0113307 A1 | 4/2014 | Yoon |

FOREIGN PATENT DOCUMENTS

| EP | 2700947 | 2/2014 |
| EP | 3153587 | 4/2017 |
| JP | 2002-253240 | 9/2002 |
| JP | 2004-503249 | 2/2004 |
| JP | 3942431 | 7/2007 |
| JP | 2014-512537 | 5/2014 |
| KR | 10-2012-0120093 | 11/2012 |
| KR | 10-2014-0113543 | 9/2014 |
| KR | 10-2015-0064205 | 6/2015 |
| KR | 10-2018-0135878 | 12/2018 |
| WO | 2015-186870 | 12/2015 |
| WO | 2018/194406 | 10/2018 |

OTHER PUBLICATIONS

Lanzerstorfer (PLosOne 2014 9: e92151) (Year: 2014).*
JP 2002-253240 English Machine Translation (Year: 2002).*
JP Japanese original patent JP 2002-253240 (Year: 2002).*
EPO, Extended Search Report of EP 18787363.3 dated Nov. 30, 2020.
Hong-Won Lee et al, "Real-time single-molecule co-immunoprecipitation analyses reveal cancer-specific Ras signalling dynamics", Nature Communications, Feb. 19, 2013.
Yosef Yarden et al., "Untangling the ErbB signalling network", Nature Reviews, Molecular Cell Biology. vol. 2, pp. 127-137 Feb. 2001.
Mark A. Lemmon et al., "Cell signaling by receptor tyrosine kinases", Cell 141, pp. 1117-1134, Jun. 2010.
Lee, H. W. et al. "Real-time single-molecule coimmunoprecipitation of weak protein-protein interactions", Nature protocols vol. 8 No. 10, 2045-2060, Sep. 2013.
Fredriksson, S. et al. "Protein detection using proximity-dependent DNA ligation assays", Nature Biotechnology vol. 20, pp. 473-477, May 2002.
GenBank, "*Homo sapiens* C-C motif chemokine receptor 2 (CCR2), transcript variant A, mRNA" Database accession No. NM_001123041.2 (May 24, 2020) pp. 1-4.

* cited by examiner

Primary Examiner — Changhwa J Cheu
(74) Attorney, Agent, or Firm — LEX IP MEISTER, PLLC

(57) ABSTRACT

Disclosed are a method for analyzing an activation state of a signaling pathway in a cell or tissue through protein-protein interaction analysis, a method for selecting a tailored personal therapeutic agent and/or monitoring efficacy of a therapeutic agent using the analysis method, and a device for use therein.

9 Claims, 42 Drawing Sheets

[FIG. 1]
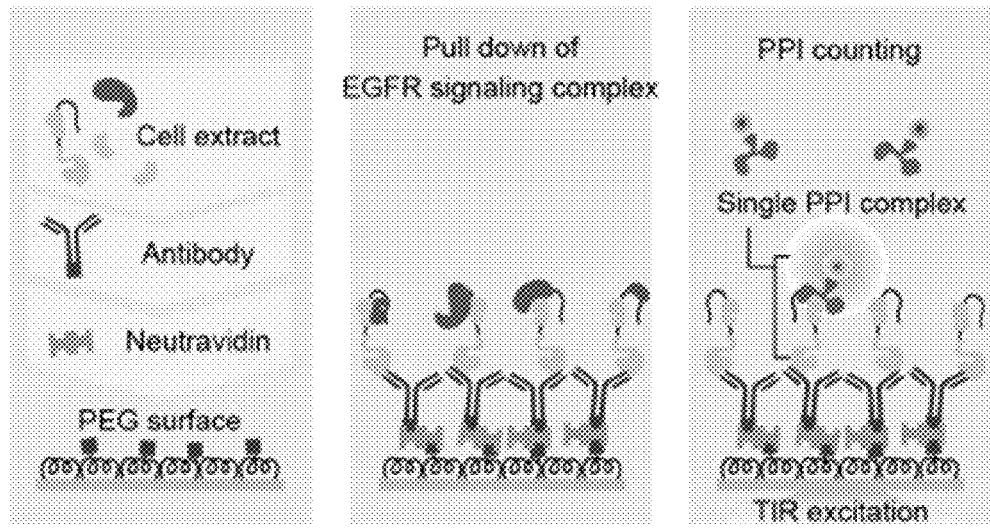
[FIG. 2]
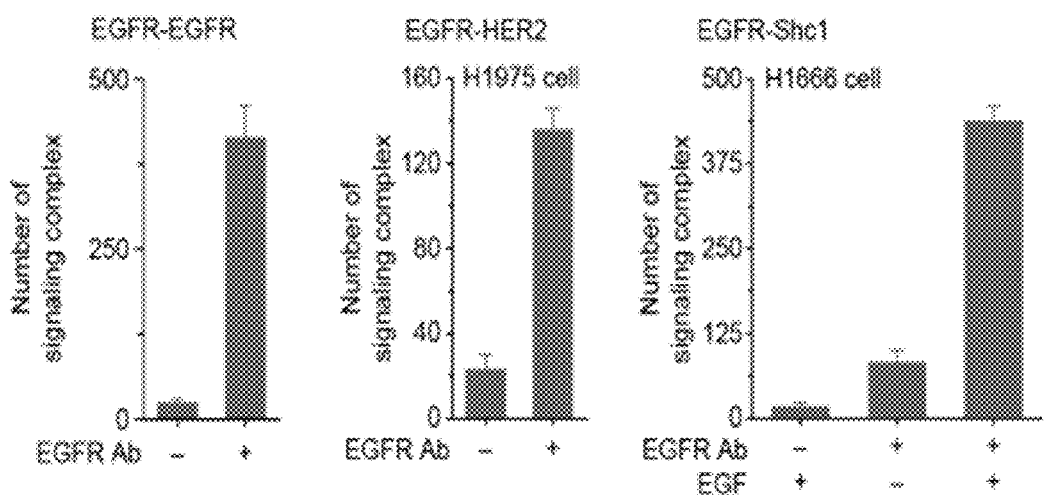

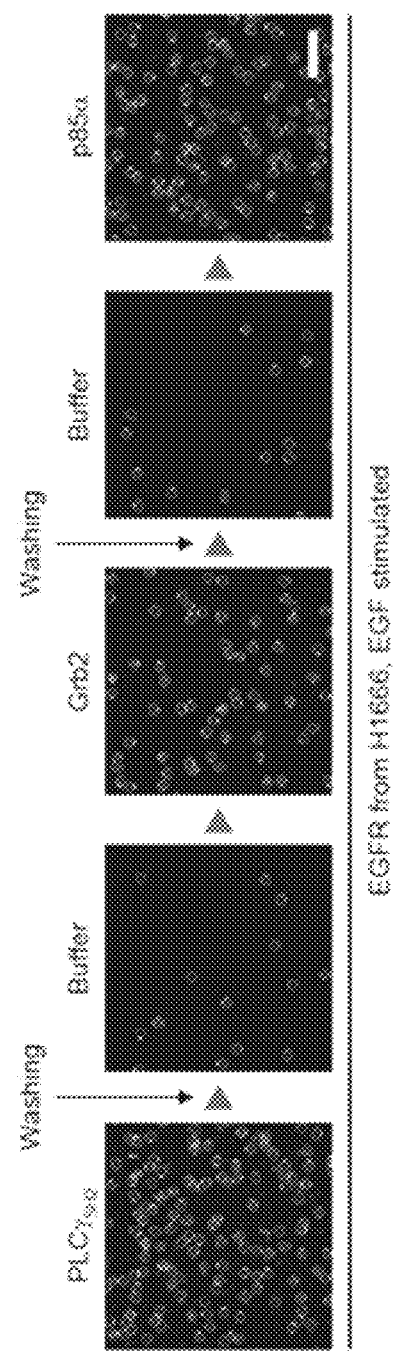
[FIG. 3]

[FIG. 4]
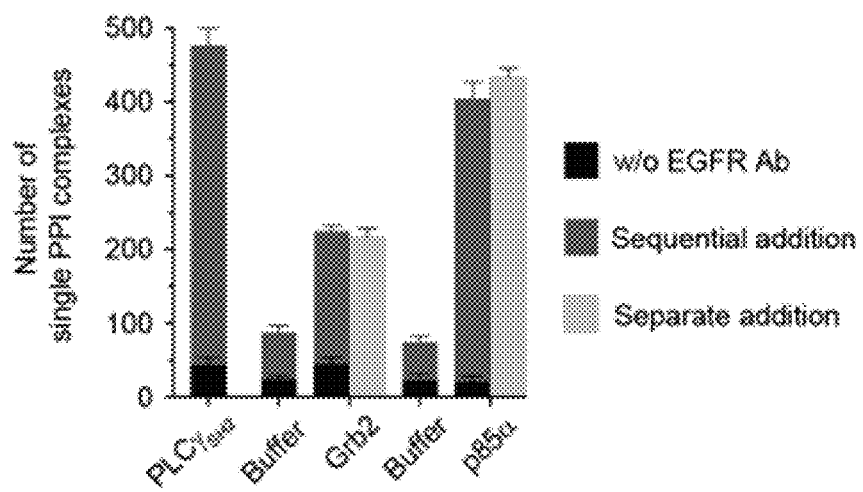
[FIG. 5]
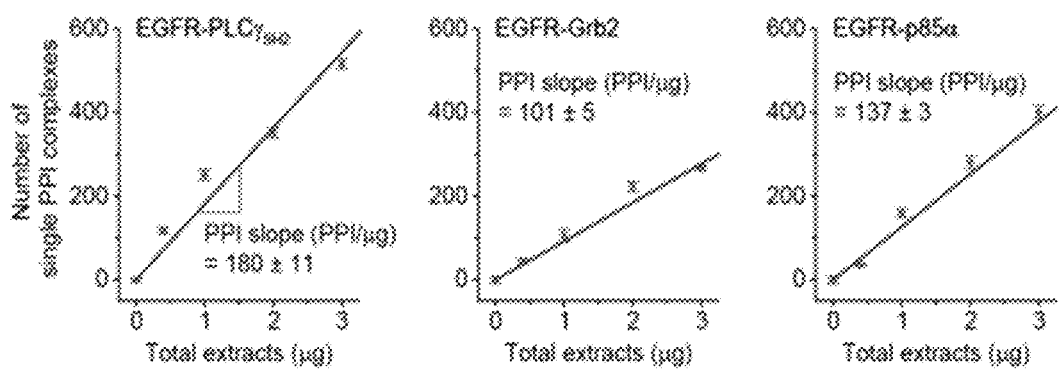

[FIG. 6]
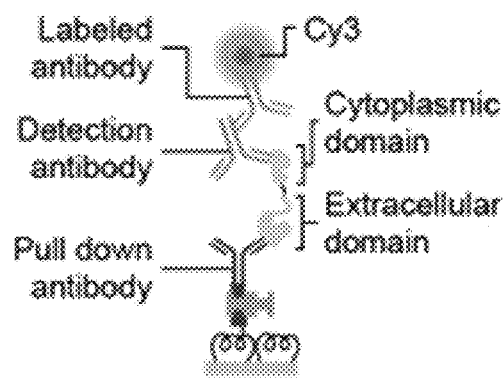
[FIG. 7]
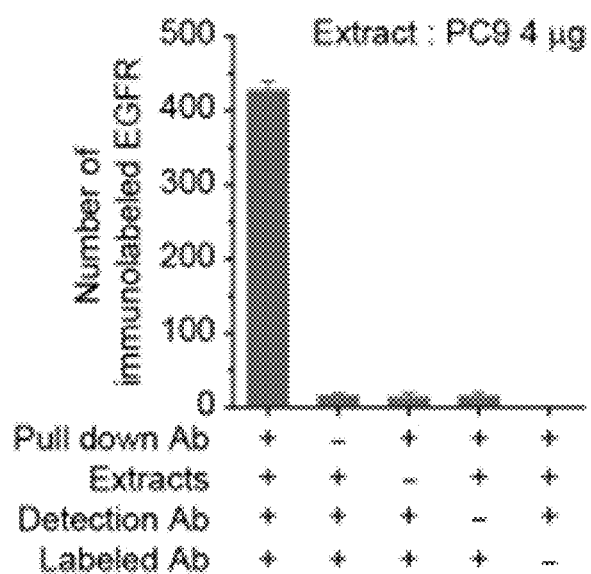

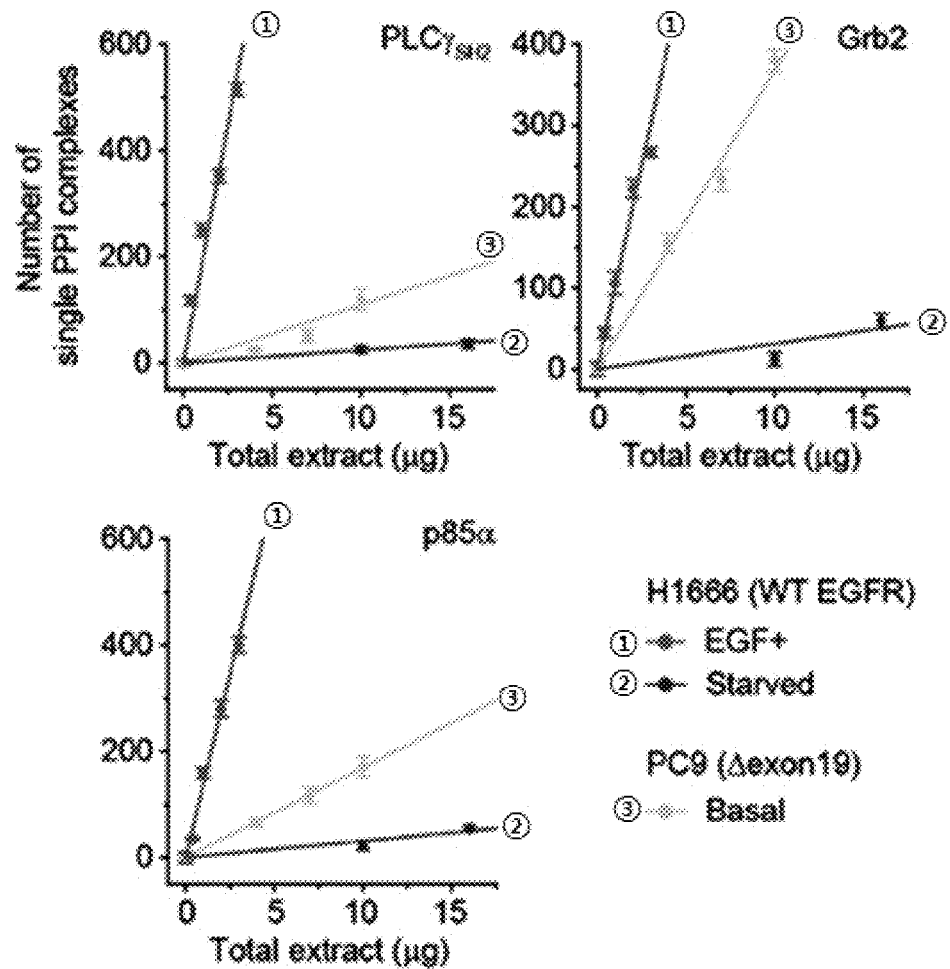
[FIG. 8]

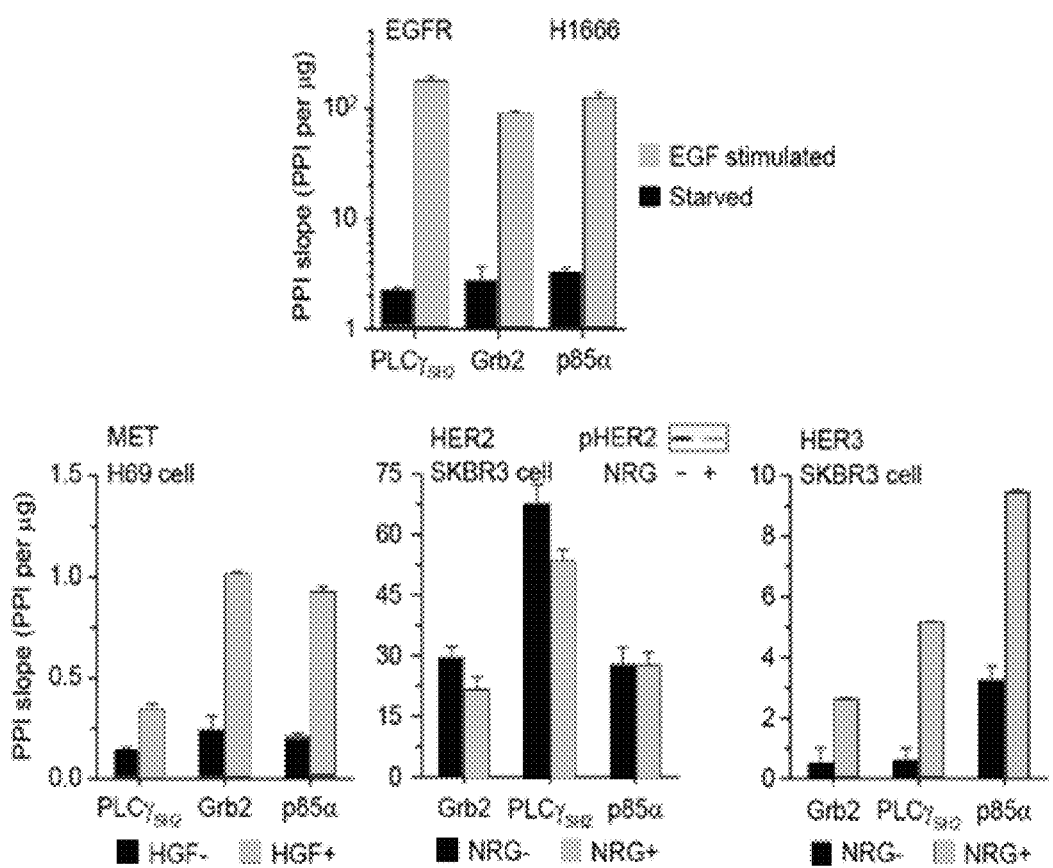
[FIG. 9]

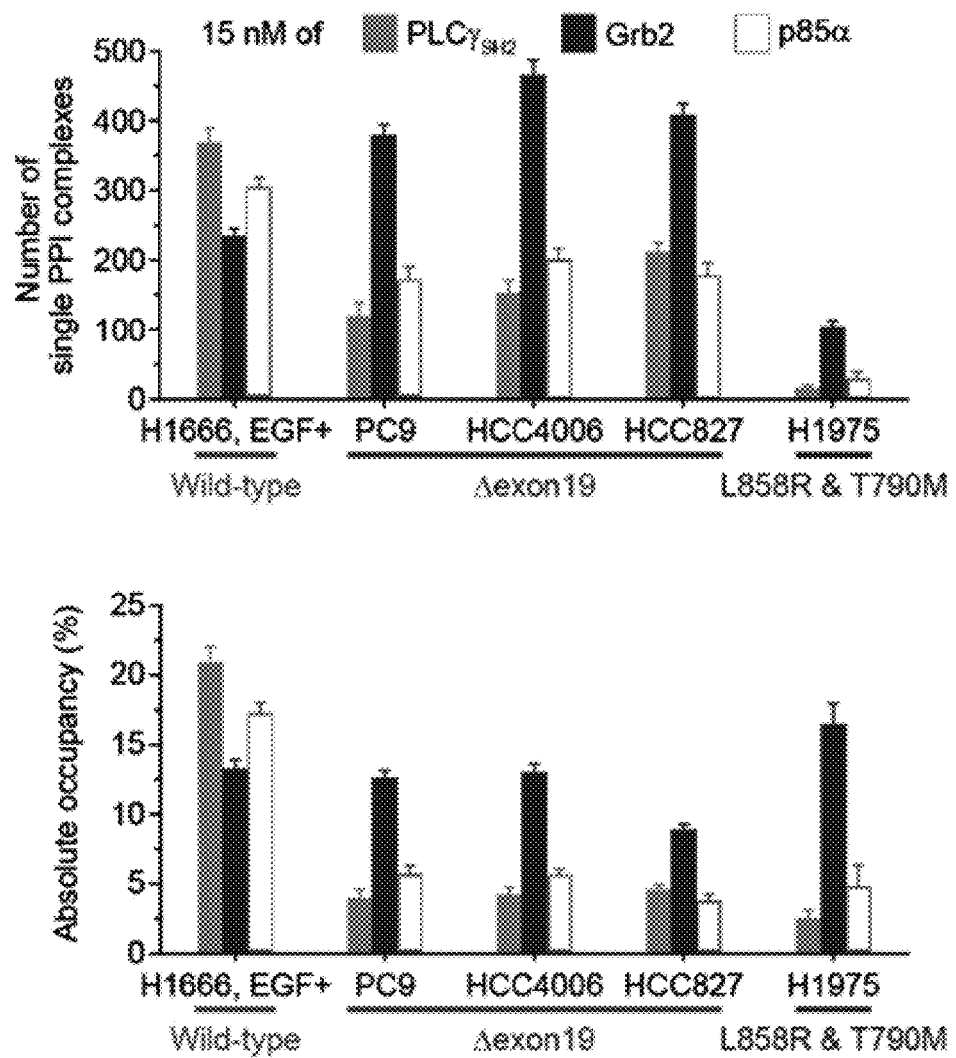
[FIG. 10]

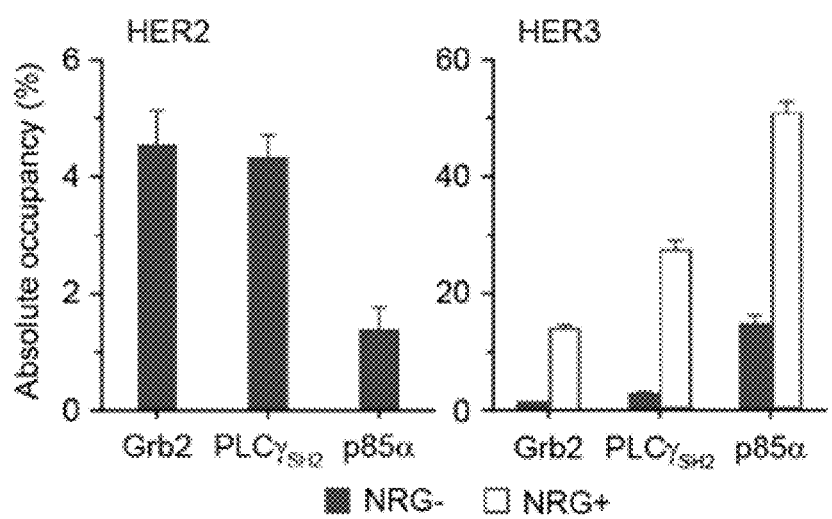
[FIG. 11]

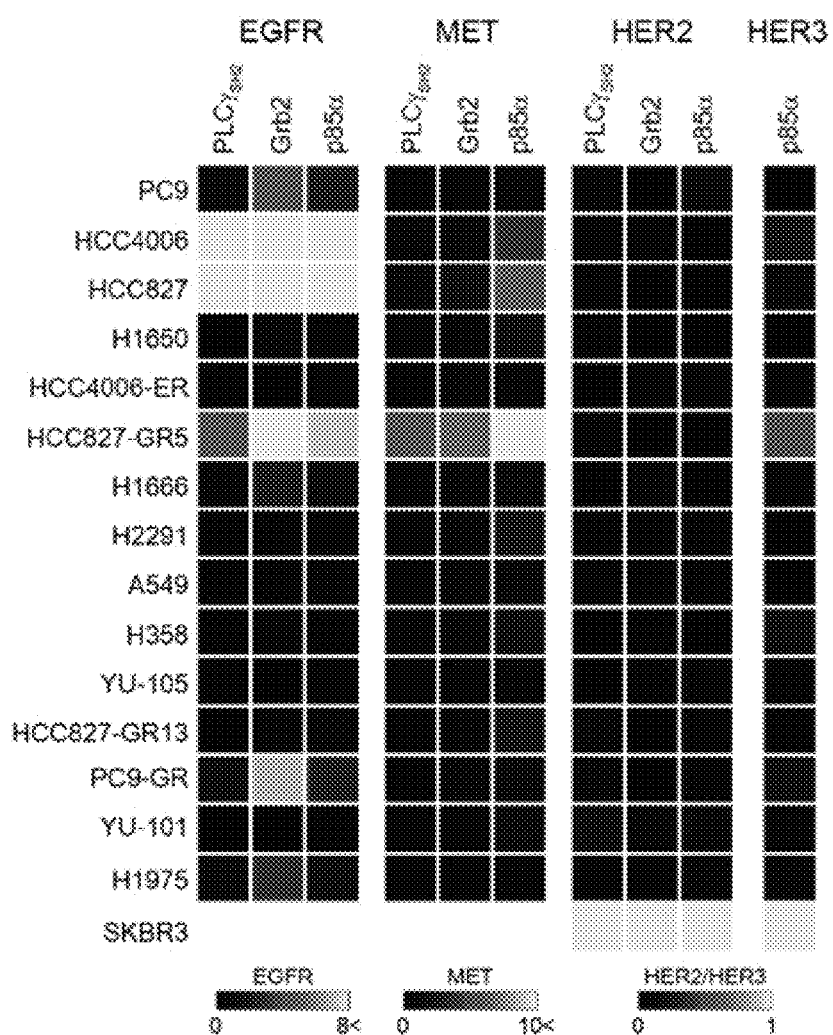

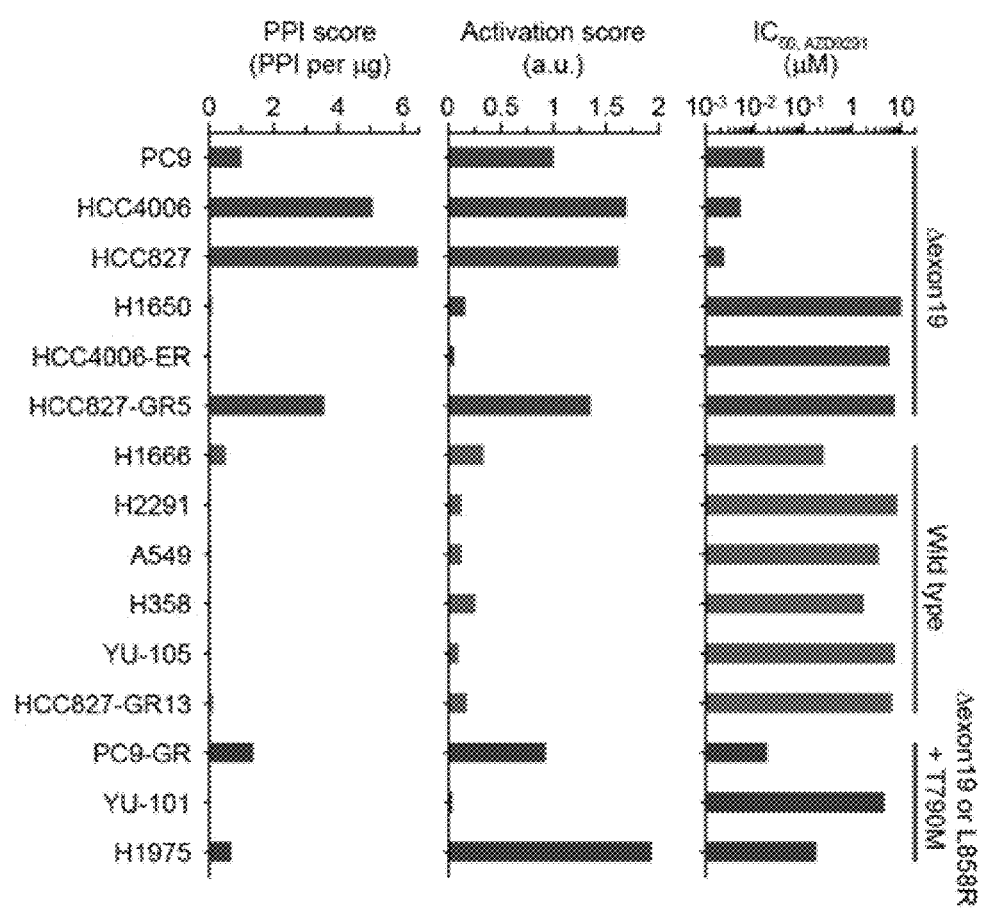
[FIG. 13]

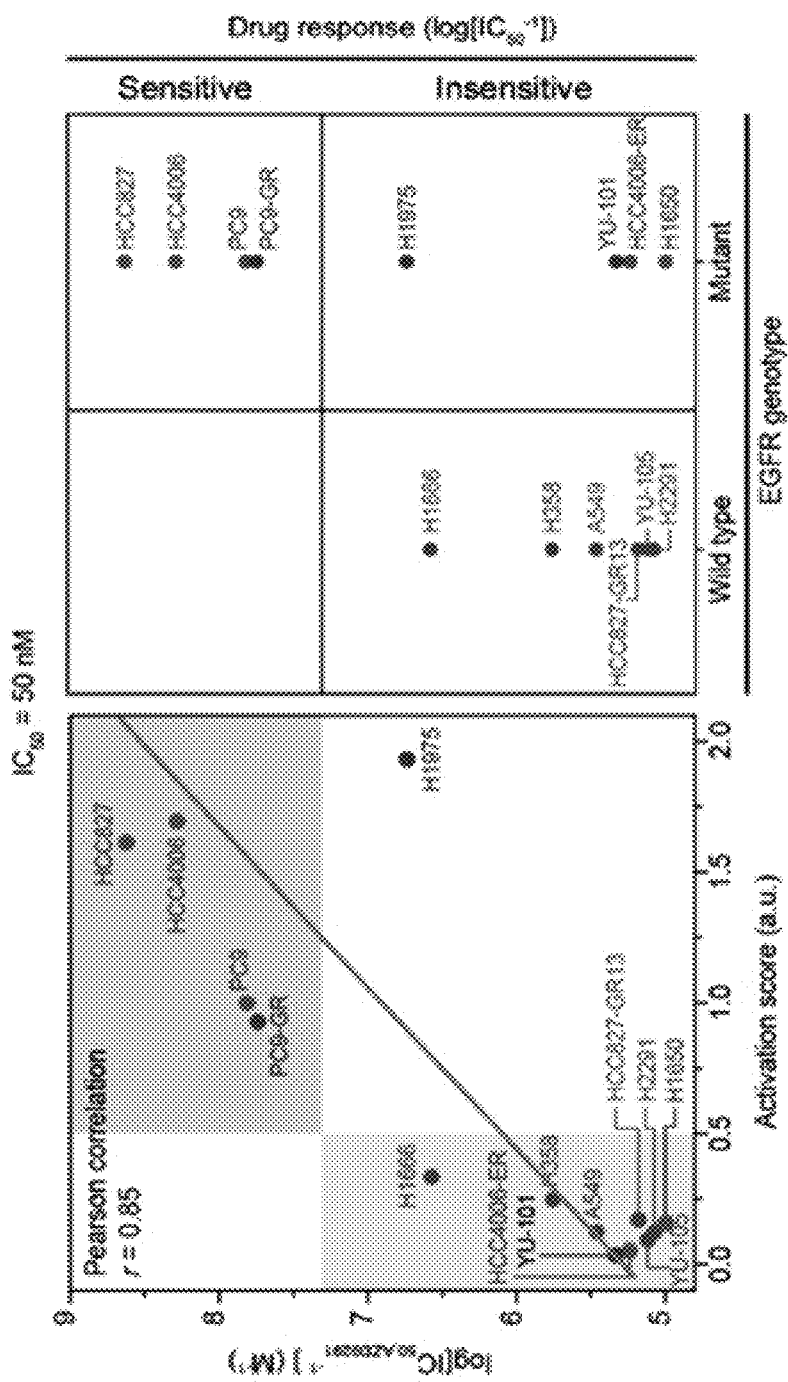
[FIG. 14]

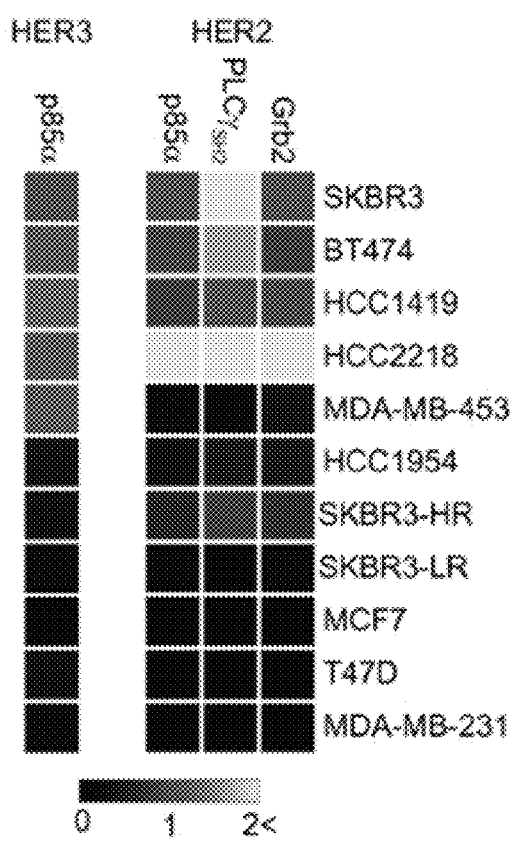
[FIG. 15]

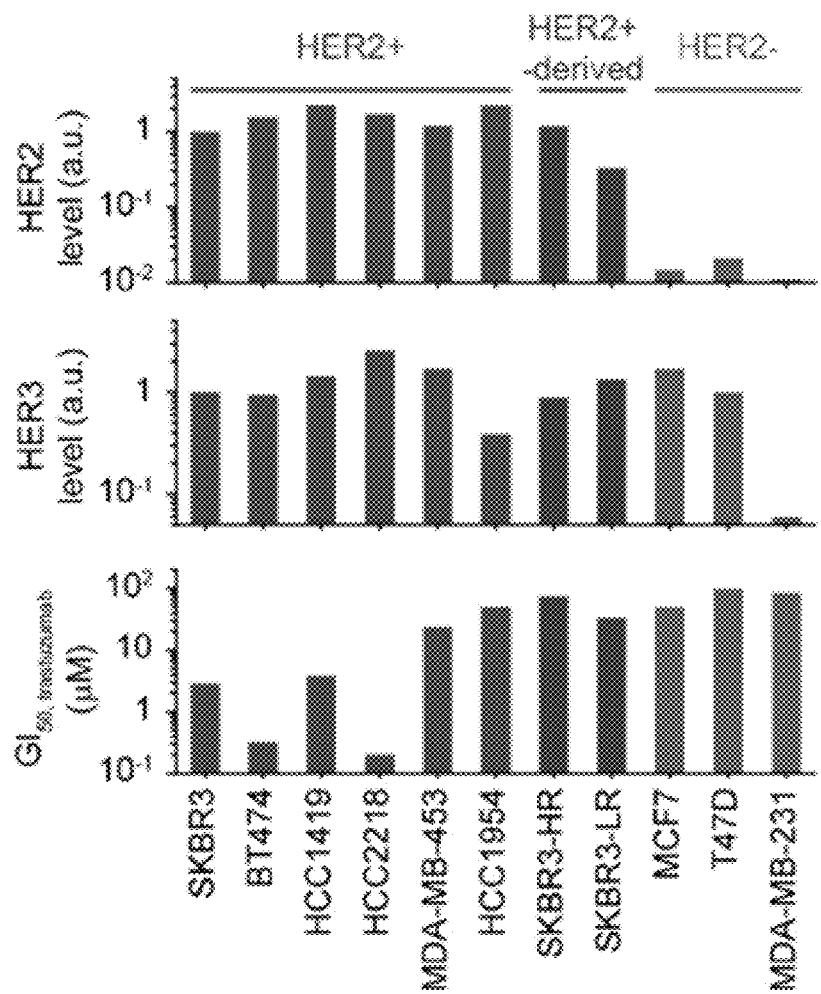
[FIG. 16]

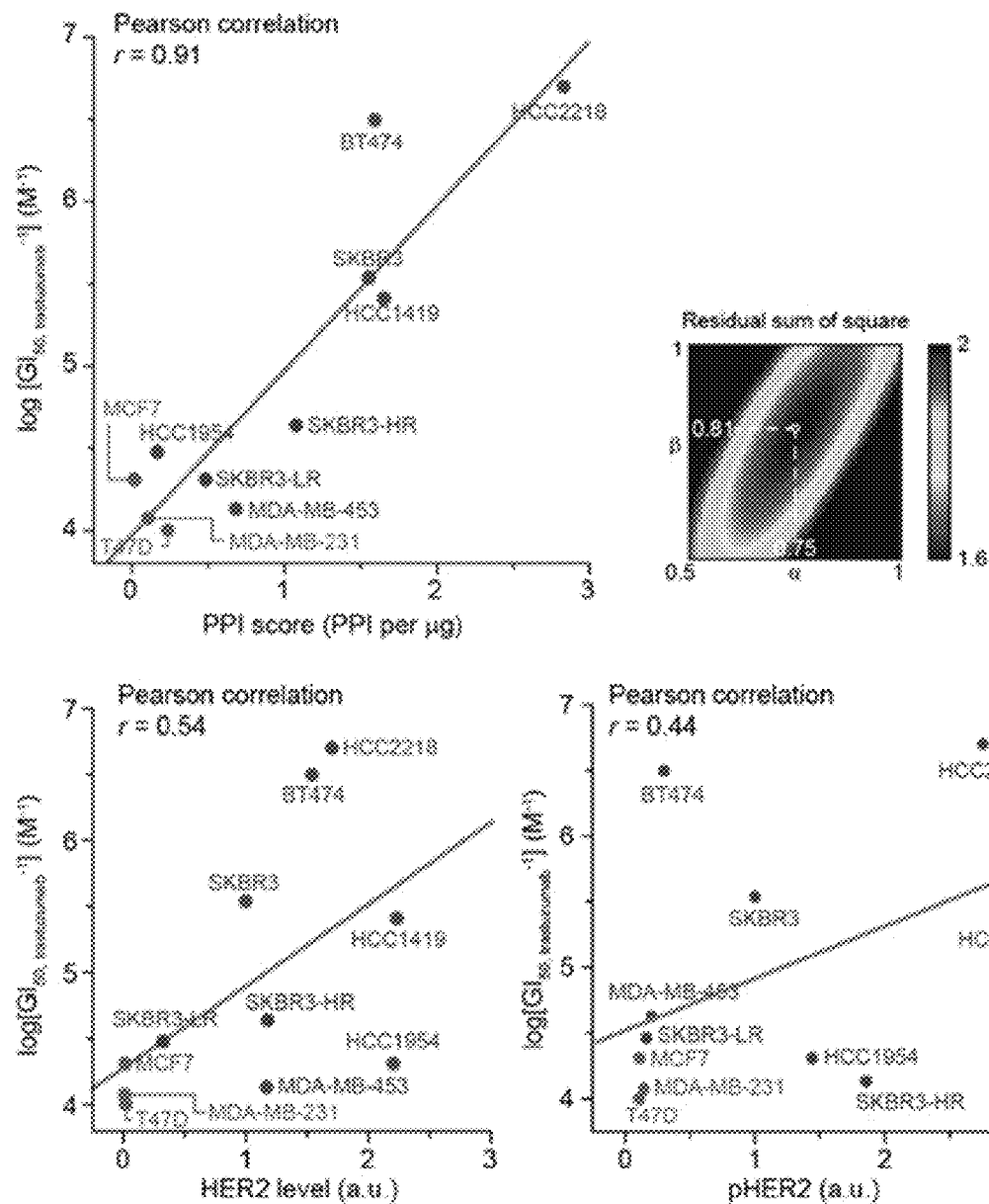
[FIG. 17]

[FIG. 18]
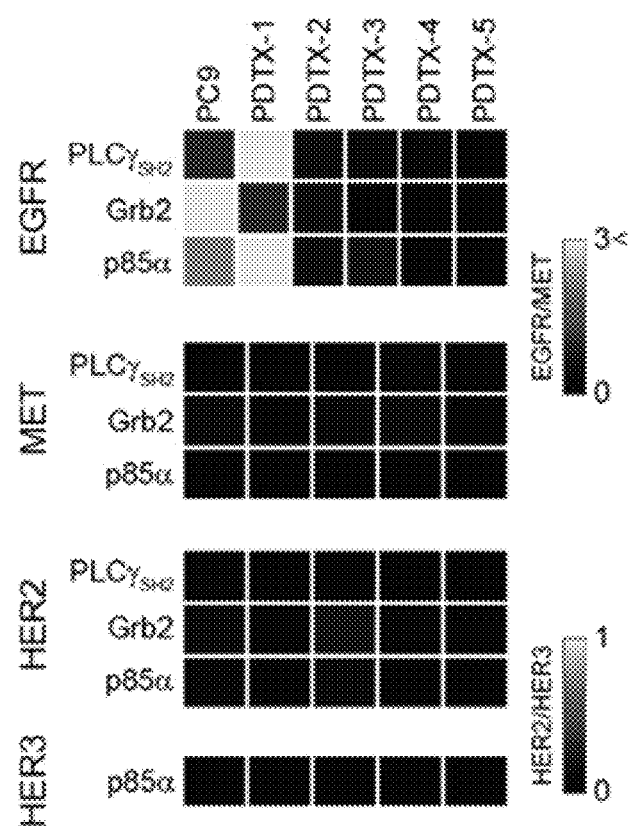

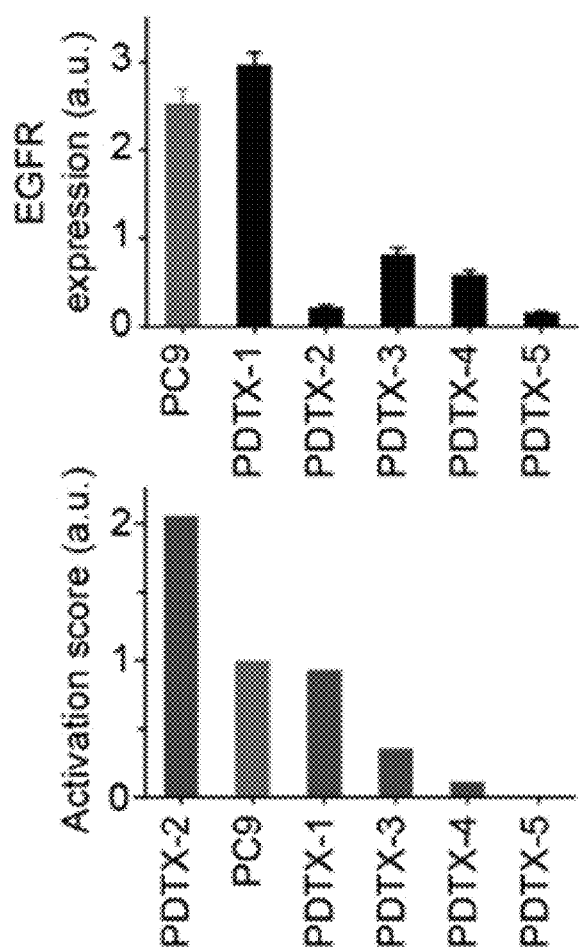
[FIG. 19]

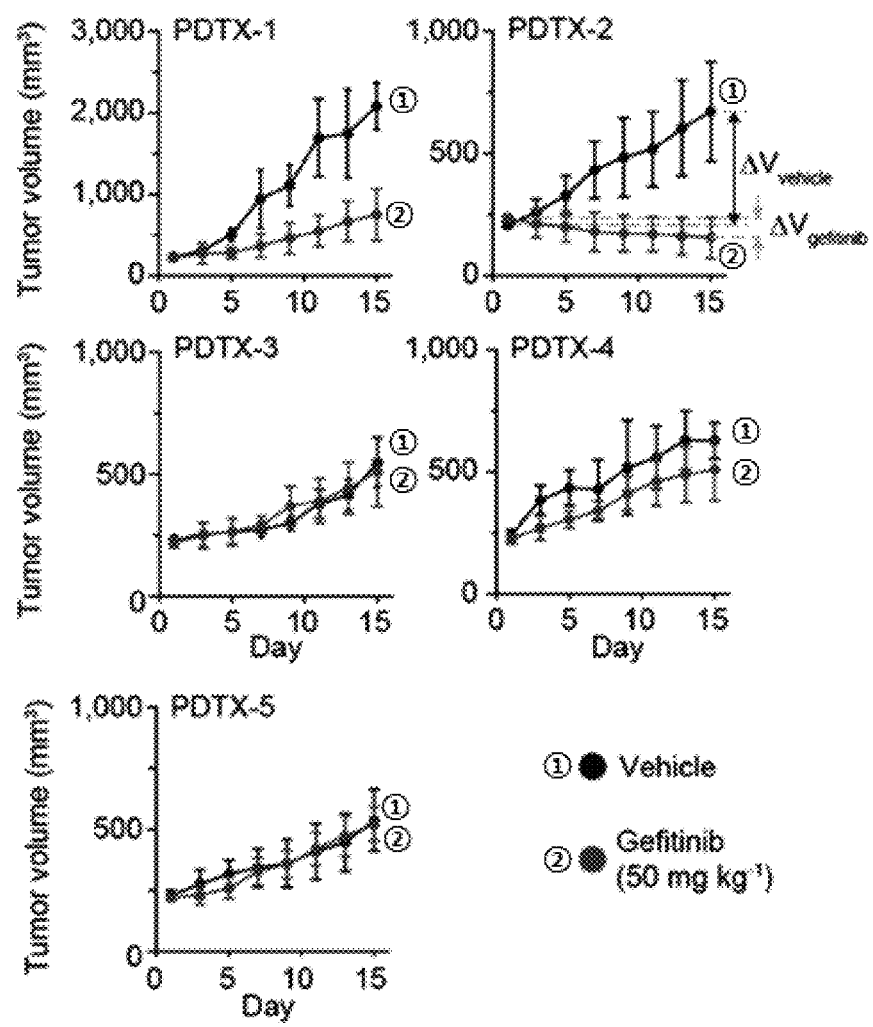
[FIG. 20]

[FIG. 21]
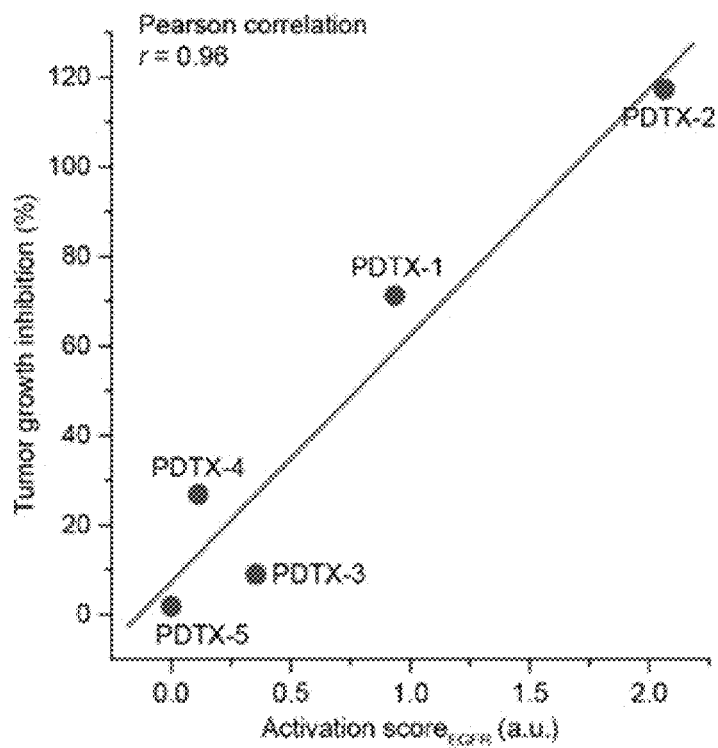
[FIG. 22]
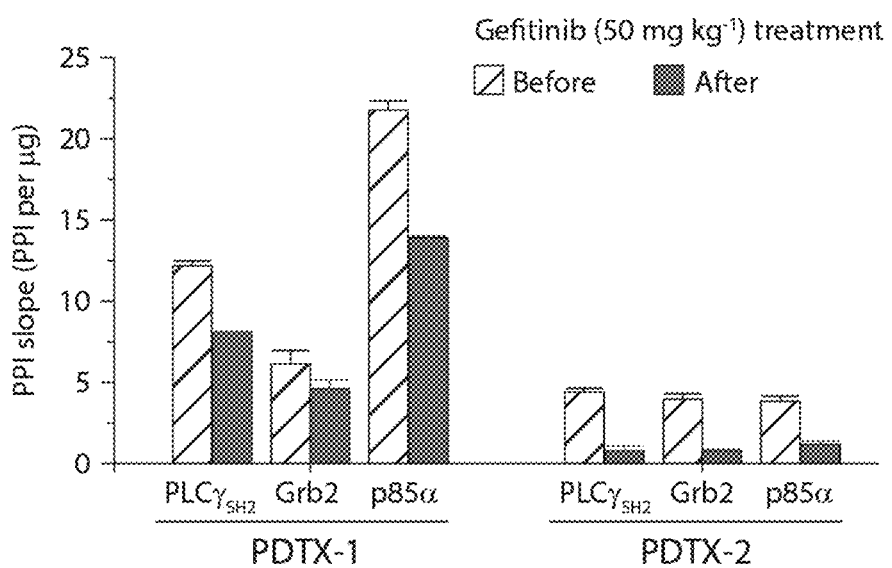

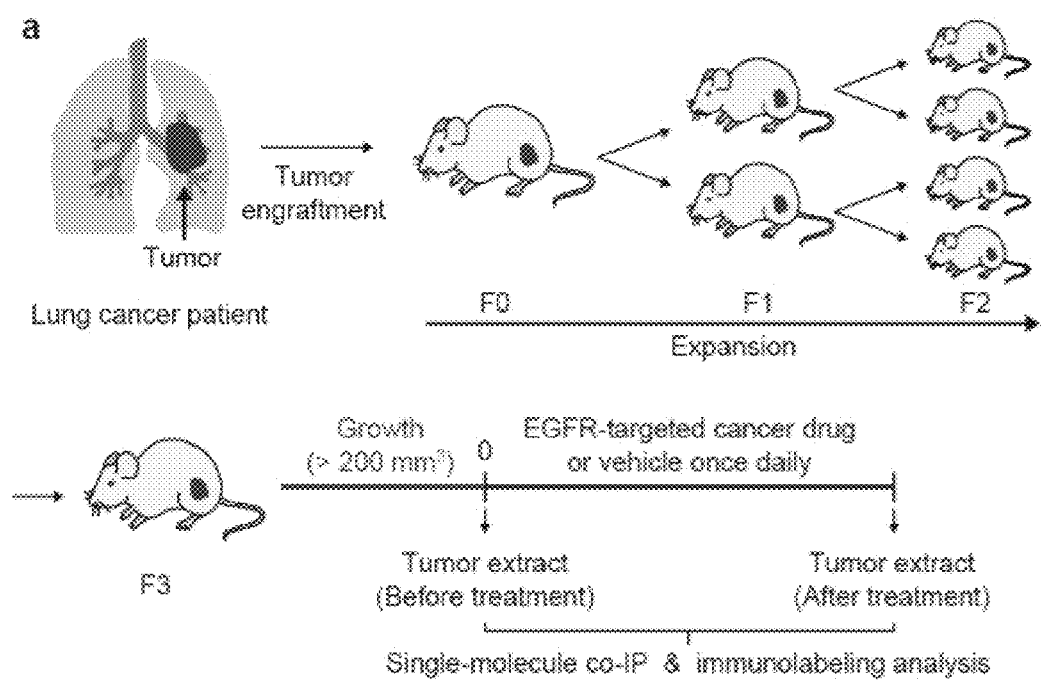
[FIG. 23a]

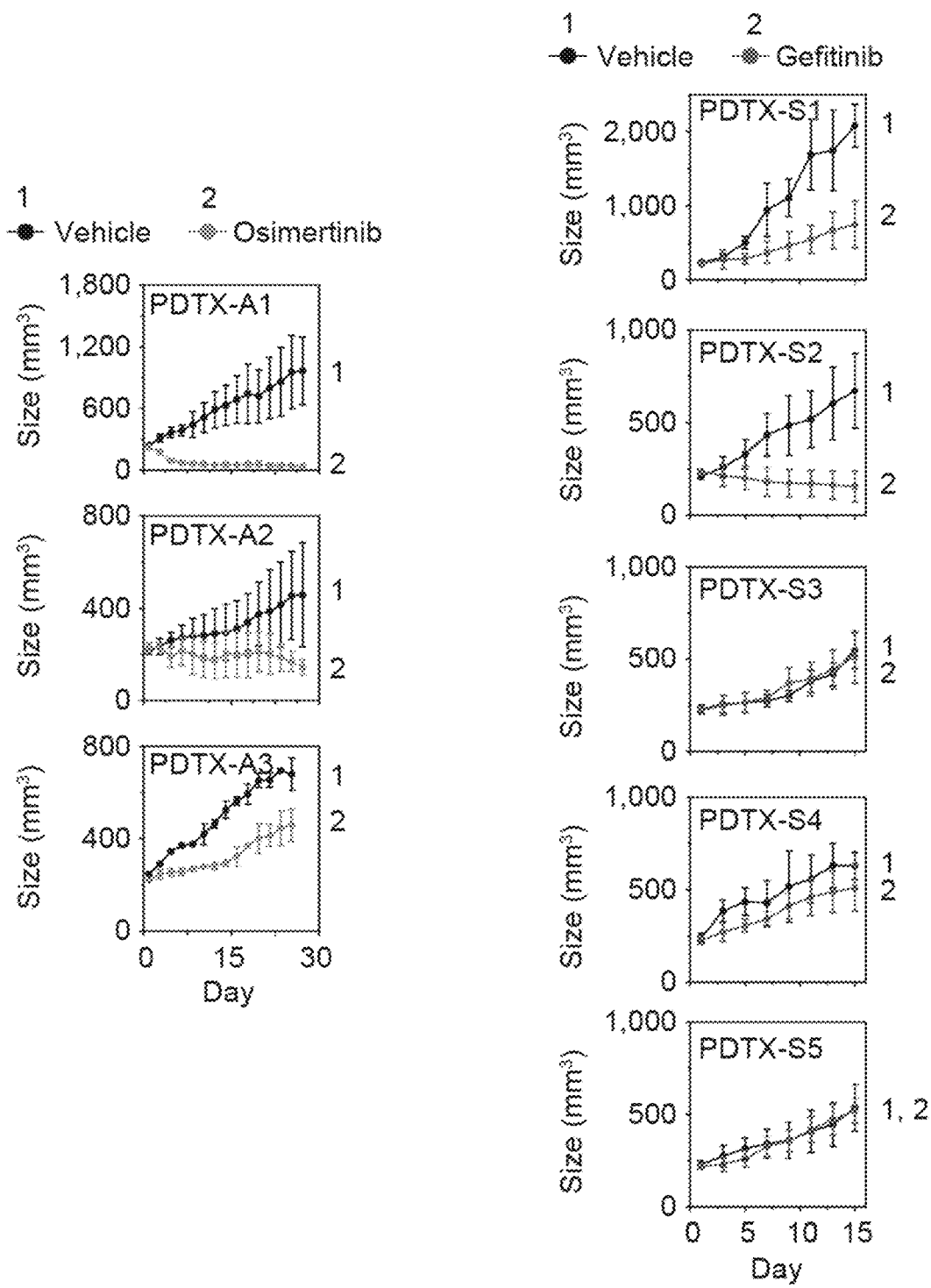
[FIG. 23b]

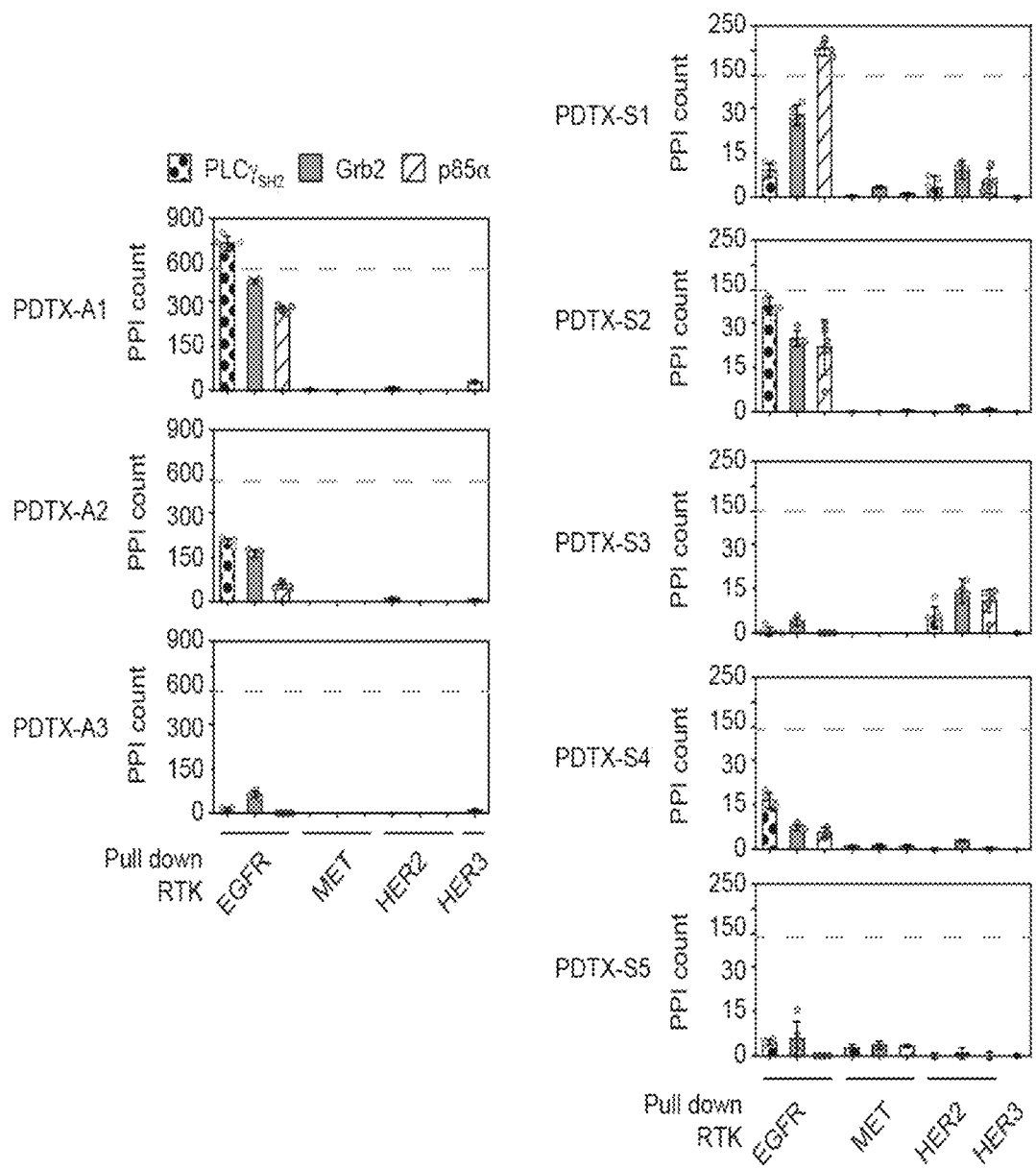
[FIG. 23c]

[FIG. 23d]
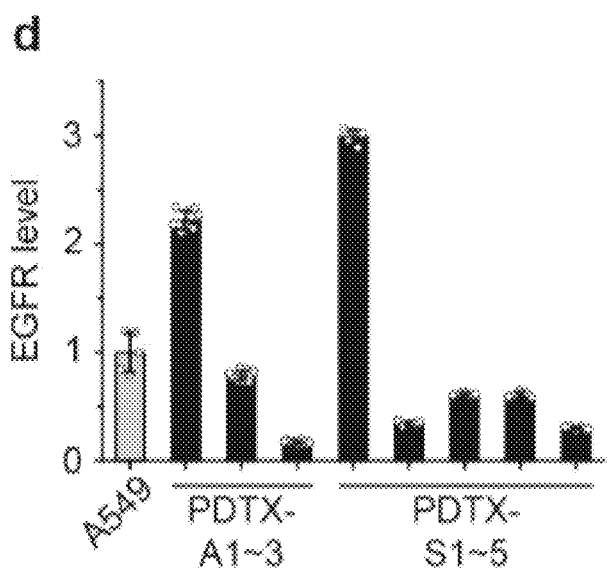
[FIG. 23e]
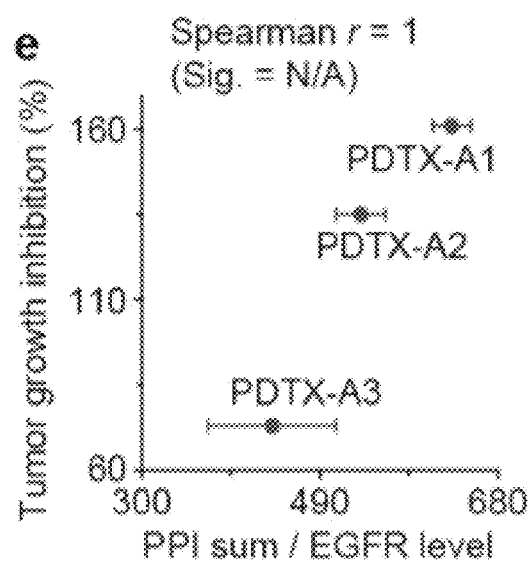

[FIG. 23f]
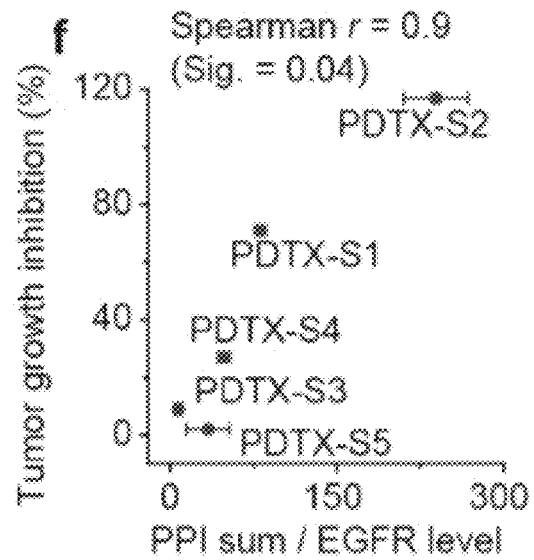
[FIG. 23g]
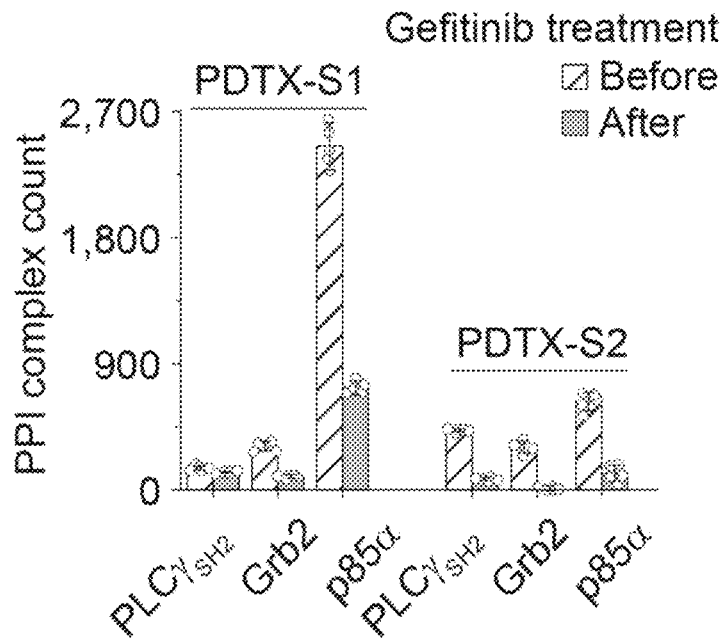

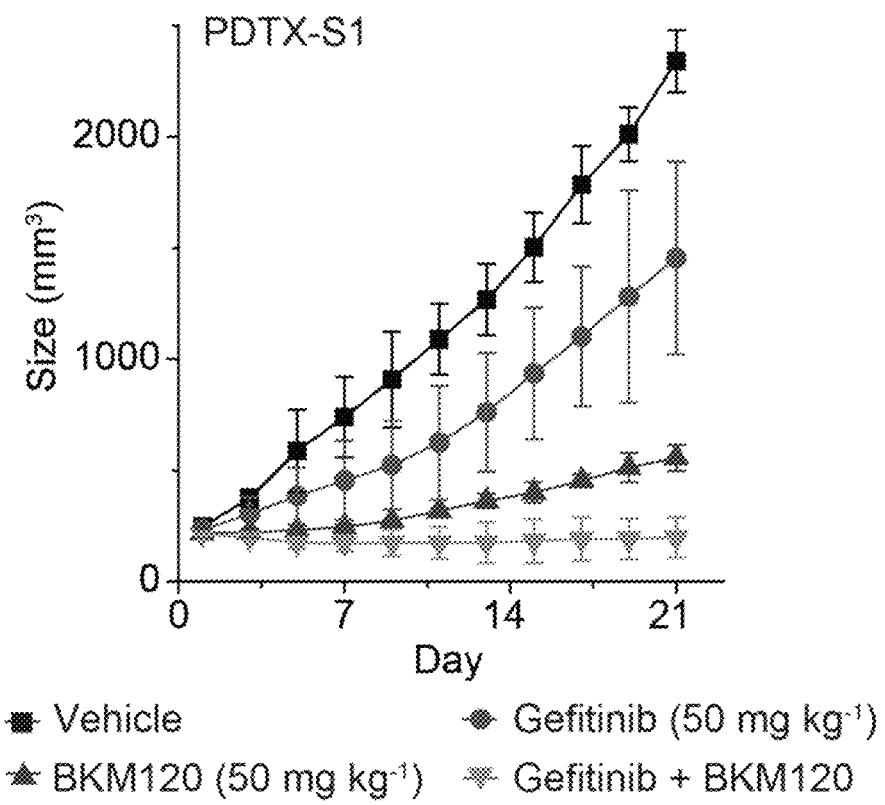

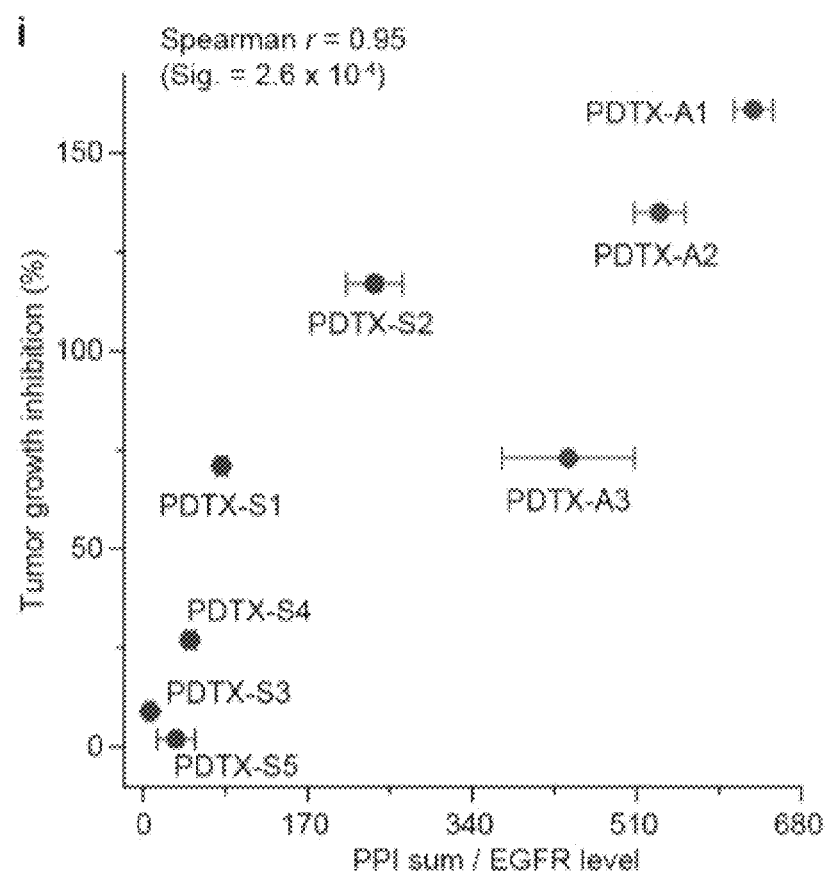
[FIG. 23i]

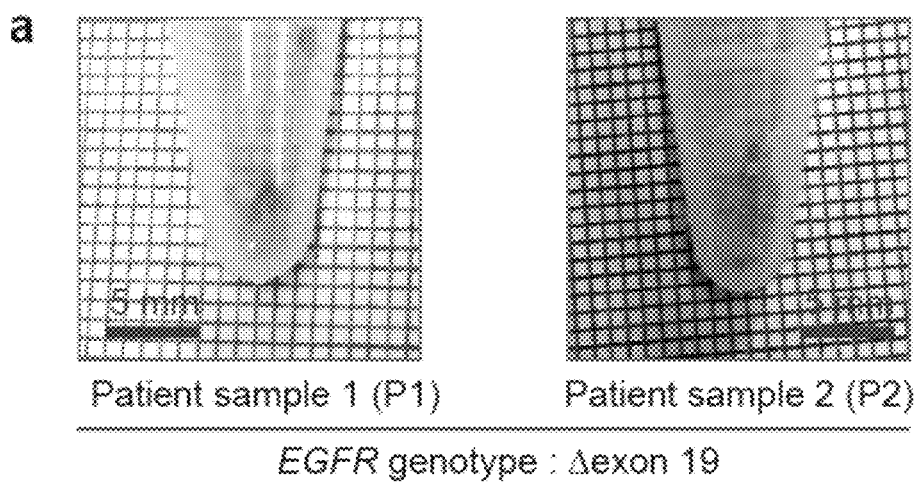
[FIG. 24a]

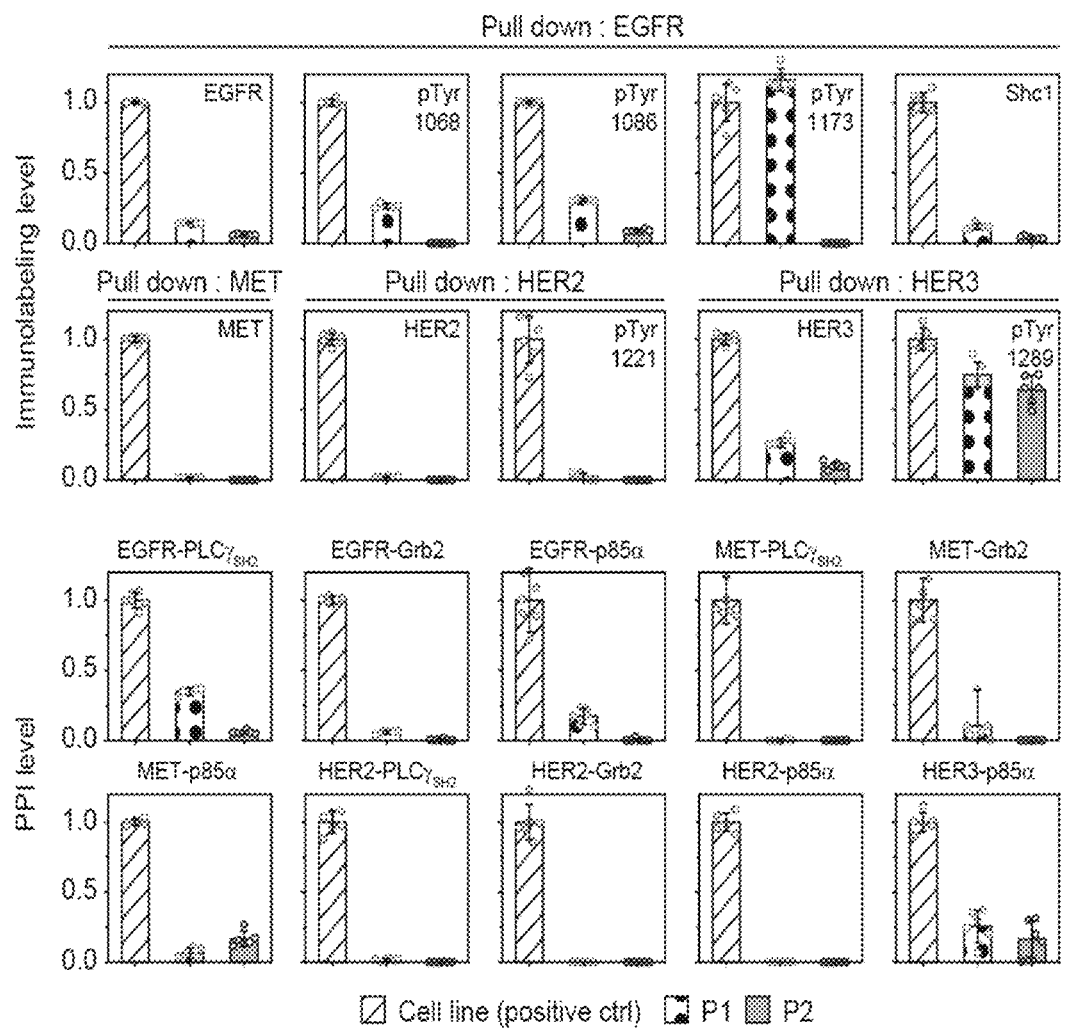
[FIG. 24b]

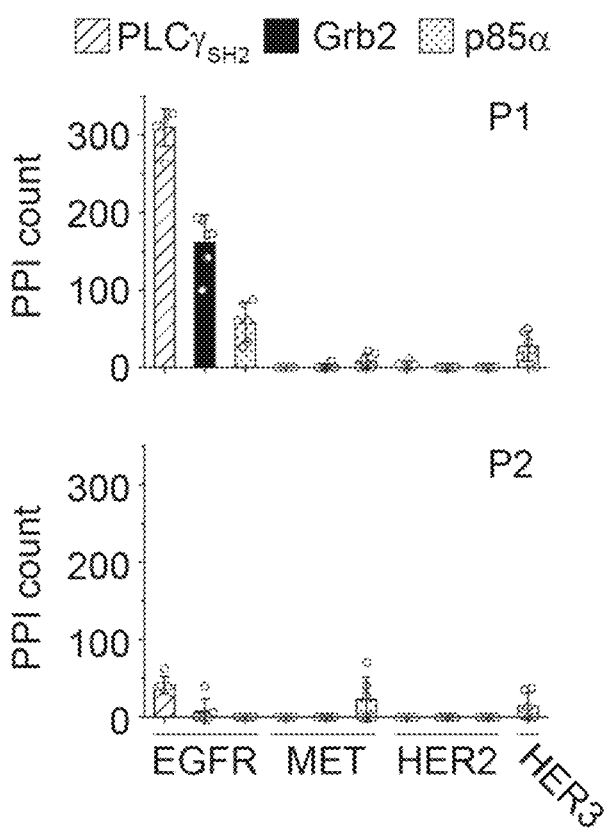
[FIG. 24c]

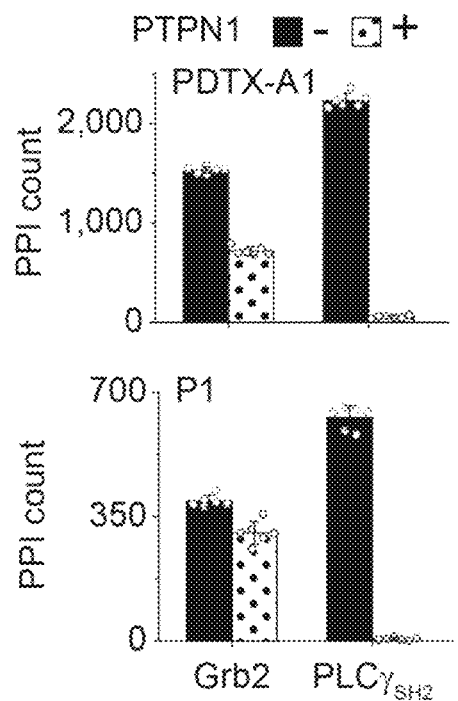
[FIG. 24d]
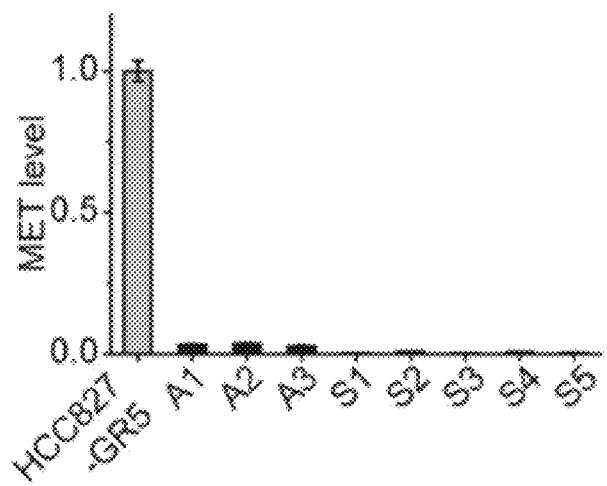
[FIG. 25a]

[FIG. 25b]
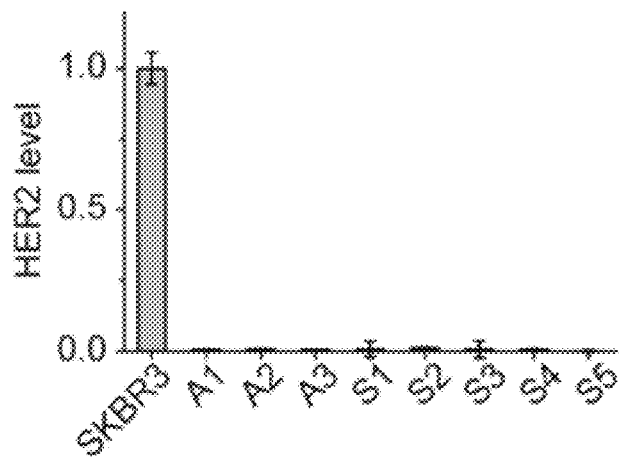
[FIG. 25c]
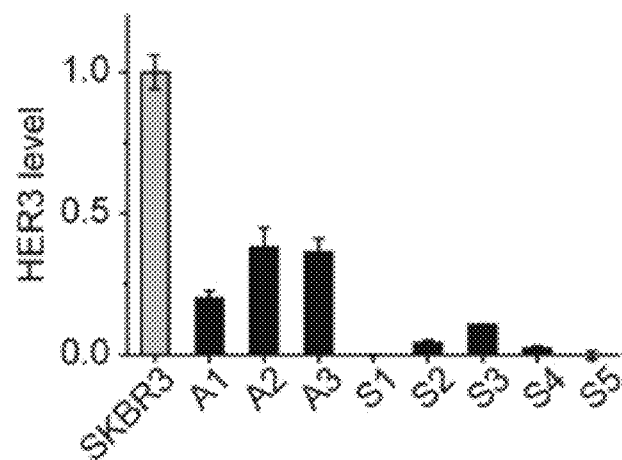

[FIG. 25d]
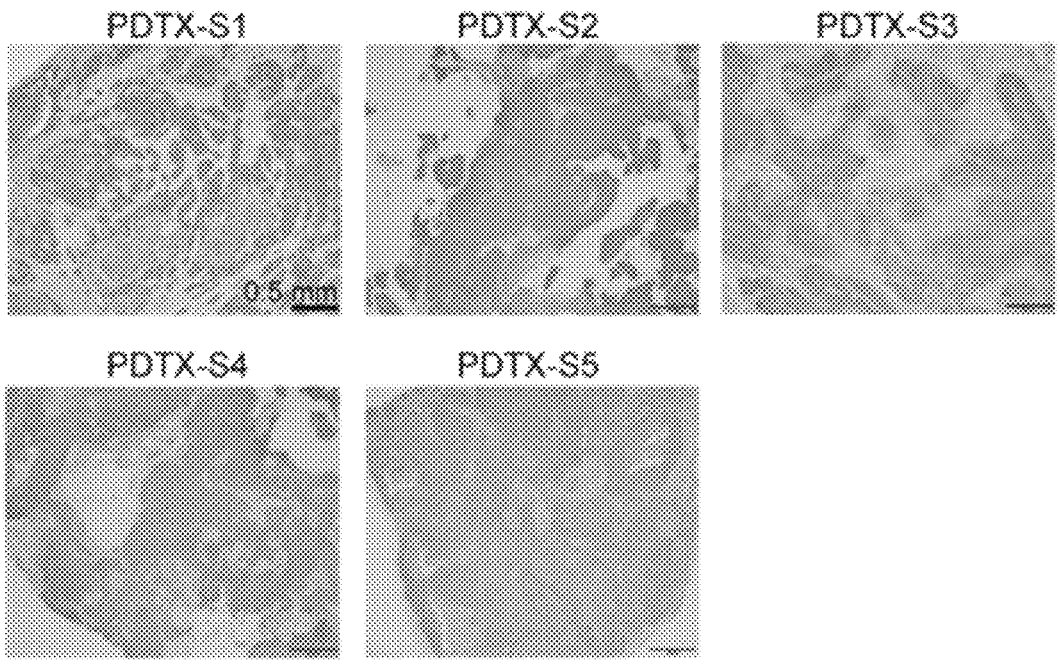
[FIG. 25e]
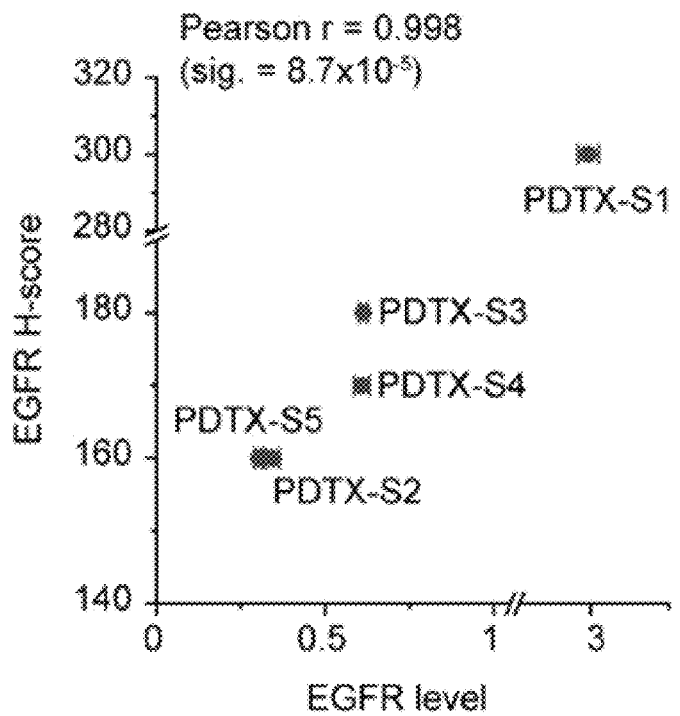

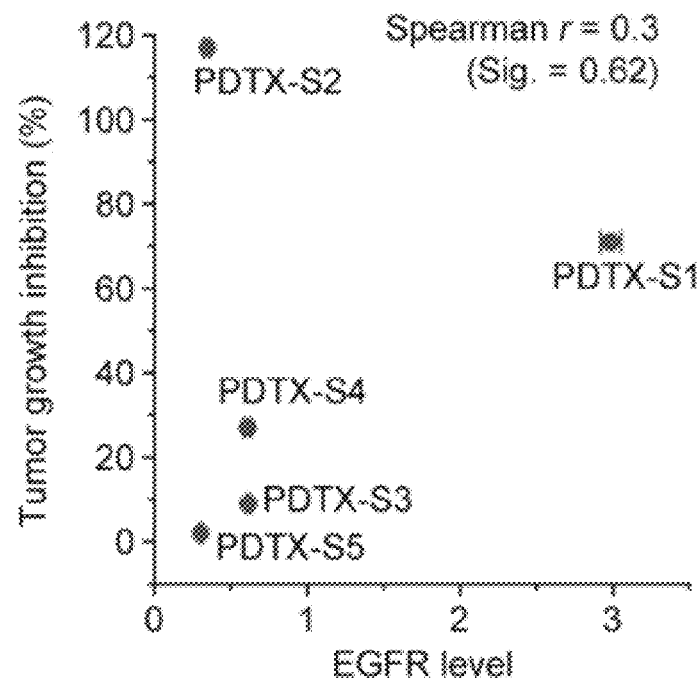
[FIG. 25f]
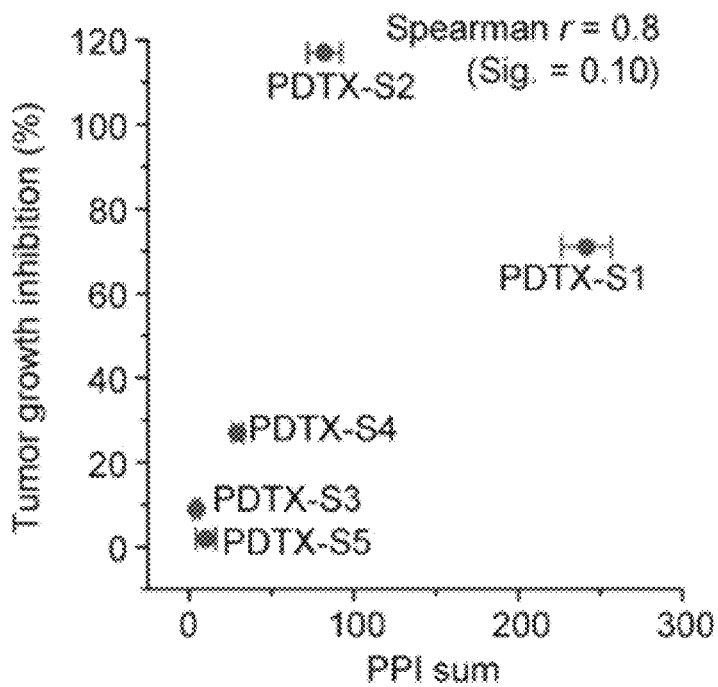
[FIG. 25g]

[FIG. 25h]
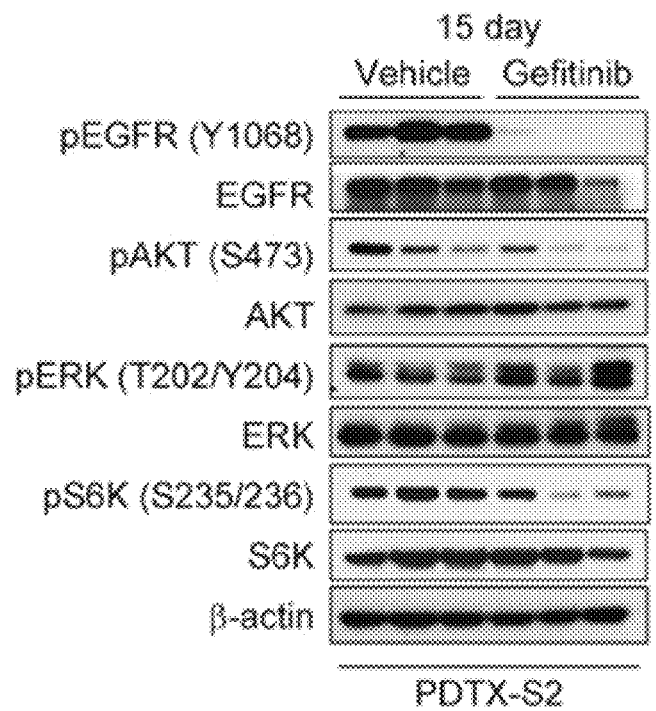
[FIG. 26a]
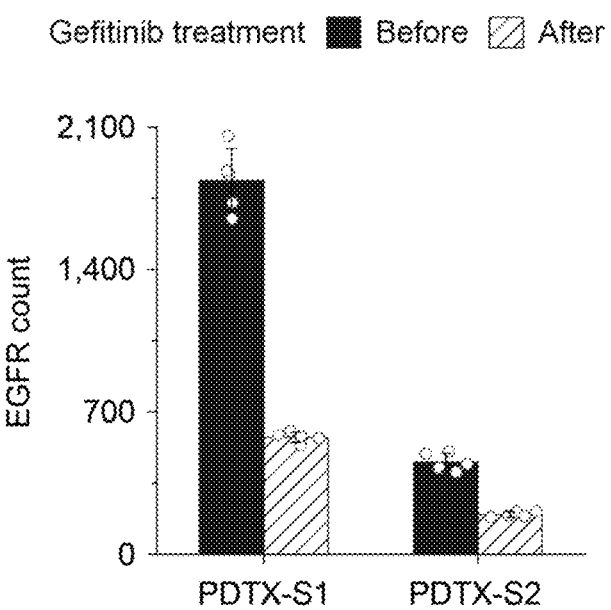

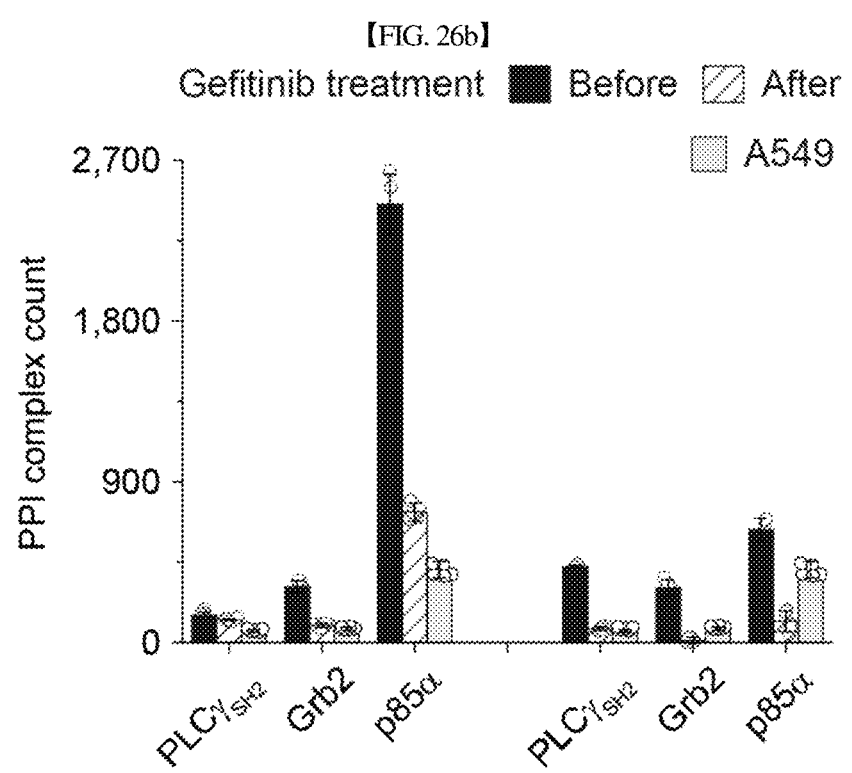

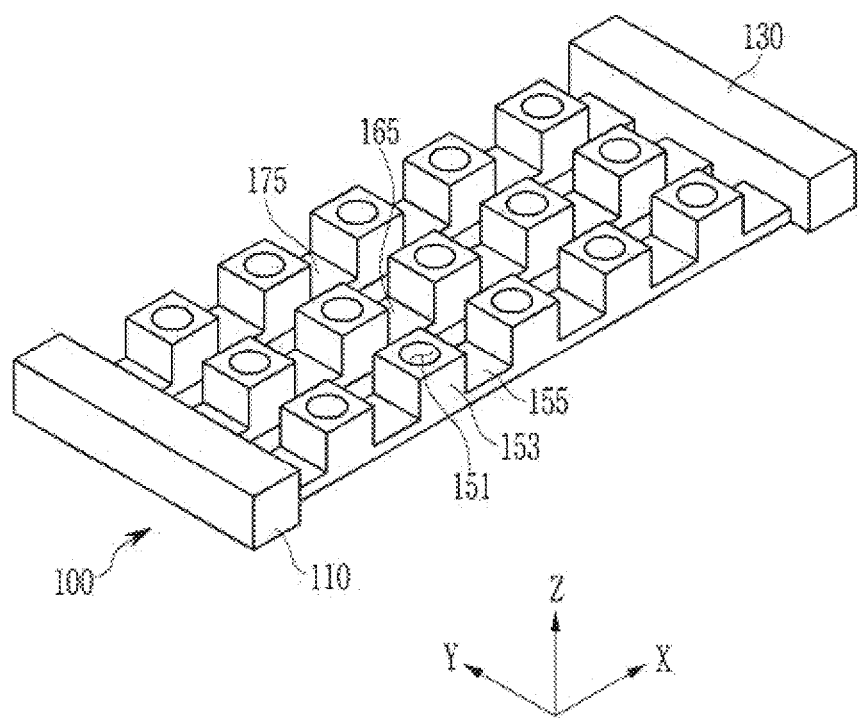
[FIG. 27]

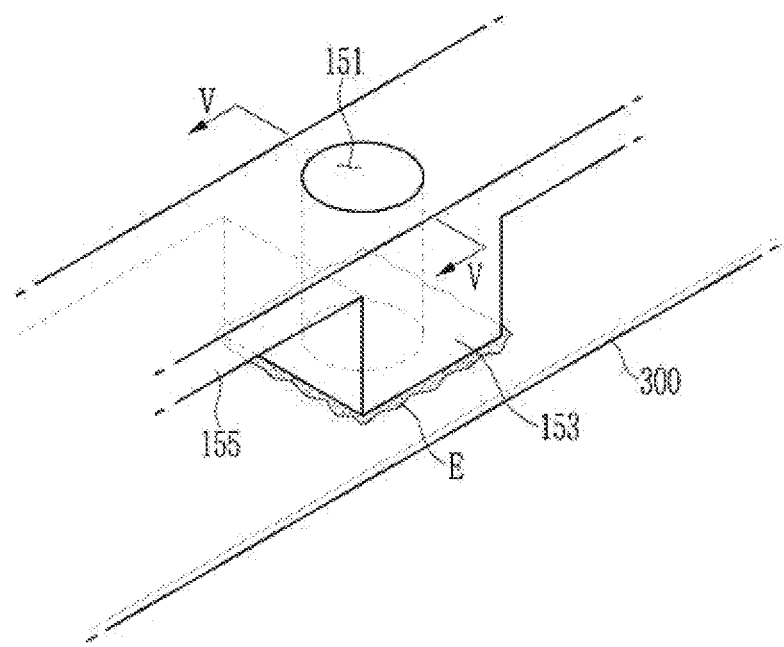
[FIG. 28]

[FIG. 29]
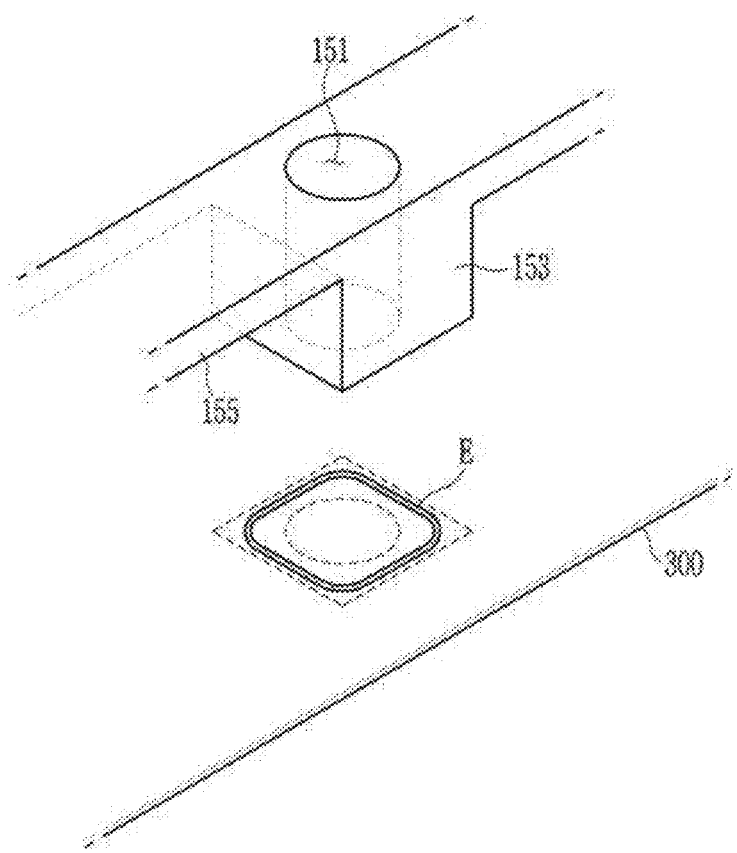
[FIG. 30]
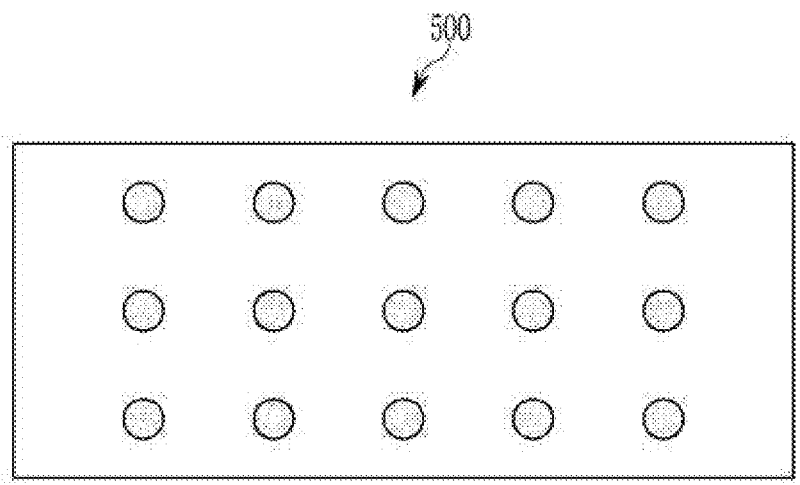

[FIG. 31]
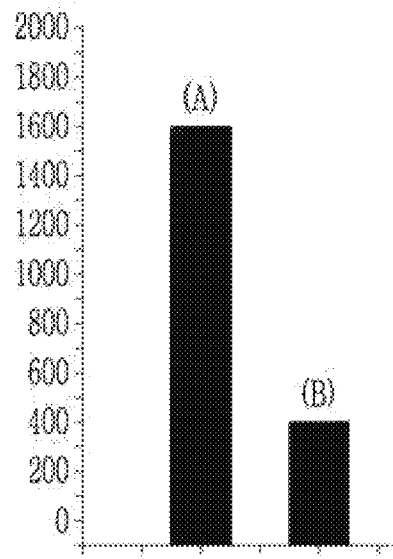
[FIG. 32]
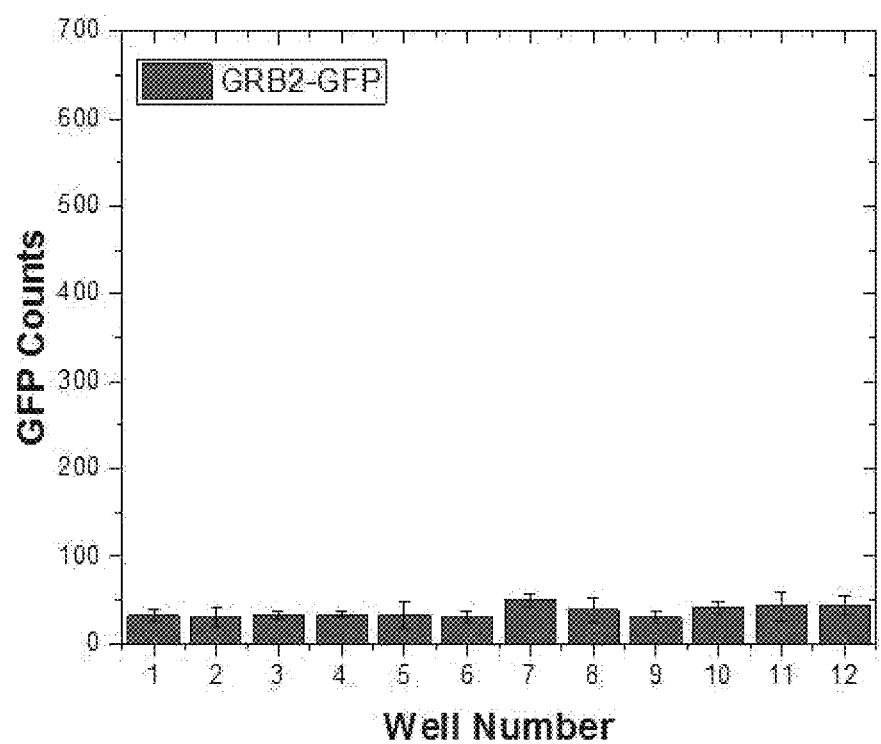

[FIG. 33]
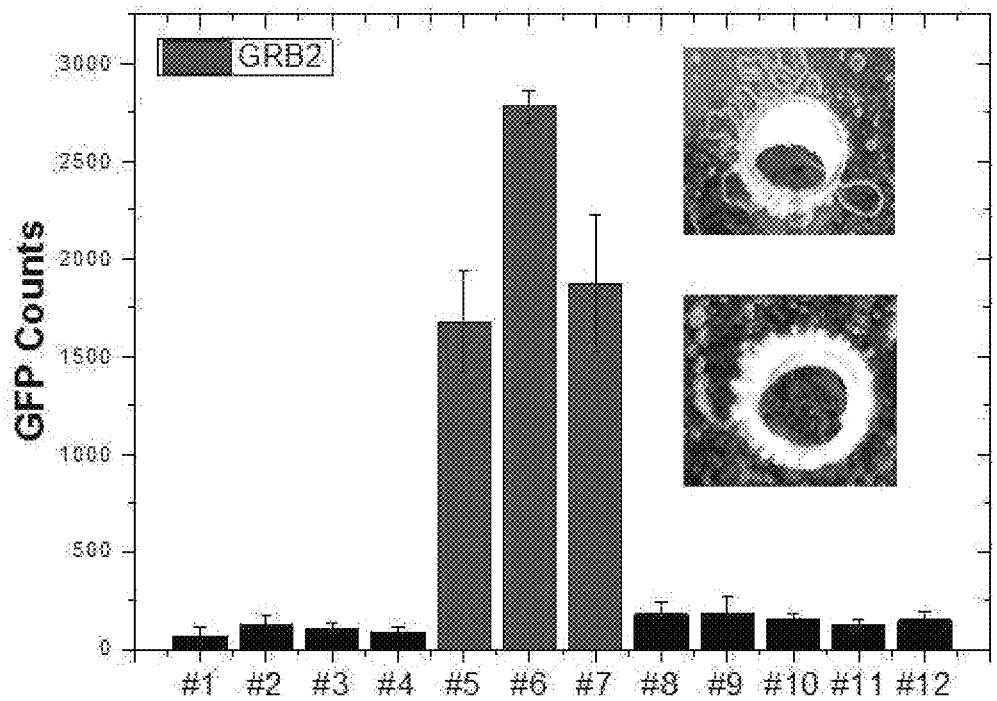
[FIG. 34]
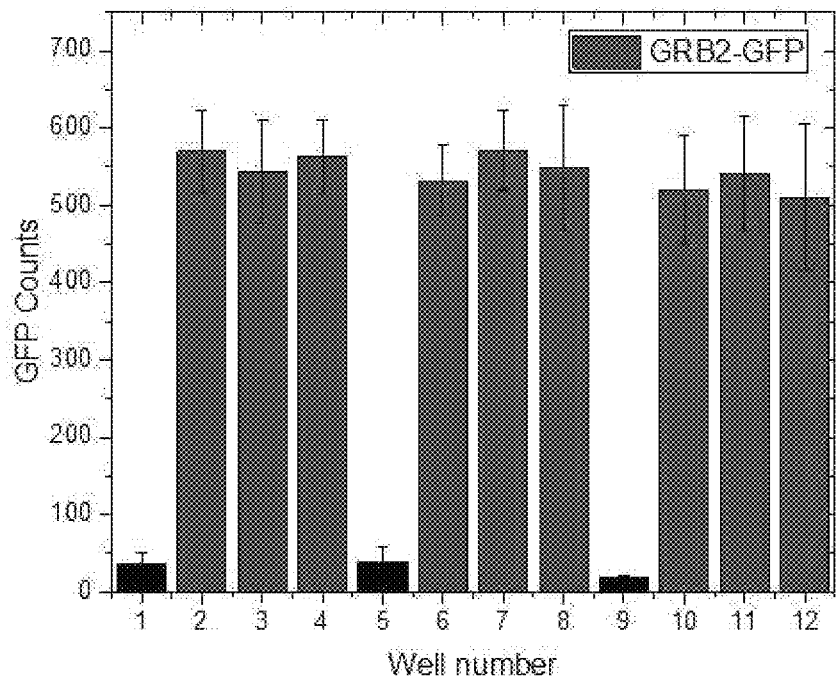

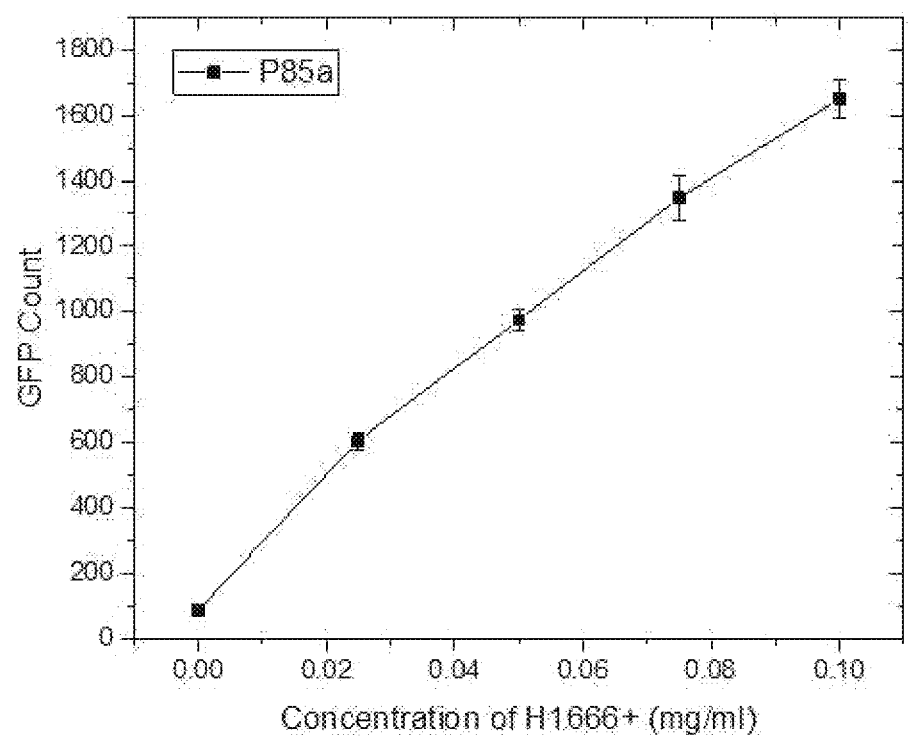
[FIG. 35]

[FIG. 36]
Blank
| Mean | STD |
|---|---|
| 26.11 | 5.01 |
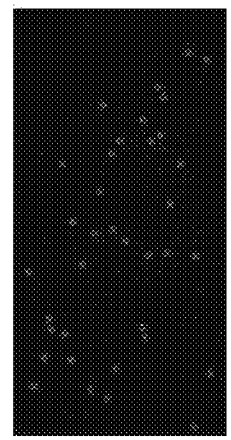
CV% = 19.18%
GRB2-GFP
| Mean | STD |
|---|---|
| 544.58 | 21.22 |
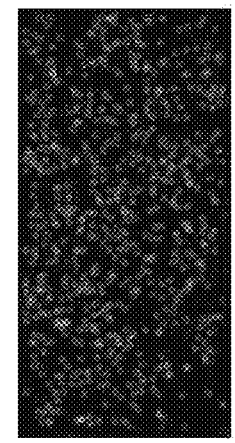
CV% = 3.89%
[FIG. 37]
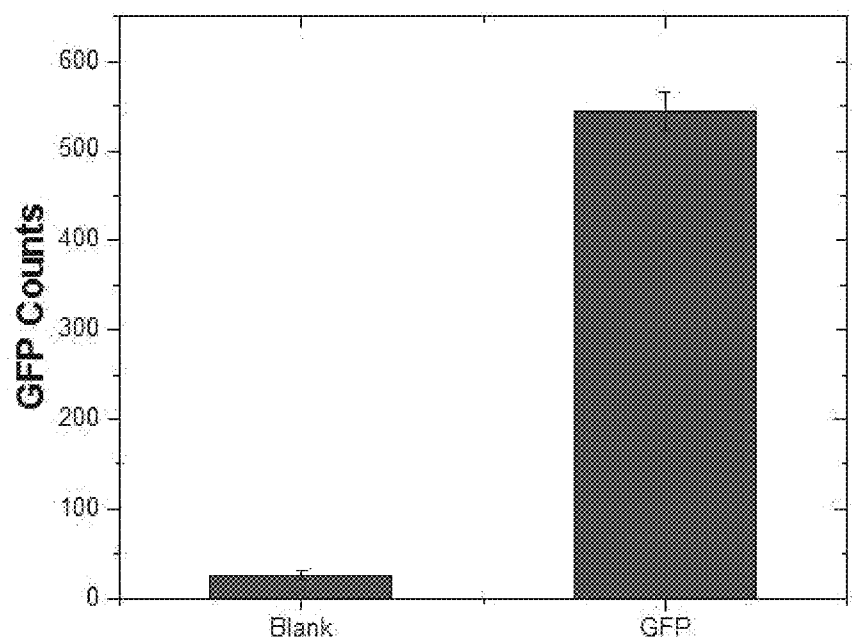

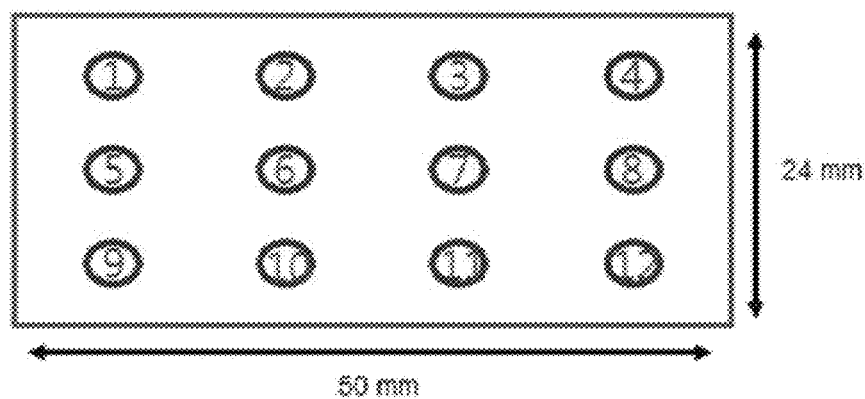
[FIG. 38]

METHOD AND APPARATUS FOR ANALYSIS OF PROTEIN-PROTEIN INTERACTION

TECHNICAL FIELD

The present invention relates to a method for analyzing an activated state of a signaling pathway in a cell or tissues through protein-protein interaction analysis, a method for screening a personalized therapeutic agent and/or for monitoring the efficacy of a therapeutic agent, and a device for use therein.

BACKGROUND ART

Up to recently, personalized diagnosis, prognosis prediction, and treatment of diseases have primarily based on genomic profiling. However, certain diseases such as cancers are caused by abnormal interactions of cells constituting the human body, and more particularly from abnormal interaction among various proteins that constitute and regulate cells. Thus, the observation of individual proteins through genetic profiling alone cannot provide a full explanation for the causes of diseases. Indeed, even patients having the same genetic properties in the context of genetic profiling differ from each other when it comes to sensitivity to targeted anticancer agents, and moreover show various prognoses. Accurate analysis of protein-protein interaction not only allows for understanding how an intracellular signaling network is changed, but also is expected to provide information on the progression and characteristics of individual cancers and therapeutic methods therefor.

DISCLOSURE

Technical Problem

One embodiment provides a method for measuring (identifying, determining, and/or analyzing) the activation of a signaling pathway in a cell or tissue, comprising a step of measuring protein-protein interaction between a first protein and a second protein, wherein the first protein is involved in the signaling pathway in the cell or tissue and the second protein is a downstream protein of the signaling pathway of the first protein.

Another embodiment provides a method for predicting responsiveness of a cell or tissue or a subject from which the cell or tissue is derived, to a first-protein-targeting drug, or for providing information for the prediction, the method comprising a step of measuring protein-protein interaction between the first protein and a second protein, wherein the first protein is involved in a signaling pathway in the cell or the tissue and the second protein is a downstream protein of the signaling pathway of the first protein.

Another embodiment provides a method for selecting a subject suitable for a first-protein-targeting therapy or for providing information for the selection, the method comprising a step of measuring protein-protein interaction between the first protein and a second protein, wherein the first protein is involved in a signaling pathway in the cell or the tissue and the second protein is a downstream protein of the signaling pathway of the first protein.

Another embodiment provides a method for screening either a first protein as a target suitable for application to a cell or tissue or a subject (individual patient) from which the cell or tissue is derived, or a drug targeting the first protein, or for providing information for the screening, the method comprising a step of measuring protein-protein interaction between the first protein and a second protein, wherein the first protein is involved in a signaling pathway in the cell or the tissue and the second protein is a downstream protein of the signaling pathway of the first protein, and the step of measuring protein-protein interaction is carried out for at least two first proteins.

Another embodiment provides a method for monitoring responsiveness of a cell or tissue or subject to a first-protein-targeting drug or for providing information for the monitoring, the method comprising a step of measuring protein-protein interaction between the first protein and a second protein in the cell or tissue treated with the first-protein-targeting drug or the subject administered with the drug, wherein the first protein is involved in a signaling pathway in the cell or the tissue and the second protein is a downstream protein of the signaling pathway of the first protein.

Another embodiment provides a method for screening a first-protein-targeting drug, the method comprising a step of measuring protein-protein interaction between a first protein and a second protein in an isolated cell or tissue treated with a drug candidate targeting the first protein or in a cell or tissue derived from a subject administered with the drug candidate, wherein the first protein is involved in a signaling pathway in the cell or the tissue and the second protein is a downstream protein of the signaling pathway of the first protein.

Another embodiment provides a device for use in the methods described above.

Technical Solution

An embodiment of the description provides a method for measuring (identifying, determining, and/or analyzing) activation of a signaling pathway in a cell or tissue, the method comprising a step of measuring protein-protein interaction between a first protein and a second protein, wherein the first protein is involved in a signaling pathway in the cell or tissue and the second protein is selected from downstream proteins of the signaling pathway of the first protein.

Another embodiment provides a method for predicting responsiveness of a cell or tissue or a subject from which the cell or tissue is derived, to a first-protein-targeting drug, or for providing information for the prediction, the method comprising a step of measuring protein-protein interaction between a first protein and a second protein, wherein the first protein is involved in a signaling pathway in the cell or tissue and the second protein is selected from downstream proteins of the signaling pathway of the first protein. When at least two first proteins are used, the first-protein-targeting drug may target one or at least two of the first proteins.

Another embodiment provides a method for selecting a subject suitable for a first-protein-targeting therapy or for providing information for the selection, the method comprising a step of measuring protein-protein interaction between a first protein and a second protein, wherein the first protein is involved in a signaling pathway in the cell or tissue and the second protein is selected from downstream proteins of the signaling pathway of the first protein. When two or more kinds of the first protein are used, the first-protein-targeting therapy may target at least one of the two or more kinds. The therapy may further comprise steps of prescribing a first-protein-targeting drug and/or administering a first-protein-targeting drug. In this regard, the subject suitable for the first-protein-targeting therapy may be characterized as a subject on which the first-protein-targeting drug exerts a desired effect.

Another embodiment provides a method for monitoring responsiveness of a cell or tissue or a subject to a first-protein-targeting drug or for providing information for the monitoring, the method comprising a step of measuring protein-protein interaction between a first protein and a second protein in the cell or tissue treated with the first-protein-targeting drug or the cell or tissue isolated from the subject to which the drug has been administered, wherein the first protein is involved in a signaling pathway in the cell or tissue and the second protein is a downstream protein of the signaling pathway of the first protein.

Another embodiment provides a method for screening a first-protein-targeting drug, the method comprising a step of measuring protein-protein interaction between a first protein and a second protein in an isolated cell or tissue treated with a drug candidate targeting the first protein, wherein the first protein is a protein involved in a signaling pathway in the cell or tissue and the second protein is a downstream protein of the signaling pathway of the first protein.

Hereinafter, more detailed description will be given.

The term "protein-protein interaction" (PPI), as used herein, may refer to the physical and/or chemical binding or complex formation between a first protein and a second protein, which may be measured in terms of at least one index including binding frequency, binding intensity (strength), binding time, and the like. In addition, interaction (binding) between the first and the second protein may include interaction (binding) via a different intermediate protein (located between the first and the second protein in a signaling pathway) as well as direct interaction (binding) therebetween. In this disclosure, the protein-protein interaction may be a single-molecule reaction (i.e. reaction between one molecule of a first protein and one molecule of a second protein).

In this disclosure, the first protein and the second protein are each independently at least one selected from proteins involved in a signaling pathway of a cell or tissue in a eukaryotic organism (for example, multicellular animals, multicellular plants, etc.). In one embodiment, the protein-protein interaction between the first and the second protein may not be a weak and transient protein-protein interaction, because it is an interaction on a biological signaling pathway.

As used herein, the term "first protein" may refer to more than one kind (e.g., from 1 to 10 kinds, from 1 to 8 kinds, from 1 to 6 kinds, from 1 to 5 kinds, from 1 to 4 kinds, from 1 to 3 kinds, from 2 to 10 kinds, from 2 to 8 kinds, from 2 to 6 kinds, from 2 to 5 kinds, from 2 to 4 kinds, from 2 to 3 kinds, from 3 to 10 kinds, from 3 to 8 kinds, from 3 to 6 kinds, from 3 to 5 kinds, or from 3 to 4 kinds) proteins involved in a signaling pathway. In addition, the term "second protein" may mean a protein that interacts with (binds to) the first protein, which may be at least one, at least two, or at least three different kinds (e.g., from 1 to 10 kinds, from 1 to 8 kinds, from 1 to 6 kinds, from 1 to 5 kinds, from 1 to 4 kinds, from 1 to 3 kinds, from 2 to 10 kinds, from 2 to 8 kinds, from 2 to 6 kinds, from 2 to 5 kinds, from 2 to 4 kinds, from 2 to 3 kinds, from 3 to 10 kinds, from 3 to 8 kinds, from 3 to 6 kinds, from 3 to 5 kinds, or from 3 to 4 kinds) proteins selected from the group consisting of proteins involved in a downstream pathway of the signaling pathway in which the first protein is involved. When two or more proteins are used as the first protein, the second protein may be at least one selected independently with respect to each first protein, and the second proteins independently selected for each of the first proteins may be different from each other or overlap each other in part or entirety.

In this disclosure, the first protein may be selected from proteins relevant to disease state (e.g., cancer, inflammation, other immune diseases, etc.), thereby providing information useful for treatment (and/or alleviation and/or reduction) of the disease (e.g., cancer, inflammation, other immune diseases, etc.). In this context, the first protein may be a target protein for therapy. In detail, the first protein may be a protein that is targeted by a therapeutic agent for a disease to be treated or by a therapeutic agent to be tested for an effect on the disease. Thus, the first protein may be appropriately selected depending on the disease to be treated or the therapeutic agent to be tested for effects.

In one embodiment, the first protein may be selected from proteins involved in an upstream pathway of a biological signaling pathway in a cell or tissue, and may be at least one, at least two, or at least three different kinds (e.g., from 1 to 10 kinds, from 1 to 8 kinds, from 1 to 6 kinds, from 1 to 5 kinds, from 1 to 4 kinds, from 1 to 3 kinds, from 2 to 10 kinds, from 2 to 8 kinds, from 2 to 6 kinds, from 2 to 5 kinds, from 2 to 4 kinds, from 2 to 3 kinds, from 3 to 10 kinds, from 3 to 8 kinds, from 3 to 6 kinds, from 3 to 5 kinds, or from 3 to 4 kinds) selected from cell membrane proteins that are located on the cell membrane and have a domain exposed to an extracellular environment (e.g., an aqueous environment), thereby advantageously acting as a target of a therapeutic drug. For example, the first protein may be at least one, at least two, or at least three different kinds (e.g., from 1 to 10 kinds, from 1 to 8 kinds, from 1 to 6 kinds, from 1 to 5 kinds, from 1 to 4 kinds, from 1 to 3 kinds, from 2 to 10 kinds, from 2 to 8 kinds, from 2 to 6 kinds, from 2 to 5 kinds, from 2 to 4 kinds, from 2 to 3 kinds, from 3 to 10 kinds, from 3 to 8 kinds, from 3 to 6 kinds, from 3 to 5 kinds, or from 3 to 4 kinds) proteins selected from all kinds of cell membrane proteins comprising a variety of receptors located on a cell membrane, structural proteins coupled with microfilaments, cell adhesion molecules, membrane enzymes, membrane receptors, carrier proteins, channel proteins, transport proteins, lipid-anchored proteins, etc.

In one embodiment, the first protein may be at least one, at least two, or at least three kinds (e.g., from 1 to 10 kinds, from 1 to 8 kinds, from 1 to 6 kinds, from 1 to 5 kinds, from 1 to 4 kinds, from 1 to 3 kinds, from 2 to 10 kinds, from 2 to 8 kinds, from 2 to 6 kinds, from 2 to 5 kinds, from 2 to 4 kinds, from 2 to 3 kinds, from 3 to 10 kinds, from 3 to 8 kinds, from 3 to 6 kinds, from 3 to 5 kinds, or from 3 to 4 kinds) proteins selected from the group consisting of receptor tyrosine kinases (RTK) (e.g., epidermal growth factor receptor (EGFR; ErbB1), human epidermal growth factor receptor 2 protein (HER2; ErbB2), human epidermal growth factor receptor 3 protein (HER3; ErbB3), hepatocyte growth factor receptor (HGFR; MET), platelet-derived growth factor receptors (PDGFR; e.g., PDGFR-alpha, PDGFR-beta, etc.), vascular endothelial growth factors (VEGFR; e.g., VEGFR1, VEGFR2, VEGFR3, etc.), insulin-like growth factor 1 Receptor (IGF1R), ephrin receptors, fibroblast growth factor receptor (FGFRs; e.g., FGFR1, FGFR2, etc.), Insulin-like Growth Factor Receptor (IGFR; e.g., IGF1R, etc.), c-KIT, RET receptor tyrosine kinase, Anaplastic lymphoma kinase (ALK), etc.); Toll-like receptors (e.g., TLR1, TLR2, TLR3, TLR4, TLR5, TLR6, TLR7, TLR8, TLR9, TLR10, TLR11, TLR12, TLR13); G-protein-coupled receptors (GPCR); transferrin receptors; low-density lipoprotein; LDL) receptors; ROS1; BCR-Abl1 fusion proteins; non-receptor-type kinases (e.g., BRAF, mitogen-activated protein kinase kinase (MEK), Sic, phosphoinositide 3-kinase (PI3K), cyclin-dependent kinases (CDK; e.g., CDK4, CDK6, etc.) etc.); GTPases (e.g., KRAS, etc.); hormone receptors (e.g., estrogen receptors (ER), progesterone receptors (PR), androgen receptors (AR), etc.); anti-apoptotic proteins (e.g., B-cell lymphoma 2 (BCL2), Bcl-2-like protein 11 (BIM); immune checkpoint proteins (e.g., cytotoxic T-lymphocyte-associated antigen 4 (CTLA-4), programmed death 1 (PD-1), programmed death-ligand 1 (PD-L1), etc.), but not be limited thereto.

The term "hepatocyte growth factor receptor (MET or c-Met)" refers to a receptor tyrosine kinase to which a hepatocyte growth factor binds. The c-Met protein may be one derived from any species, for example, those derived from primates such as human c-Met (e.g., NP_000236.2), monkey c-Met (e.g., *Macaca mulatta*, NP_001162100), and the like, or those derived from rodents such as mouse c-Met (e.g., NP_032617.2), rat c-Met (e.g., NP_113705.1) and the like. The proteins include, for example, a polypeptide encoded by the nucleotide sequence deposited under GenBank Accession Number NM_000245.3, or a protein having the amino acid sequence deposited under GenBank Accession Number NM_000236.2, or extracellular domains thereof. The receptor tyrosine kinase c-Met is involved in various mechanisms including, for example, oncogenesis, cancer metastasis, cancer cell migration, cancer cell invasion, angiogenesis, etc.

The "epidermal growth factor receptor (EGFR)", "human epidermal growth factor receptor 2 protein (HER2)", and "human Epidermal growth factor receptor 3 protein (HER3)" are each a member of receptor tyrosine kinases (RTKs) in the HER family consisting of EGFR (HER1), HER2, HER3, and HER4. Binding of a ligand to the extracellular domain of EGFR, HER2, or HER3 induces receptor homo- or heterodimerization with a different ErbB receptor molecule, which causes intracellular auto-phosphorylation of specific tyrosine residues on the receptor. EGFR auto-phosphorylation leads to a downstream signaling network including MAPK and PI3K/Akt activation, which has influence on cell proliferation, angiogenesis and metastasis. Overexpression, gene amplification, mutation, or rearrangement of EGFR, HER2 and/or HER3 is frequently observed in various kinds of human malignant tumors and is associated with poor prognosis and bad clinical outcomes. For such reasons, EGFR, HER2, and/or HER3 have become important targets in anticancer therapy.

EGFR, HER2, or HER3 may be derived from primates such as humans, monkeys, etc., or from rodents such as mice, rats, etc. For example, the EGFR may be the polypeptide encoded by the nucleotide sequence (mRNA) deposited under GenBank Accession Nos. JQ739160, JQ739161, JQ739162, JQ739163, JQ739164, JQ739165, JQ739166, JQ739167, NM_005228.3, NM_201284.1, NM_201282.1, or NM_201283.1. For example, the HER2 may be the polypeptide encoded by the polypeptide sequence (mRNA) deposited under GenBank Accession No. X03363.1. For example, the HER3 may be the polypeptide encoded by the nucleotide sequence deposited under GenBank Accession No. NM_001982.

The "Vascular Endothelial Cell Growth Factor Receptor (VEGFR)" binds to vascular endothelial growth factor (VEGF), which is present in vascular endothelial growth factor normal cells and is particularly secreted by cancer cells, to give rise to angiogenesis, resulting in the supply of nutrients necessary for tumor cells. The overexpression of VEGFR is a cause of various diseases and is particularly associated with bad prognosis such as cancer cell invasion and metastasis as well as oncogenesis. For such reasons, VEGF has become an important target in anticancer therapy. VEGFR may be derived from primates such as humans, monkeys, etc. or rodents such as mice, rats, etc. For example, the VEGFR may be the polypeptide encoded by the nucleotide sequence (mRNA) deposited under GenBank Accession Number AF063657.2.

The "platelet-derived growth factor receptors (PDGFR)" are cell surface tyrosine kinase receptors and are associated with the regulation of cell proliferation, differentiation, and growth and the onset of various diseases including cancer. The PDGFR may be derived from primates such as humans, monkeys, etc. or rodents such as mice, rats, etc. For example, the PDGFR may be the polypeptide encoded by the nucleotide sequence (mRNA) deposited under GenBank Accession Nos. NM_006206.4 (PDGFR-A), NM_002609.3 (PDGFR-B), or NM_016205.2 (PDGFR-C).

The "Insulin-like Growth Factor 1 Receptor (IGF1R)", which belongs to the large class of receptor tyrosine kinases, is a transmembrane receptor that is activated by insulin-like growth factor 1 (IGF-1). The IGF1R may be derived from mammals including primates such as humans, monkeys, etc. or rodents such as mice, rats, etc. For example, the IGF1R may be the polypeptide encoded by the nucleotide sequence (mRNA) deposited under GenBank Accession No. NM_000875.3.

The "ephrin receptors", which are a group of cell surface tyrosine kinases, are implicated in the regulation of a host of processes critical to embryonic development, including axon guidance, formation of tissue boundaries, cell migration, and segmentation. The ephrin receptors may be derived from mammals including primates such as humans, monkeys, etc. or rodents such as mice, rats, etc. For example, the ephrin receptors may be the polypeptides encoded by the nucleotide sequences (mRNA) deposited under GenBank Accession Nos. NM_004440.3, NM_004438.3, NM_004431.3, NM_004442.6, NM_017449.3, NM_004093.3, NM_004441.4, NM_182472.2, NM_005232.4, NM_005233.5, NM_173641.2, NM_001099439.1, NM_001080448.2, NM_001080448.2, NM_004443.3, NM_182689.1, NM_004428.2, NM_004439.5, NM_001962.2, NM_004429.4, NM_182644.2, NM_004952.4, NM_173655.2, NM_182690.2, NM_020526.3, NM_001406.3, NM_005227.2, and NM_182685.1.

The "transferrin receptor" is a carrier protein for transferrin. It imports iron into cells through receptor-mediated endocytosis and is regulated in response to intracellular iron concentration. The transferrin receptor may be derived from mammals including primates such as humans, monkeys, etc. or rodents such as mice, rats, etc. For example, the transferrin receptor may be the polypeptide encoded by the nucleotide sequences (mRNA) deposited under GenBank Accession Nos. NM_001128148.1, NM_003234.2, NM_001206855.1, NM_003227.3, BC001188.1, or M11507.1.

The "low-density lipoprotein (LDL) receptor" is a carrier protein for transferrin which is involved in the intracellular delivery of iron through endocytosis and functions to control an intracellular iron concentration. The LDL receptor may be derived from mammals including primates such as humans, monkeys, etc. or rodents such as mice, rats, etc. For example, the LDL receptor may be the polypeptide encoded by the nucleotide sequences (mRNA) deposited under GenBank Accession Nos. NM_000527.4, NM_001195802.1, NM_001195799.1, NM_001195803.1, NM_001195800.1, or NM_001195798.1.

The "cluster of differentiation or cluster of designation (CD)" molecules are proteins that can act in numerous ways, often acting as receptors or ligands. CD molecules for humans are about 350 in number, and participate in various cellular responses. The cluster of differentiation may be derived from mammals including primates such as humans, monkeys, etc. or rodents such as mice, rats, etc. For example, the cluster of differentiation may be derived from all CD lineages, among others, those associated with metastasis, such as CD44, CD147, or variants thereof. In greater detail, the CD may be the polypeptides encoded by the nucleotide sequences (mRNA) deposited under GenBank Accession Nos. NM_000610.3, NM_001728.3, and X55150.1.

The "G-protein-coupled receptors (GPCRs)" are transmembrane receptor proteins that activate signal transduction pathways and cellular responses, and are involved in many diseases. GPCRs constitute a large protein family of receptors that can be divided into six classes on the basis of sequence homology and functional similarity class A or class 1 (Rhodopsin-like receptors); class B or class 2 (Secretin receptor family); class C or class 3 (Metabotropic glutamate/pheromone); class D or class 4 (Fungal mating pheromone receptors); class E or class 5 (Cyclic AMP receptors); and class F or class 6 (Frizzled/Smoothened). The GPCRs may be derived from mammals including primates such as humans, monkeys, etc. or rodents such as mice, rats, etc. For example, CPCR may be chemokine receptors (rhodopsin-like receptor subfamily) that are associated with cancer metastasis and, inter alia, CXC chemokine receptor, CC chemokine receptor, CX3C chemokine receptor, etc. More concrete examples may include polypeptides encoded by the nucleotide sequences (mRNA) provided by GenBank Accession Nos. NM_001123041.2, NM_005508.4 NM_005201.3, and NM_016602.2.

As described above, the second protein may be at least one, at least two, or at least three different kinds (e.g., from 1 to 10 kinds, from 1 to 8 kinds, from 1 to 6 kinds, from 1 to 5 kinds, from 1 to 4 kinds, from 1 to 3 kinds, from 2 to 10 kinds, from 2 to 8 kinds, from 2 to 6 kinds, from 2 to 5 kinds, from 2 to 4 kinds, from 2 to 3 kinds, from 3 to 10 kinds, from 3 to 8 kinds, from 3 to 6 kinds, from 3 to 5 kinds, or from 3 to 4 kinds) proteins selected from proteins involved in a downstream pathway of the biological signaling pathway of a cell or tissue in which the first protein is involved. Signaling pathways in cells or tissues, for example, human cells or tissues, and proteins involved therein, are relatively well established (see Untangling the ErbB signaling network, Nat. Rev. Mol. Cell Biol. 2, 127 (2001) and Cell signaling by receptor tyrosine kinases, Cell 141, 1117 (2010)). Once a first protein of interest is selected, it would be self-evident to a person skilled in the relevant art to select a second protein that is involved in a downstream pathway of the first protein-involved signaling pathway.

In addition, the phrase "a second protein is selected from downstream proteins of the signaling pathway of the first protein" may mean that a second protein is a protein selected from all proteins that interact with the first protein on a signaling pathway, directly or indirectly via at least one intermediate protein, wherein, on the signal transduction, the first protein performs upstream signal transduction.

Further, it is well known that in some cases, one protein is involved in various biological signaling pathways, so that multiple signaling pathways can form a network. Therefore, in case at least two proteins are used as the first protein, at least one of the second proteins for any one of first protein may overlap with at least one of the second proteins for another first protein(s) (that is, when at least two first proteins are used, the second proteins for the at least two first proteins may be different from each other or identical in part or entirety).

In one embodiment, the first protein may be at least one selected from the group consisting of EGFR, MET, HER2, and HER3. The second proteins for each of the respective first proteins may be the same or different, and may be each independently at least one selected from the group consisting of phospholipase C (PLC) (e.g., PLC-gamma (PLC-gamma 1) (i.e., GenBank Accession No. NP_002651.2, NP_877963.1, NP_037319.1, etc.), or an SH2 domain thereof (Src homology 2 domain: inclusive of at least one of N-terminal SH2 domain and C-terminal SH domain; e.g., the amino acid sequence region from the $545^{th}$ a.a. to the $765^{th}$ a.a. on NP_037319.1 or the amino acid sequence region from the $540^{th}$ or $545^{th}$ a.a. to the $765^{th}$ a.a. on NP_002651.2), a growth factor receptor-binding protein (Grb; e.g., Grb2 (i.e., GenBank Accession No. NP_002077.1, NP_987102.1, etc.) or a part thereof (i.e., an SH2 domain (the amino acid sequence region from the $57^{th}$ a.a. to the $155^{th}$ a.a. on NP_002077.1), an SH3_N-SH2 domain (the amino acid sequence region from the $1^{st}$ a.a. to the $154^{th}$ a.a. on NP_002077.1), or an SH2-SH3_C domain (the amino acid sequence region from the $57^{th}$ a.a. to the $217^{th}$ a.a. on NP_002077.1)), phosphatidylinositol 3-kinase regulatory subunits (phosphatidylinositol 3-kinase regulatory subunit alpha; PIK3R1; p85-alpha; e.g., GenBank Accession No. NP_001229395.1, NP_852556.2, NP_852664.1, NP_852665.1, P26450.2, etc.) or SH2 domains thereof (e.g., an SH2_N domain (the amino acid sequence region from the $333^{rd}$ a.a. to the $428^{th}$ a.a.), an SH2_C domain (the amino acid sequence region from the $624^{th}$ a.a. to the $718^{th}$ a.a.), or a tandem SH2 domain (the amino acid sequence region from the $333^{rd}$ a.a. to the $718^{th}$ a.a.) on NP_852664.1 (human p85a); or an SH2_N domain (the amino acid sequence region from the $333^{rd}$ a.a. to the $428^{th}$ a.a.), an SH2_C domain (the amino acid sequence region from the $624^{th}$ a.a. to the $718^{th}$ a.a.) or a tandem SH2 domain (the amino acid sequence region from the $333^{rd}$ a.a. to the $718^{th}$ a.a.) on P26450 (mouse p85a)), but not be limited thereto.

An embodiment provided in this disclosure exemplifies lung cancer in which a set of EGFR, MET, HER2, and HER3 falls within the scope of the first proteins and PLC-gamma 1, Grb2, and p85-alpha are used as the second proteins common to the first proteins.

Another embodiment provided in this disclosure relates to breast cancer in which a set of HER2 and HER3 falls within a scope of the first proteins and PLC-gamma 1, Grb2, and p85-alpha are used as the second proteins common to the first proteins, but is not limited thereto. Based on the foregoing description, the first protein and the second protein may be suitably selected depending on the disease to be treated or the therapeutic agent to be tested for its efficacy, and the selection thereof may be clear to a person skilled in the relevant art.

In the method provided in this disclosure, the step of measuring protein-protein interaction between the first protein and the second protein may be performed outside a living body or outside a cell (in vitro) for isolated cells or tissues.

The step of measuring protein-protein interaction between the first protein and the second protein may comprise at least one of the following sub-steps of:

(1) adding a test sample containing the first protein to a substrate comprising a material specifically binding to the first protein, to prepare a substrate having the first protein immobilized thereon;

(2) adding a labeled (marker-conjugated) second protein to the first-protein-immobilized substrate, to allow reaction thereof;

(3) measuring a signal from the reactant obtained in step (2) (protein-protein interaction measuring); and (4) measuring an activation level of the first protein based on the signal measured in step (3).

The step (4) of measuring an activation level of the first protein based on the signal measured in step (3) may be a step in which the signal measured in step (3) is used to obtain a signal value of a unit amount of the first protein in the test sample added in step (1).

In an embodiment, the step (4) may be carried out through a step in which the signal measured in step (3) is utilized to obtain a signal value of a unit amount of the first protein in the test sample added in step (1). Alternatively, the step (4) may comprise the steps of:

(4-1) using the signal measured in step (3), to obtain a signal value of a unit amount of the test sample added in step (1) (measuring a level of protein-protein interaction); and (4-2) using the signal, measured in step (4-1), of a unit amount of the test sample, to obtain a value of a unit amount of the first protein contained in the test sample (measuring an activation level).

In another embodiment, the method may further comprise, subsequent to step (4), a step of:

(5) comparing the result obtained in step (4) with that obtained in a reference sample.

Below, a detailed explanation will be given of the steps.

Step (1): Preparation of Substrate Having First Protein Immobilized Thereto

In step (1), a test sample containing a first protein is added to a substrate comprising, on the surface thereof, a material specifically binding to the first protein to prepare a substrate having the first protein immobilized thereto.

The first protein is as described above.

The test sample may be any biological sample, as long as it is available in a test for responsiveness to a first-protein-targeting drug for activating a signaling pathway in a cell or tissue.

For example, the test sample may be a cell or tissue isolated from a subject, a lysate, homogenate, or extract of cells or tissues, or body fluid (e.g., blood (whole blood, plasma, or serum), saliva, etc.). The subject may be selected from the group consisting of all mammals (e.g., primates such as humans, monkeys, etc., rodents such as mice, rats, etc.) in which at least one of the following processes may be conducted: a test for activating a signaling pathway in a cell or tissue in which a first protein is involved; a responsiveness test for a first-protein-targeting drug; a test for determining whether the subject is suitable for the targeted therapy of the first protein; monitoring for targeted therapy effects of the first protein; and/or selection of effective targeted therapeutic agents for the first protein. In one embodiment, the subject may be a patient with a disease related to the first protein. The first protein-related disease may be a disease caused by the overexpression of the first protein or the activation of a signaling pathway in a cell or tissue in which the first protein is involved, for example, cancer. In one exemplary embodiment, the test sample may include cells isolated from individual cancer patients (for example, particular subjects in which a degree of activation of a first protein-involved signaling pathway in a cell or tissue will be measured or responsiveness to a first-protein-targeting drug will be tested, said drug being subject to a determination of suitability for use in the first-protein-targeting therapy, or to evaluation for selection of an effective targeted therapeutic agent for the first protein, e.g., cancer cells. In case of a tissue, a size of at least 125 mm$^3$ may be needed for homogenization. A dose for a single test may be about $1/50$ to about $1/75$ of the amount (at least 125 mm$^3$), but is not limited thereto. As for cells (cancer cells), the amount thereof necessary for a single test may be about 10 cells to $10^{10}$ cells, about 10 cells to $10^7$ cells, about 10 cells to $10^5$ cells, about $10^3$ cells to $10^{10}$ cells, about $10^3$ cells to $10^7$ cells, or about $10^3$ cells to $10^5$ cells, for example, about $10^4 \pm 50$ cells, but is not limited thereto, and may be appropriately determined according to the cell strain.

For the prediction of responsiveness to a first-protein-targeting drug and/or the selection of a subject suitable for first-protein-targeting therapy according to one embodiment, the test sample may be a cell or tissue in which therapy for targeting the first protein (for example, the administration of a first-protein-targeting drug) has not been performed or a cell or tissue isolated from a subject in which therapy (or drug administration) has not been performed. In a method for monitoring responsiveness to first-protein-targeting therapy, the test sample may be a cell or tissue in which a therapy for targeting the first protein (for example, the administration of a first-protein-targeting drug) has been performed or a cell or tissue isolated from a subject in which the therapy (or drug administration) has been performed.

The substrate may have any substance and/or structure that allows for the immobilization of the first protein on the surface of the substrate (whether crystalline or non-crystalline). In one embodiment, the substrate is a matter that has a refractive index as high as or higher than that of water (i.e. as high as about 1.3) accounting for a majority of bio-substances in consideration of ease of detection of a marker signal. In an embodiment, the substrate may range in thickness from about 0.1 to about 1 mm, from about 0.1 to about 0.5 mm, from 0.1 to about 0.25 mm, or from about 0.13 to about 0.21 mm, with a refractive index of about 1.3 to about 2, about 1.3 to about 1.8, about 1.3 to about 1.6, or about 1.5 to about 1.54. So long as its refractive index falls within the range, any substrate may be used. For example, the substrate may be obtained from a material selected from the group consisting of glass (refractive index: about 1.52), quartz, and the like, but is not limited thereto. The substrate may be in any form typically used for observation of biological samples and may be, for example, in a well-type form, a channel-type form, an array form, a microfluidic chip form, a microtube (capillary) form, etc., but is not limited thereto. For fluorescent microscopic observation, the substrate on which a sample is applied may be covered with a cover glass. The material for the cover glass is as described above, having a thickness in the range presented above for the substrate or below the range (e.g., a refractive index of 1.52 and a thickness of 0.17 mm, but without limitation thereto).

The substance binding specifically to the first protein may be selected from among all substances capable of binding thereto, for example, from the group consisting of an antibody binding specifically to the first protein, an antigen-binding fragment thereof (e.g., scFv, (scFv)2, scFv-Fc, Fab, Fab', F(ab')2, and the like of an antibody), an aptamer (protein or nucleic acid molecule), and a small-molecule compound. In this regard, the substance binding specifically to the first protein may bind to the first protein at a site that does not interfere with interaction between the first protein and the second protein, that is, a site other than the site at which the first protein interacts with (binds to) the second protein.

In one embodiment, the substrate may be appropriately surface modified to include (immobilize) a biological substance (e.g., antibodies, etc.) binding specifically to the first protein onto the surface thereof or may have a substance binding specifically to the first protein immobilized on the surface thereof. For the surface modification, one surface of the substrate may be treated (e.g., coated) with any compound that has a functional group capable of immobilizing a biological material (e.g., antibody, etc.) binding specifically to the first protein, and may be treated with, for example, a compound including a functional group selected from the group consisting of an aldehyde group, a carboxyl group, and an amine group. In one embodiment, the compound including a functional group selected from the group consisting of an aldehyde group, a carboxyl group, and an amine group may be one selected from the group consisting of biotin, bovine serum albumin (BSA), biotinylated bovine serum albumin, polyethylene glycol (PEG), biotinylated PEG (polyethylene glycol-biotin or PEG-biotin), and polysorbate (e.g., Tween20), but is not limited thereto. The surface-treated substrate may be further treated (e.g., coated) with one selected from the group consisting of neutravidin, streptavidin, and avidin.

Step (2): Reaction of First Protein with Second Protein

In step (2), a labeled second protein is added to the prepared substrate having the first protein immobilized thereto and reacted with the first protein.

The second protein is as described above.

The labeled second protein may mean a form of the second protein that has been labeled with a marker generating a detectable signal (a marker is attached, for example, chemically (e.g., covalently or non-covalently), recombinantly, or physically) or with a tag to which a marker can be coupled. The detectable signal may be selected from among all signals (e.g., light, radiation, etc.) that can be detected through typical enzymatic reactions, fluorescence, luminescence, and/or radioactive radiation. The marker may be at least one selected from the group consisting of small-molecule compounds, proteins, peptides, and nucleic acids, all of which can generate the marker signal, and, for example, from the group consisting of fluorescent dye (small-molecule compounds; Cyanine, Alex, DyLight, FluoProbes, etc.), a fluorescent protein (for example, green fluorescent protein (GFP, enhanced GFP), yellow fluorescent protein (YFP), cyan fluorescent protein (CFP), blue fluorescent protein (BPF), red fluorescent protein (RFP), etc.). The tag may be at least one selected from all kinds of typically used tags, such as His-tag/Ni-NTA, etc. When the marker is used, its concentration may be suitably determined at about 1 µM or less to allow accurate and easy detection without generating noise and may range, for example, from 1 nM to 1000 nM, from 1 nM to 500 nM, from 1 nM to 100 nM, from 10 nM to 1000 nM, from 10 nM to 500 nM, or from 10 nM to 100 nM, but is not limited thereto. The signal generated from the marker may be detected by any signal detection means typically used for detection or measurement (for example, typically, a fluorescent microscope, a fluorescent camera, a fluorescence-intensity measuring (quantitating) device, etc.).

In order to more accurately measure the interaction between the first protein and the second protein, a step of washing, in a typical manner, the substrate on which the reaction has occurred may be included between the reaction step (step (2)) and a subsequent step of measuring protein-protein interaction (step 3)).

Step (3): Protein-Protein Interaction Measurement

In step (3), measurement is made of a signal from the reactant obtained in step (2). The signal measurement may be carried out using any means that can detect (or measure or identify) the marker signal used in step (2) (a signal measurable with a typical method for detecting, for example, an enzymatic reaction, fluorescence, luminescence, or radiation).

In an embodiment, the measurement of protein-protein interaction in step (3) may be performed through real-time analysis.

In an embodiment, when the marker signal is a fluorescent signal, the detection of the signal may be achieved by providing a light source to be absorbed by the marker and visualizing and/or quantifying the fluorescent signal generated by the marker by means of, for example, a fluorescent microscope, a fluorescent camera, or a fluorescence-intensity measuring (quantitating) device.

According to an exemplary embodiment, a fluorescent signal may be visualized and/or quantified using a fluorescent camera.

When the signal is a fluorescent signal, step (3) (measurement of protein-protein interaction) may comprise the steps of:

(i) providing a light source to the reactant obtained in step (2); and (ii) detecting a fluorescent signal generated by the supplied light source.

The step (i) of providing a light source is to provide a light source for the reactant of the first protein and the second protein, obtained in step (2). As long as this goal is achieved, no particular limitations are imposed on the time of provision of the light source. For example, a light source may be provided continuously from a time prior, simultaneous, or subsequent to step (1) to a time after step (2) or for a period of time immediately before, simultaneously with, or immediately after step (2), but is not limited thereto.

So long as it has a wavelength corresponding to a fluorescent signal, any light source may be used. For example, a laser, a halogen lamp, etc. may be used.

The wavelength of the light source may be controlled according to the fluorescent signal that is used, and may be selected from a range of, for example, about 300 nm to about 600 nm or about 350 nm to about 560 nm. More specifically, light is absorbed at about 480 nm in a green fluorescent protein, at about 540 nm in a yellow fluorescent protein, at about 375 nm in a blue fluorescent protein, and at about 425 nm in a cyan fluorescent protein. When green fluorescence is used for a fluorescent signal, the wavelength of the light source may be determined within a range from about 460 to about 500 nm. When yellow fluorescence is used for a fluorescent signal, the wavelength of the light source may be determined within a range from about 520 to about 560 nm. When blue fluorescence is used for a fluorescent signal, the wavelength of the light source may be determined within a range from about 350 to about 400 nm. When cyan fluorescence is used for a fluorescent signal, the wavelength of the light source may be determined within a range of from about 400 to about 450 nm.

In an embodiment, the step (3) of measuring protein-protein interaction may be carried out by providing a light source by means of a total internal reflection fluorescence (TIRF) microscope or a confocal microscope. In another embodiment, the total internal reflection fluorescence microscope may be equipped with a fluorescence camera for imaging signals, for example, an electron-multiplying charge-coupled device (EMCCD) camera or a complementary metal oxide semiconductor (CMOS) camera, to perform light source provision and fluorescent signal imaging and/or quantification.

Next, the step (3) of measuring protein-protein interaction will be described in detail with reference to an example using a total internal reflection fluorescence microscope and a fluorescence camera.

a) the substrate of step (1) or (2) is mounted on a total internal reflection fluorescence microscope. In a total internal reflection fluorescence microscope, the light source is typically directed downward. Depending on the kind of the total internal reflection fluorescence microscope, a fluorescent signal may be observed above the substrate (in this case, a light source provision unit, the substrate, and a lens, or the substrate, a light source provision unit, and a lens may be positioned in that order in the direction from bottom to top) or below the substrate (in this case, a lens, a light source provision unit, and the substrate, a light source provision unit, a lens, and the substrate, or a lens, the substrate, and a light source provision unit may be positioned in that order in the direction from bottom to top).

b) the light source may be a laser, ranging in intensity from about 0.5 mW to about 5 mW, from about 0.5 mW to about 4.5 mW, from about 0.5 mW to about 4 mW, from about 0.5 mW to about 3.5 mW, from about 0.5 mW to about 3 mW, from about 0.5 mW to about 2.5 mW, from about 0.5 mW to about 2 mW, from about 1 mW to about 5 mW, from about 1 mW to about 4.5 mW, from about 1 mW to about 4 mW, from about 1 mW to about 3.5 mW, from about 1 mW to about 3 mW, from about 1 mW to about 2.5 mW, from about 1 mW to about 2 mW, from about 1.5 mW to about 5 mW, from about 1.5 mW to about 4.5 mW, from about 1.5 mW to about 4 mW, from about 1.5 mW to about 3.5 mW, from about 1.5 mW to about 3 mW, from about 1.5 mW to about 2.5 mW, or from about 1.5 mW to about 2 mW, and may have an intensity of about 2 mW. As stated beforehand, the wavelength of the light source may be suitably selected according to fluorescent signals, markers used, and/or the components of the equipment (for example, an attenuation filter allows the use of a high-intensity light source).

c) fluorescent signals that are generated with the provision of the light source may be captured, imaged, and/or quantified by means of a fluorescence camera.

In consideration of the retention time of fluorescent signal generation (light-emission time, lifetime) of the marker, the capture (or imaging) of the fluorescent signals may be performed simultaneously with the provision of the light source or within the retention time of signal generation.

For capturing (or imaging) fluorescent signals with a fluorescence camera (e.g., EMCCD camera), exposure time, laser power, a camera gain value, total imaging frames, etc. may be suitably controlled. For example, a shorter exposure time per frame accumulates the signals on one frame to a lesser extent. To offset this, the power of the laser or the sensitivity of the fluorescent camera may be increased. In one embodiment, the exposure time per frame may be set to be about 0.001 sec to about 5 sec, about 0.001 sec to about 3 sec, about 0.001 sec to about 2 sec, about 0.001 sec to about 1 sec, about 0.001 sec to about 0.5 sec, about 0.001 sec to about 0.3 sec, about 0.001 sec to about 0.1 sec, about 0.01 sec to about 5 sec, about 0.01 sec to about 3 sec, about 0.01 sec to about 2 sec, about 0.01 sec to about 1 sec, about 0.01 sec to about 0.5 sec, about 0.01 sec to about 0.3 sec, about 0.01 sec to about 0.1 sec, about 0.05 sec to about 5 sec, about 0.05 sec to about 3 sec, about 0.05 sec to about 2 sec, about 0.05 sec to about 1 sec, about 0.05 sec to about 0.5 sec, about 0.05 sec to about 0.3 sec, about 0.05 sec to about 0.1 sec, about 0.07 sec to about 5 sec, about 0.07 sec to about 3 sec, about 0.07 sec to about 2 sec, about 0.07 sec to about 1 sec, about 0.07 sec to about 0.5 sec, about 0.07 sec to about 0.3 sec, about 0.07 sec to about 0.1 sec, about 0.1 sec to about 5 sec, about 0.1 sec to about 3 sec, about 0.1 sec to about 2 sec, about 0.1 sec to about 1 sec, about 0.1 sec to about 0.5 sec, or about 0.1 sec to about 0.3 sec, for example about 0.1 sec, but is not limited thereto.

For example, when an EMCCD camera is used, photons generated from the marker (e.g., eGFP) are measured in the form of electrons converted through the element of the EMCCD (photoelectric effect). The number of electrons generated per photon may be changed through a gain value. The higher the gain value is set, the greater the number of electrons that are generated per photon, which results in increasing the sensitivity of EMCCD, with the concomitant increase of background noise. Hence, a signal-to-noise ratio may be important. In one embodiment, the gain value may be set to fall within a scope of, but is not limited to, about 10 to about 100, about 10 to about 80, about 10 to about 60, about 10 to about 50, about 20 to about 100, about 20 to about 80, about 20 to about 60, about 20 to about 50, about 30 to about 100, about 30 to about 80, about 30 to about 60, or about 30 to about 50, for example about 40, in order to obtain an excellent signal-to-noise ratio. However, the gain value may be suitably selected in consideration of the camera sensitivity and lifetime, equipment configuration conditions, noise test conditions, etc.

Multiplication of a total number of image frames by exposure time gives a total time of photographing (exposure time×total number of frame=photographing time). Because a fluorescent signal disappears after the emission time (lifetime) of a fluorescent material, the total number of image frames and/or the exposure time may be adjusted so that the photographing is conducted within the emission time (lifetime).

In order to increase the accuracy of protein-protein interaction measurements, the imaging is conducted on one or more, for example two or more, three or more, four or more, five or more, seven or more, or ten or more, substrates (the upper limit may be determined depending on the size of the substrate and an area in which imaging is allowed) or in one or more channels (each channel includes two or more substrates). The obtained fluorescent signals can be quantified by measuring the number of signal-expressing spots (also known as PPI complex), which is regarded as a way to quantify the protein-protein interaction.

In another embodiment, the quantitation of the protein-protein interaction may be achieved by digitizing the fluorescence intensity measured in step (3) by means of a typical device.

When two or more different first proteins and/or second proteins are used, the steps (1) to (3) may be performed for each of the combinations of individual first and second proteins (that is, steps (1) to (3) may be performed repeatedly a number of times corresponding to the number of combinations of the first and the second proteins).

Step (4): Measurement of Activation Level of First Protein

In step (4) of measuring an activation level of the first protein, the signal measured in step (3) is utilized to a signal value (activation score) of a unit amount of the first protein in the test sample added in step (1).

As used herein, the term "activation of the first protein" means interaction (binding) of the first protein with the second protein, the term "activation level of the first protein" means a level of the interaction (binding) of the first protein with the second protein, and the term "activated first protein" means the first protein being in interaction (or binding) with the second protein.

The signal value for the unit amount of the first protein means a signal value (a quantitative value of a signal or signal intensity), measured in step (3), for unit weight or concentration of the first protein, and can be obtained by:
(a) dividing the signal value measured in step (3) by the weight or concentration of the first protein within the test sample, or
(b) calculating an increment of the signal value measured in step (3) with respect to an increase in the weight or concentration of the first protein within the test sample (that is, a slope of the graph where the weight or concentration of the first protein within the test sample is set forth on an X axis and the signal value measured in step (3) is set forth on a Y axis).

In the description, it is suggested that the ratio of the activated first protein in the sample represents significantly higher correlation to the responsiveness of a first-protein-targeting drug in a subject from which the sample is derived than to the amount of the first protein. That is, a higher drug responsiveness is obtained in the case where the ratio of activated first protein (activation level:activation score) is higher even if the level of the first protein in a sample relatively is low (e.g., even if the first protein is present in a low amount) than in the case where the ratio of activated first protein is lower (although the level of the first protein is relatively high; see FIGS. 19 and 20). Therefore, the present invention sets forth a feature wherein protein-protein interaction is measured and the measurement is calculated into a value in terms of a unit amount of the first protein (divided by an amount of the first protein) to provide more accurate information on drug responsiveness.

The step (4) of measuring an activation level of the first protein may be carried out:
(i) by directly dividing the signal value measured in step (3) by the weight or concentration of the first protein in the test sample added in step (1), or
(ii) through step (4-1) of dividing the signal value measured in step (3) by the weight or concentration of the test sample added in step (1) to obtain a signal value to a unit amount of the test sample (protein-protein interaction level measurement step), and step (4-2) of dividing the signal value to a unit amount of the test sample, obtained in step (4-1), by the weight or concentration of the first protein in the test sample added in step (1) to obtain a signal value of a unit amount of the first protein in the test sample (activation level measurement step).

Protein-Protein Interaction Level Measurement Step (4-1)

In the step (4-1) of measuring a protein-protein interaction level, the signal measured in step (3) is used to obtain a signal value of a unit amount of the test sample added in step (1).

The protein-protein interaction level may also be expressed as protein-protein interaction strength (PPI strength), and errors attributable to test sample conditions, such as the amount of the test sample that is used and the like, can be reduced by using the signal measured in step (3) to obtain a signal value of a unit amount of the test sample added in step (1).

The step of measuring a signal value of a unit amount of the test sample added in step (1) by use of the signal measured in step (3) can be carried out by dividing the signal measured in step (3) by the amount (concentration or weight) of the test sample or by obtaining a slope of a curve in a graph in which the signal measured in step (3) is set forth on the Y axis and the amount (concentration or weight) of the test sample added in step (1) is set forth on the X axis.

When two or more different first proteins and/or second proteins are used, the protein-protein interaction level measurement step may be performed for each of the combinations of individual first and second proteins.

When two or more different second proteins (downstream proteins) exist, the sum of PPI strength obtained for individual second proteins may be determined as the protein-protein interaction level (PPI score):

$$\text{Sum of } PPI_{test\ sample}^{1st\ protein} = \sum_{k=2nd\ protein} (PPI\ \text{strength})_k^{1st\ protein}$$

When two or more different first proteins exist, a sum of PPI scores obtained for individual first proteins may be determined as the protein-protein interaction level (PPI score).

In another embodiment, the obtained protein-protein interaction level (PPI strength or PPI score) may be normalized so that the protein-protein interaction level of the reference sample described below becomes 1, whereby the PPI strength of the test sample can be represented as a value relative to the PPI strength of the reference sample.

Activation Level Measurement Step (Step 4 or 4-2)

In step (4) (directly measuring an activation level without the step (4-1) of measuring a protein-protein interaction level (PPI score)) or step (4-2), the signal value obtained in step (3) or the signal value of a unit amount of the sample test, obtained in step (4-1), is used to obtain a value to a unit amount of the first protein contained in the test sample. In the description, the result obtained in step (4) or step (4-2) is referred to as an activation level (or activation score).

The activation level, which is obtained by dividing the signal value obtained in step (3) or the protein-protein interaction level obtained in step (4-1) by the amount of the first protein contained in the test sample, can reduce the errors attributable to the amount and/or distribution of the first protein present in the test sample, thereby allowing for more accurate measurement of the activation level of the first protein.

The method provided by the present invention may further comprise a step of measuring the amount of the first protein in the test sample. The step of measuring the amount of the first protein in the test sample may be conducted prior to or simultaneously with step (4) or step (4-2).

The amount of the first protein may be measured using any typical method, exemplified by, but not limited to, an immunoblotting method (e.g., quantitative western blotting), and ELISA (enzyme-linked immunosorbent assay; direct assay, indirect assay, sandwich assay, etc.). In an embodiment, the first protein can be quantitatively measured by, for example, adding a marker-labeled antibody to a substrate having the first protein immobilized thereto and measuring a signal generated from the marker, but the quantitation is not limited thereto.

When two or more different first proteins and/or second proteins are used, the activation level measurement step may be performed for each of combinations of individual first and second proteins.

When two or more different second proteins (which may be downstream proteins) exist, a sum of PPI strength obtained for individual second proteins or a protein-protein interaction level (PPI score) obtained from the sum of PPI strength may be used to determine an activation level (activation score), or a sum of activation scores obtained for individual second proteins may be determined to be an activation level (activation score) for the two or more different second proteins.

When two or more different first proteins exist, a sum of PPI strength obtained for individual first proteins or a protein-protein interaction level (PPI score) obtained from the sum of PPI strength may be used to determine an activation level (activation score), or a sum of activation scores obtained for individual second proteins may be determined to be an activation level (activation score) for the two or more different first proteins.

In another embodiment, the obtained activation level may be normalized so that the protein-protein interaction level of the reference sample described below becomes 1, whereby the activation level of the test sample can be represented as a value relative to the activation value of the reference sample.

Step (5): Comparison with Reference Sample

In step (5), the result (protein-protein interaction level (PPI score) or activation level (activation score)) obtained in step (4), (4-1), or (4-2) is compared to that (protein-protein interaction level (PPI score) or activation level (activation score)) obtained in a reference sample.

The reference sample may be suitably selected according to the purpose of the invention.

For example, for a method for measuring (or identifying, determining, or analyzing) the activation of a signaling pathway in a cell or tissue or for providing information for activation measurement, the reference sample may include: (1) a normal cell; (2) a cell having a known (identified) activation level of a signaling pathway in which the first protein is involved (e.g., normal cell or cancer cell); and/or (3) a cell (e.g., normal cell or cancer cell) isolated from a subject having a known (identified) activation level of a signaling pathway in which a first protein is involved. In one embodiment, when the test sample includes a cancer cell isolated from a subject, the reference sample may include a normal cell from the same tissue or organ as the cancer cell.

As used herein, the term "normal cell" may mean any cell in a non-pathological state. The term "non-pathological state" means a non-diseased state or a state in which mutation, neoplasia, or disease with functional and/or morphological aberration has not been or cannot be caused. For example, a normal cell may be a cell free of a disease associated with a first protein or a disease which a test drug targets, and may be derived from the same or homologous subject or tissue as that from which a test sample is derived.

In a method for predicting responsiveness to a first-protein-targeting drug or for providing information for the prediction, the reference sample may include a normal cell or a cell known (identified) for responsiveness to the drug (e.g., cancer cell) or, when the test sample includes a cancer cell isolated from the subject, may include a normal cell from the same tissue or organ as that of the cancer cell.

In a method for selecting a subject suitable for use in the first-protein-targeting therapy or providing information for the selection, the reference sample may include a normal cell or a cell known (identified) for the effect of the first-protein-targeting therapy (e.g., cancer cell) or, when the test sample includes a cancer cell isolated from the subject, may include a normal cell from the same tissue or organ as that of the cancer cell.

In order to conduct step (5), the above methods may further comprise the following steps (1'), (2'), (3'), and (4'), or (1'), (2'), (3'), (4-1'), and (4-2') for the reference sample, before step (5):

(1') adding a test sample containing the first protein to a substrate having a substance on the surface thereon, said substance binding specifically to the surface thereof, to prepare a substrate having the first protein immobilized thereto;

(2') adding and reacting the prepared first-protein-immobilized substrate with a labeled second protein;

(3') measuring a signal from the reactant obtained in step (2') (measuring protein-protein interaction); and (4') dividing the measured signal by the amount of the first protein in the reference sample added in step (1') (measuring activation level)

(or (4-1) dividing the measured signal by the weight or concentration of the reference sample added in step (1') (protein-protein interaction level measurement step) and (4-2') dividing the result obtained in step (4-1) by the amount of the first protein in the test sample (measuring activation level)).

Details in each step are as described in each step for the test sample above.

Step (6)

The method provided according to the present invention may further comprise a step of identifying (determining) a matter of interest from the comparison result obtained in step (5) after step (5).

Below, a detailed explanation will be given for the step.

(i) Method for Measuring (Identifying, Determining, or Analyzing) the Activation of the Signaling Pathway in a Cell or Tissue or Providing Information for Activation Measurement Step (6) may comprise:

a step in which, when the protein-protein interaction level or activation level of the test sample measured in step (4) or (4-2) is higher than that measured in the reference sample, the degree of activation of the first protein-implicated signaling pathway in the test sample or a subject from which the test sample is derived is determined to be higher than that in a normal cell or that known (identified) for the reference sample;

a step in which, when the protein-protein interaction level or activation level of the test sample measured in step (4) or (4-2) is equivalent to that measured in the reference sample, the degree of activation of the first protein-implicated signaling pathway in the test sample or a subject from which the test sample is derived is determined to be equivalent to that in a normal cell or that known (identified) for the reference sample; and/or a step in which, when the protein-protein interaction level or activation level of the test sample measured in step (4) or (4-2) is lower than that measured in the reference sample, the degree of activation of the first protein-implicated signaling pathway in the test sample or a subject from which the test sample is derived is determined to be lower than that in a normal cell or that known (identified) for the reference sample.

(ii) Method for Predicting Responsiveness to Drug Targeting First Protein or for Providing Information for Prediction Here, step (6) may comprise:

a step in which, when the protein-protein interaction level or activation level of the test sample measured in step (4) or (4-2) is higher than that measured in the reference sample, the responsiveness to a first-protein-targeting drug in the test sample or a subject from which the test sample is derived is determined to be higher than that in the reference sample;

a step in which, when the protein-protein interaction level or activation level of the test sample measured in step (4) or (4-2) is equivalent to that measured in the reference sample, the responsiveness to a first-protein-targeting drug in the test sample or a subject from which the test sample is derived is determined to be equivalent to that in the reference sample; and/or a step in which, when the protein-protein interaction level or activation level of the test sample measured in step (4) or (4-2) is lower than that measured in the reference sample, the responsiveness to a first-protein-targeting drug in the test sample or a subject from which the test sample is derived is determined to be lower than that in the reference sample.

A reference sample may include a cell that shows a degree of responsiveness, required for a test subject, to a first-protein-targeting drug to examine whether the drug has a desired effect on the test sample or the test subject from which the test sample is derived, or a reference sample may be selected as a normal cell to examine whether the drug acts specifically on a disease related with the first protein other than the normal cell in the test sample or test subject.

For example, in a case where a cell having a degree of responsiveness, required for a test subject, to a first-protein-targeting drug is selected as the reference sample, step (6) may comprise a step of determining that the test sample or the subject from which the test sample is derived has an excellent responsiveness to the first-protein-targeting drug and/or the drug has an effect on the test sample or the subject from which the test sample is derived when the protein-protein interaction level or activation level of the test sample, measured in step (4) or (4-2), is at least equivalent to, for example, higher than, that measured in a reference sample.

The method for predicting responsiveness to a first-protein-targeting drug or providing information for prediction may further comprise a step of administering a first-protein-targeting drug to the subject when, in step (6), it is determined that the test sample or the subject from which the test sample is derived has an excellent responsiveness to the first-protein-targeting drug and/or the drug has an effect on the test sample or the subject from which the test sample is derived.

According to another aspect, a tailored personal therapeutic means suitable for an individual subject is provided. One embodiment provides a pharmaceutical composition comprising a first-protein-targeting drug as an effective ingredient for treatment of a disease related with the first protein in a subject which is determined in step (6) to show an excellent responsiveness to the first-protein-targeting drug and/or to allow the drug to exhibit an effect thereon. Provided according to another embodiment is the use of the first-protein-targeting drug in treatment of a first protein-related disease in a subject which is determined in step (6) to show an excellent responsiveness to the first-protein-targeting drug and/or to allow the drug to exhibit an effect therein.

(iii) Method for Selecting a Subject Suitable for First-Protein-Targeting Therapy or Providing Information for Selection The reference sample may include a normal cell or a cell known (identified) for an effect on a first-protein-targeting therapy (e.g., cancer cell) or, when the test sample includes a cancer cell isolated from the subject, may include a normal cell from the same tissue or organ as that of the cancer cell.

When the protein-protein interaction level or activation level of the test sample, measured in steps (4) or (4-2), is at least equivalent to, for example, higher than, that measured in the reference sample, step (6) may comprise a step of identifying (determining) the test sample or the subject from which the test sample is derived to be a patient suitable for use in first-protein-targeting therapy.

The term "first-protein-targeting therapy", as used herein, means treatment with and/or administration of a first-protein-targeting drug.

The reference sample may include a cell in which the first-protein-targeting therapy is effective.

The method for selecting a subject suitable for a first-protein-targeting therapy or for providing information for the selection may further comprise a step of conducting a first-protein-targeting therapy on the subject (for example, treatment with and/or administration of a first-protein-targeting drug) when the test sample or the subject from which the test sample is derived is identified (determined) to be a patient suitable for a first-protein-targeting therapy.

Provided according to another aspect is a personal therapeutic means tailored for an individual subject on the basis of the identification (determination). One embodiment provides a pharmaceutical composition comprising a first-protein-targeting drug as an effective ingredient for treatment of a disease related with the first protein in a subject which is determined in step (6) to be suitable for a first-protein-targeting therapy. Provided according to another embodiment is a method for treating a first protein-related disease, comprising a step of conducting a first-protein-targeting therapy (for example, treatment with and/or administration of a first-protein-targeting drug) on the subject which is identified in step (6) to be suitable for the first-protein-targeting therapy.

(iv) Method for Monitoring Effect of First-Protein-Targeting Therapy (Responsiveness of Drug Targeting First Protein) or for Providing Information for Monitoring The reference sample may include a normal cell or a cell known (identified) for an effect of a first-protein-targeting therapy (e.g., cancer cell) or, when the test sample includes a cancer cell isolated from the subject, may include a normal cell from the same tissue or organ as that of the cancer cell.

When the protein-protein interaction level or activation level of the test sample, measured in steps (4) or (4-2), is at least equivalent to, for example, higher than, that measured in the reference sample, step (6) may comprise a step of identifying (determining) that the first-protein-targeting therapy exerts an effect on the test sample or the subject from which the test sample is derived (for example, after administration of a first-protein-targeting drug, the subject administered therewith retains responsiveness to the drug or has no resistance to the drug).

The first-protein-targeting therapy may mean treatment with and/or administration of a first-protein-targeting drug.

The reference sample may include a cell for which the first-protein-targeting therapy is effective.

The method for monitoring an effect of a first-protein-targeting therapy or for providing information for the monitoring may include a step of continually conducting the first-protein-targeting therapy (for example, treatment with and/or administration of a first-protein-targeting drug) when the first-protein-targeting therapy is determined in step (6) to exert an effect in the test sample or the subject from which the test sample is derived, or may include a step of stopping the first-protein-targeting therapy in the subject and/or administering a different first-protein-targeting drug or conducting a different first-protein-targeting therapy when the first-protein-targeting therapy is determined in step (6) to have no effects on the test sample or the subject from which the test sample is derived (for example, decreased treatment effect (drug responsiveness), acquired resistance, etc.).

Another embodiment provides a method for screening a first protein as a therapy target suitable for application to a cell or tissue or a subject (individual patient) from which the cell or tissue is derived or for providing information for the screening, the method comprising a step of measuring protein-protein interaction between the first protein and a second protein, wherein the first protein is a protein involved in a signaling pathway in the cell or tissue and the second protein is a protein downstream of the first protein in the signaling pathway in the cell or tissue, and the step of measuring protein-protein interaction is conducted for two or more kinds of the first protein.

The method may comprise the steps of:
(1) adding a test sample containing the first protein to a substrate having on the surface thereof a substance binding specifically to the first protein to prepare a substrate having the first protein immobilized thereto;
(2) adding and reacting the prepared substrate having the first protein immobilized thereto with a labeled second protein;
(3) measuring a signal from the reactant obtained in step (2) (measuring protein-protein interaction); and
(4) obtaining a signal value per unit amount of the first protein included in the test sample added in step (1) by means of the signal measured in step (3) (measuring an activation level); or
(4-1) obtaining a signal value per unit amount of the test sample added in step (1) by means of the signal measured in step (3) (measuring a protein-protein interaction level) and (4-2) obtaining a signal value per unit amount of the first protein contained in the test sample by means of the signal value per unit amount of the test sample, obtained in step (4-1); and
(5) comparing the result obtained in step (4) or (4-2) between two or more first proteins.

In this context, two or more different proteins that are involved in a signaling pathway in a cell or tissue are used as the first protein.

Steps (1), (2), (3), and (4) or steps (1), (2), (3), (4-1), and (4-2) are conducted for each of the two or more different first proteins.

The comparing step (5) may be set forth to compare respective results obtained for two or more different first proteins.

The method may further comprise a step (6) of selecting a first protein having a high protein-protein interaction level or activation level as a therapy target for the test sample or the subject from which the test sample is derived or selecting the first-protein-targeting drug as a drug candidate for treatment of the test sample or the subject from which the test sample is derived, based on the result of the composition in step (5).

The steps (1) to (6) and the terms such as "first protein", "second protein", etc. are as described above.

Provided according to another embodiment is a method for screening a first-protein-targeting drug candidate or for identifying the efficacy of a first-protein-targeting drug candidate, the method comprising a step of measuring protein-protein interaction between the first protein and a second protein, wherein the first protein is a protein involved in a signaling pathway in a cell or tissue and the second protein is a protein downstream of the first protein in the signaling pathway in the cell or tissue, and the step of measuring protein-protein interaction is conducted prior to or subsequent to treatment with a candidate substance.

The method may include the steps of:
treating (e.g. contacting) a test sample with a candidate compound; and
conducting the following steps (1), (2), (3), and (5) or steps (1), (2), (3), (4), and (5), or the following steps (1), (2), (3), (4-1), and (5) or steps (1), (2), (3), (4-1), (4-2), and (5) on each of the test samples that has or has not been treated with the candidate compound:
(1) adding a test sample containing the first protein to a substrate having on the surface thereof a substance binding specifically to the first protein to prepare a substrate having the first protein immobilized thereto;
(2) adding and reacting the prepared substrate having the first protein immobilized thereto with a labeled second protein;
(3) measuring a signal from the reactant obtained in step (2) (measuring protein-protein interaction); and
(4) obtaining a signal value per unit amount of the first protein included in the test sample added in step (1) by means of the signal measured in step (3) (measuring an activation level); or
(4-1) obtaining a signal value per unit amount of the test sample added in step (1) by means of the signal measured in step (3) (measuring a protein-protein interaction level), and (4-2) obtaining a signal value per unit amount of the first protein contained in the test sample by means of the signal value per unit amount of the test sample obtained in step (4-1); and
(5) comparing the respective results obtained in steps (3), (4), (4-1), or (4-2) for test samples which have and have not been treated with a candidate compound.

The term "test samples which have and have not been treated with a candidate compound" means respective test samples before and after treatment with a candidate compound or an aliquot of a test sample that has been treated with a candidate compound and another aliquot of the test sample which has not been treated with the candidate compound, respectively.

As a result of the comparison in step (5), when the protein-protein interaction level or activation level of the test sample treated with the candidate compound is higher than that of the non-treated test sample, the candidate compound may be selected as a first-protein-targeting drug candidate or may be identified to have an effect as a first-protein-targeting drug.

Therefore, the method for screening a first-protein-targeting drug candidate or for identifying the efficacy of a first-protein-targeting drug candidate may further comprise, after step (5), a step (6) of selecting the candidate compound as a first-protein-targeting drug candidate or of identifying the candidate compound to have an effect as a first-protein-targeting drug when the protein-protein interaction level or activation level of the test sample treated with the candidate compound is found to be higher than that of the non-treated test sample as a result of the comparison in step (5).

The candidate compound may be selected from all biocompatible materials that are available as target compounds of a first compound, for example, from the group consisting of small molecular chemicals, proteins (e.g., antibodies, antibody fragments, analogs thereof, etc.), peptides, nucleic acids (e.g., DNA, RNA (i.e., siRNA, microRNA, shRNA, etc.), and PNA (peptide nucleic acid), aptamers, etc.), plant extracts, animal extracts, and cell extracts, but is not limited thereto.

The test sample may be a cell (e.g., cell lysate, etc.) or tissue (e.g., tissue lysate) in which a first protein is overexpressed and/or (over)activated or an isolated cell (e.g., cell lysate, etc.) or tissue (e.g., tissue lysate) pertaining to a disease related with a first protein or a target disease to which the first-protein-targeting drug to be screened will be applied. In one embodiment, the test sample may be an established strain or a cell or tissue separated from a patient having the disease (e.g., cancer). For example, the test sample may be an established cancer cell strain or a cell or tissue isolated from a cancer patient (the cancer may be related with overexpression and/or (over)activation of the first protein).

The steps (1) to (6) may be performed in vitro.

The steps (1) to (6) and the terms such as "first protein", "second protein", etc. are as described above.

The method for screening a first-protein-targeting drug candidate may be usefully applied to the efficacy evaluation (or identification or assay) of a drug candidate in the development of a new first-protein-targeting drug.

The method may further comprise a step (6) of selecting the candidate compound as a first-protein-targeting drug candidate when the protein-protein interaction level or activation level of the test sample treated with the candidate compound is higher than that of the non-treated test sample.

The candidate compound may be selected from all biocompatible materials that are available as target compounds of a first compound, for example, from the group consisting of small molecular chemicals, proteins (e.g., antibodies, antibody fragments, analogs thereof, etc.), peptides, nucleic acids (e.g., DNA, RNA (i.e., siRNA, microRNA, shRNA, etc.), PNA (peptide nucleic acid), aptamers, etc.), plant extracts, animal extracts, and cell extracts, but is not limited thereto.

The test sample may be a cell (e.g., cell lysate, etc.) or tissue (e.g., tissue lysate) in which a first protein is overexpressed and/or (over)activated or an isolated cell (e.g., cell lysate, etc.) or tissue (e.g., tissue lysate) pertaining to a disease related with a first protein or a target disease to which the first-protein-targeting drug to be screened will be applied. In one embodiment, the test sample may be an established strain or a cell or tissue separated from a patient with the disease (e.g., cancer). For example, the test sample may be an established cancer cell strain or a cell or tissue isolated from a cancer patient (the cancer may be related with the overexpression and/or (over)activation of the first protein.

The steps (1) to (6) and the terms such as "first protein", "second protein", etc. are as described above.

The method for screening a first-protein-targeting drug candidate may be usefully applied to the efficacy evaluation (or identification or assay) of a drug candidate in the development of a new first-protein-targeting drug.

Another embodiment provides a method for selecting a target of a parallel therapy to be used in combination with the first-protein-targeting therapy or providing information for selection or a method for screening a parallel drug to be used in combination with a first-protein-targeting drug or for information for the screening, the method comprising a step of measuring protein-protein interaction between the first protein and a second protein, wherein the first protein is a protein that is involved in a signaling pathway in a cell or tissue and the second protein is at least one selected from proteins downstream of the first protein in the signaling pathway in the cell or tissue.

The method may comprise:
(1) adding a test sample containing the first protein to a substrate having on the surface thereof a substance binding specifically to the first protein to prepare a substrate having the first protein immobilized thereto;
(2) adding and reacting the prepared substrate having the first protein immobilized thereto with a labeled second protein;
(3) measuring a signal from the reactant obtained in step (2) (measuring protein-protein interaction); and
(4) obtaining a signal value per unit amount of the first protein included in the test sample added in step (1) by means of the signal measured in step (3) (measuring an activation level); or
(4-1) obtaining a signal value per unit amount of the test sample added in step (1) by means of the signal measured in step (3) (measuring a protein-protein interaction level) and (4-2) obtaining a signal value per unit amount of the first protein contained in the test sample by means of the signal value per unit amount of the test sample, obtained in step (4-1); and
(5) comparing the results obtained in step (3), (4), (4-1), or (4-2).

The comparing step (5) may be carried out by:
(a) comparing a result obtained for the test sample in step (4) or (4-2) with that obtained for a reference sample (in this case, the reference is as described above, and the method may further comprise the foregoing steps (1'), (2'), (3'), and (4') or (1'), (2'), (3'), (4-1'), and (4-2') described for the reference sample) or
(b) comparing results obtained for two or more different second proteins in step (4) or (4-2).

As a result of the comparison in step (5),
(a) when the protein-protein interaction level or activation level obtained for the test sample in step (4) or (4-2) is higher than that obtained for the reference sample, the second protein may be selected as a target of a parallel therapy to be used in combination with the first-protein-targeting therapy, or a drug targeting the second protein may be selected as a drug to be administered in combination with the first-protein-targeting drug;
(b) a second protein which shows a higher protein-protein interaction level or activation level obtained in step (4) or (4-2) than any other of the two or more different second proteins may be selected as a target of a parallel therapy to be used in combination with the first-protein-targeting therapy, or a drug targeting the second protein may be selected as a drug for use in co-administration with the first-protein-targeting drug.

Therefore, the method for selecting a target of a parallel therapy to be used in combination with the first-protein-targeting therapy (or the method for providing information for the selection) or the method for screening a parallel drug to be used in combination with a first-protein-targeting drug (the method for information for the screening) may further comprise, after step (5), a step of:
(6-1) selecting the second protein as a target of a parallel therapy to be used in combination with the first-protein-targeting therapy or selecting a second protein-targeting drug as a drug to be administered in combination with the first-protein-targeting drug when the protein-protein interaction level or activation level obtained for the test sample in step (4) or (4-2) is higher than that obtained for the reference sample;

(6-2) selecting a second protein which shows a higher protein-protein interaction level or activation level obtained in step (4) or (4-2) than any other of the two or more different second proteins as a target of a parallel therapy to be used in combination with the first-protein-targeting therapy or selecting a drug targeting the second protein as a drug for use in co-administration with the first-protein-targeting drug.

Provided according to another aspect is a parallel therapeutic means based on the determination. An embodiment provides a pharmaceutical composition for treatment of a first protein-related disease, comprising a first-protein-targeting drug and a drug targeting (for example, inhibiting) the second protein selected as a target of a parallel therapy in step (6-1) or (6-2), wherein the drugs are administered in combination. The pharmaceutical composition may be used to treat a first protein-related disease in the test sample or a subject from which the test sample is derived, through combined administration. Another embodiment provides a method for treatment of a first protein-related disease, comprising a step of conducting a first-protein-targeting therapy (e.g., administration of a first-protein-targeting drug) and a therapy targeting the second protein selected as a target of a parallel therapy in step (6-1) or (6-2) (e.g., administration of a drug targeting (inhibiting) the second protein) simultaneously or in series, irrespective of the order thereof, on a subject in need of treatment for the first protein-related disease. The patient may be the test sample entity or a subject from which the test sample is derived.

As used herein, the expression "targeting a first protein" means promoting or inhibiting the activity of a first protein, for example, inhibiting the activity of a first protein. The inhibition of the activity of a first protein may be the reduction or elimination of an intrinsic function of the first protein, for example, a signal transduction function intrinsic to a cell and/or a tissue, by binding and/or structurally modifying the first protein.

The term "drug", as used herein, means any substance that exhibits a pharmacological effect, for example at least one selected from the group consisting of small-molecule compounds, antibodies (e.g., antibodies, antibody fragments, analogs thereof, etc.), peptides, nucleic acid molecules (e.g., DNA, RNA (i.e., siRNA, microRNA, shRNA, etc.), PNA (peptide nucleic acid), aptamers, etc.), plant extracts, animal extracts, and cell extracts.

As used herein, the term "first-protein-targeting drug" means any substance inhibitory of the activity of a first protein, for example at least one selected from the group consisting of small-molecule compounds, antibodies (e.g., antibodies, antibody fragments, analogs thereof, etc.), peptides, nucleic acid molecules (e.g., DNA, RNA (i.e., small interfering RNA (siRNA), microRNA, small hairpin RNA (shRNA), etc.), PNA (peptide nucleic acid), aptamers, etc.), plant extracts, animal extracts, and cell extracts. In greater detail, "first-protein-targeting drug" is intended to refer to any substance that binds to, degrades, and/or structurally modifies a first protein to reduce or eliminate an intrinsic function thereof, for example, a signal transduction function intrinsic to a cell and/or a tissue, for example, at least one selected from the group consisting of small-molecule compounds, antibodies (e.g., antibodies, antibody fragments, analogs thereof, etc.), peptides, nucleic acid molecules (e.g., DNA, RNA (i.e., siRNA, microRNA, shRNA, etc.), PNA (peptide nucleic acid), aptamers, etc.), plant extracts, animal extracts, and cell extracts, which inhibit the activity of the first protein.

In an embodiment, the "first-protein-targeting drug" may refer to a first-protein-targeting therapeutic agent, for example, a first-protein-targeting inhibitor. In an embodiment, the first-protein-targeting drug may be at least one selected from the group consisting of EGFR-targeted therapeutic agents (cetuximab, gefitinib, erlotinib, afatinib, osimertinib (AZD9291), various anti-EGFR antibodies, etc.), MET-targeted therapeutic agents (various anti-MET antibodies, crizotinib, cabozantinib, etc.), HER2-targeted therapeutic agents (trastuzumab, pertuzumab, lapatinib, etc.), HER3-targeted therapeutic agents (various anti-HER3 antibodies, etc.), FGFR(1, 2)-targeted therapeutic agents (lenvatinib, nintedanib, regorafenib, etc.), VEGFR(1, 2, 3)-targeted therapeutic agents (bevacizumab, axitinib, lenvatinib, etc.), PDGFR-targeted therapeutic agents (axitinib, gefitinib, imatinib, etc.), IGF1R-targeted therapeutic agents (ceritinib, etc.), c-KIT-targeted therapeutic agents (axitinib, cabozantinib, dasatinib, etc.), RET-targeted therapeutic agents (vandetanib, etc.), BRAF-targeted therapeutic agents (vemurafenib, dabrafenib, etc.), MEK-targeted therapeutic agents (trametinib, etc.), Src-targeted therapeutic agents (bosutinib, dasatinib, ponatinib, vandetanib, etc.), PI3K-targeted therapeutic agents (crizotinib, cabozantinib, etc.), CDK(4, 6)-targeted therapeutic agents (palbociclib, sorafenib, etc.), ROS1-targeted therapeutic agents (ceritinib, crizotinib, etc.), ALK-targeted therapeutic agents (ceritinib, crizotinib, etc.), BCR-Abl1-targeted therapeutic agents (bosutinib, dasatinib, imatinib, nilotinib, etc.), AR-targeted therapeutic agents (abiraterone, enzalutamide, etc.), CTLA4-targeted therapeutic agents (ipilimumab, tremelimumab, etc.), and PD-1-targeted therapeutic agents (nivolumab, etc.), but are not limited thereto.

As used herein, the term "first-protein-targeting therapy" is intended to encompass all medical and/or pharmaceutical behaviors inhibitory of the activity of a first protein, and, for example, may include administering and/or prescribing such a drug inhibiting the activity of a first protein as is described above to a subject in need of inhibiting the activity of the first protein. In greater detail, the "first-protein-targeting therapy" may include administration and/or prescription of a drug that binds to, degrades, and/or structurally modifies a first protein to reduce or eliminate an intrinsic function, for example, a signal transduction function intrinsic to a cell and/or a tissue to a subject in need thereof.

The administration may be carried out via an oral or parenteral route. The parenteral administration may be performed by intravenous injection, subcutaneous injection, intramuscular injection, intraperitoneal injection, intradermal administration, intraregional topical administration, intranasal administration, intrapulmonary administration, or intrarectal administration.

Examples of the individual, patient, or subject may include all mammals, for example, primates such as humans, monkeys, etc., rodents such as mice, rats, etc., and the like, and may be a patient with a first protein-related disease. The first-protein-related disease may be a disease associated with the overexpression of a first protein or with the activation of a signaling pathway in which a first protein is involved in a cell or tissue, for example, cancer, inflammation, or immune disease. In an embodiment, the individual, patient, or subject may be a cancer patient.

The cancer may be selected from among all solid cancers and blood cancers, and may be a cancer associated with, for example, the overexpression of the first protein or the activation of an intracellular or intratissue signaling pathway in which the first protein is involved. For example, the cancer may be at least one selected from the group consisting of squamous cell carcinoma, small-cell lung cancer, adenocarcinoma of the lungs, squamous cell carcinoma of the lungs, skin cancer, skin or intraocular melanoma, rectal cancer, perianal cancer, esophageal cancer, small intestine cancer, endocrine cancer, parathyroid cancer, adrenal cancer, soft tissue sarcoma, urethral cancer, chronic or acute leukemia, lymphoma, gastrointestinal cancer, pancreatic cancer, glioblastoma, cervical cancer, ovarian cancer, bladder cancer, breast cancer, colon cancer, colorectal cancer, endometrial cancer or uterine cancer, salivary gland cancer, kidney cancer, prostate cancer, vulvar cancer, thyroid cancer, head and neck cancer, and brain cancer, but is not limited thereto. The cancer may include metastatic cancer as well as primary cancer. In addition, the cancer may be a cancer that has or acquires resistance to conventional anticancer therapy.

As used herein, the term "responsiveness to a drug" means the degree of the effect that the drug exhibits in a drug-administered individual.

As used herein, the term "effect" refers to a medical and/or pharmaceutical effect that a drug or therapy is intended to achieve in a treated subject and may mean prevention and/or treatment of a disease in a subject and/or reduction and/or alleviation of a disease symptom. For example, when the drug, the treatment, and the subject are an anticancer agent, an anticancer therapy, and a cancer patient, respectively, the effect is an anticancer effect (preventive and/or therapeutic effect on cancer). The anticancer effect may include effects of preventing migration, invasion, and/or metastasis of cancer, suppressing deterioration of cancer, and/or reducing or eliminating resistance of cancer as well as inhibiting the growth of cancer cells.

In another embodiment, a device for measuring protein-protein interaction is provided for use in the method for measuring activation of a signaling pathway in a cell or tissue, the method for predicting responsiveness to a first-protein-targeting drug, the method for monitoring responsiveness to a first-protein-targeting drug, the method for selecting an individual suitable for a first-protein-targeting therapy, and/or the method for screening a drug, which are described above. The device for measuring protein-protein interaction is applicable as a device for measuring activation of a signaling pathway in a tissue, a device for predicting and/or monitoring responsiveness to a first-protein-targeting drug, and/or a device for selecting an individual suitable for a first-protein-targeting therapy and/or a device for identifying efficacy of a first-protein-targeting drug.

By being applied to a device for measuring activation of a signaling pathway in a tissue, a device for predicting and/or monitoring responsiveness to a first-protein-targeting drug, a device for selecting an individual suitable for a first-protein-targeting therapy, and/or a device for identifying the efficacy of a first-protein-targeting drug, the device for measuring protein-protein interaction has the advantage of being able to accurately and effectively observe, analyze, detect, and/or measure inter-biomolecular interaction in a small amount of a sample. The device for measuring protein-protein interaction or an analysis method using the same can be usefully and effectively applied to a very small amount of a sample, such as a biopsy (e.g., needle biopsy) sample. In addition, the method for measuring protein-protein interaction or the analysis method allows interaction among a variety of biomolecules (e.g., proteins, nucleic acids, etc.) to be observed, analyzed, detected, and/or measured accurately and effectively in a small amount of a sample.

The device for measuring protein-protein interaction may comprise:
a multi-well including therein a substance for capturing a first protein by binding specifically to the first protein; and
a signal detection means.

The protein-protein interaction measuring device may further comprise a protein (second protein) interacting with the first protein (for example, participating in a downstream pathway of the signaling pathway in which the first protein is involved in a cell or tissue). In one embodiment, the second protein may be labeled with a marker that generates a detectable signal (coupled with a marker, for example, chemically (e.g., covalently or non-covalently), recombinantly, or physically) or may have a tag attached thereto, the tag being capable of being coupled to a marker. In addition, the protein-protein interaction measuring device may further comprise a probe binding to the first protein and a labeling substance capable of being coupled to the probe in order to normalize a signal value measured by the signal detection means to the level of the first protein. The probe binding to the first protein may be a biomolecule (e.g., antibody) that binds to the first protein at a site different from that for the capturing substance contained in the aforementioned multi-wells. The labeling substance may be coupled to a marker that generates a detectable signal (coupled to a marker, for example, chemically (e.g., covalently or non-covalently)) and may be a biomolecule (e.g., antibody) capable of being coupled to the probe binding to the first protein (see FIG. 6).

The multi-well included in the protein-protein interaction measuring device according to an embodiment may have a structure that comprises multiple tubes, each having an open side, or non-through-type multiple holes formed distant from each other in a support plate (e.g., recesses formed in a support plate) wherein the one side-open tube or the non-through-type hole is defined as a well. In the structure, a straight alignment in which two or more wells are arranged in a first direction may exist, or two or more straight alignments may be arranged in a second direction crossing the first direction (lattice structure) (see FIG. 30). Herein, the multi-well may comprise: a sample input part positioned at the open side of the tube or the non-through-type hole; a reaction part inside the tube or the non-through-type hole where protein-protein interaction (e.g., interaction between a first protein and a second protein) occurs; and a first protein-capturing part (or substrate) of which the inner wall is in contact with the inside of the tube or the non-through-type hole and has a substance for capturing the first protein (e.g., a substance specifically binding to the first protein (i.e., antibody)) immobilized on a part of the surface thereof or allows the substance to be immobilized on a part of the surface thereof. In an embodiment, the multi-well may comprise at least one well including a reaction part where interaction between a first protein and a second protein occurs (reaction part of first and second proteins: first reaction part) and at least one well including a reaction part where the first protein and a probe binding to the first protein are coupled to each other (first protein probing part:second reaction part). The probe binding to the first protein is as described above. The first protein probing part can be used to measure the level of the first protein in a test sample to normalize a signal value measured in the signal detection means included in the device to the level of the first protein.

In one embodiment, the multi-well may comprise: a support plate extending in a first direction; multiple receiving parts arranged at a distance from each other in the first direction; through-holes formed respectively in the multiple receiving parts and penetrating the receiving parts in a second direction perpendicular to the first direction; and a substrate arranged on the multiple receiving parts to cover one end of each of the through-holes and having a surface-treated side facing the through-holes (see FIG. 27). In this context, spaces formed by the spaced through-holes and the substrate covering one end of each of the through-holes can be defined as wells. As described above, the multi-well may mean a structure in which two or more wells are arranged in a first direction (straight structure) or in first and second directions perpendicular to each other (lattice structure).

The multi-well may comprise multiple wells, each containing a substance for capturing one or two different first proteins. When the multi-well comprises a substance binding specifically to two or more different first proteins, the wells that contain respective substances binding specifically to two or more different first proteins may be arranged to position substances binding to the different first proteins in the first direction or in the second direction perpendicular to the first direction.

One surface of the first-protein-capturing part or the substrate may be treated with any compound that has a functional group capable of immobilizing a first-protein-capturing substance (a substance capable of specifically binding to the first protein, that is, an antibody, etc.) and, for example, may be treated with a compound having at least one functional group selected from the group consisting of an aldehyde group, a carboxyl group, and an amine group. In one embodiment, the compound having a functional group selected from the group consisting of an aldehyde group, a carboxyl group, and an amine group may be at least one selected from the group consisting of biotin, biotinylated bovine serum albumin, polyethylene glycol (PEG), biotinylated PEG (PEG-biotin), and polysorbate (e.g., Tween20), but is not limited thereto. The surface-treated substrate may be further treated (e.g., coated) with at least one selected from the group consisting of neutravidin, streptavidin, and avidin.

An adhesive may be interposed between the substrate and the receiving part facing each other.

The adhesive may comprise epoxy (e.g., UV epoxy).

The multi-well may comprise an adhesive surrounding the substrate and the receiving part in the vicinity of a region in which the substrate and the receiving part are in contact with each other.

This adhesive may comprise epoxy.

The multiple support plates may be arranged at a distance from each other in a third direction perpendicular to both the first and the second direction.

The through-hole may have a circular cross section.

The receiving part may be in a form protruding from the support plate.

The receiving part and the support plate may be integrated with each other.

The receiving part and the support plate may comprise acryl.

The substrate may comprise glass.

The signal detection means may be any signal detection means that is typically used according to the signals generated by the marker that is used. For example, the signal detection means may comprise a signal stimulation part and a signal detection part. Further, a signal analysis part for analyzing (e.g., quantitating or imaging) measured signals may be included. In one embodiment, signal stimulation, signal detection, and signal analysis may be conducted at respective regions. Alternatively, at least two of signal stimulation, detection, and analysis may be conducted simultaneously or consecutively in one region. In one embodiment, when the marker is a fluorescent material, the signal detection means may be selected from all means that can generate and detect a fluorescent signal, and may comprise, for example, a fluorescent signal stimulation part (e.g., light source) and a fluorescent signal detection part, and optionally a fluorescent signal analysis part. In one embodiment, the signal detection means may comprise a Total Internal Reflection Fluorescence (TIRF) microscope or a confocal microscope (light source and fluorescent signal detection) and optionally a fluorescence camera, for example, an electron-multiplying charge-coupled device (EMCCD) camera or a complementary metal oxide semiconductor (CMOS) camera to provide a light source and image and/or quantitate fluorescent signals. The wavelength and strength of the light source and the measurement conditions of a fluorescence camera (e.g., exposure time per frame, laser power, camera gain value, total frame numbers, etc.) are as described above.

The first protein, the substrate, the substance binding specifically to the first protein, the second protein, the marker, and the signal detection means according to the marker are as described above.

The protein-protein interaction measuring device is illustrated in FIGS. 27 to 30, but is not limited thereto.

A method for fabricating a protein-protein interaction measuring device according to one embodiment comprises the steps of: preparing a support plate that extends in a first direction and on which multiple receiving parts are arranged at a distance from each other in the first direction; and attaching a surface-treated substrate onto the support plate, wherein each of the multiple receiving parts has a through-hole penetrating the receiving parts in a second direction perpendicular to the first direction and the surface-treated substrate covers the one end of the through hole in such a way that the treated surface faces the through hole.

The surface treatment of the substrate is as described above, and may be conducted by treatment with a mixture of polyethylene glycol (PEG) and biotin in one embodiment.

The PEG and biotin may be mixed at a weight ratio of 100:1 to 100:3 (PEG:biotin).

The surface-treated substrate may be further coated with at least one selected from the group consisting of neutravidin, streptavidin, and avidin.

The step of attaching the substrate onto the support plate may comprise the steps of: applying UV epoxy to the substrate-facing upper surface of the receiving part; covering the receiving part with the substrate; and radiating UV light toward the receiving part from the substrate.

In the step of radiating UV light, a mask may be used to prevent the UV light from passing through substrate regions corresponding to the through holes.

The step of attaching the substrate onto the support plate may comprise the steps of covering the receiving part with the substrate and applying a sealing member to the vicinity of a region in which the substrate and the receiving part are in contact with each other so as to surround the substrate and the receiving part.

The sealing member may comprise epoxy.

The protein-protein interaction measuring device provided according to the present invention may be usefully applied to the observation, analysis, detection, and/or measurement of interaction (e.g., protein-protein interaction, etc.) between various biomolecules (e.g., proteins, nucleic acids, etc.).

Contemplated according to another embodiment is therefore a method for analyzing interaction (e.g., protein-protein interaction) between biomolecules, comprising a step of contacting a sample containing a biomolecule (e.g., first protein) to be analyzed with the protein-protein interaction measuring device or the multi-well in the device. The analysis method may further comprise a step of measuring a signal generated in the sample, after the contacting step. In this regard, the signal may be suitably selected from all signals (e.g., fluorescence, luminescence, etc.) that are typically used for biomolecule analysis, and the signal analysis may be conducted using any method that is typically used according to the kind of the signal that is used. The biomolecule may be at least one selected from the group consisting of proteins, nucleic acids, and cells, all being isolated from an organism, and may be, for example, a protein. In the case where the biomolecule is a protein, the multi-well included in the protein-protein interaction measuring device for use in the analysis of protein-protein interaction has a molecule (e.g., antibody) immobilized on the surface thereof, the molecule binding specifically to one of the proteins to be analyzed.

Hereinafter, embodiments of the present invention will be described in more detail with reference to the accompanying drawings so as to allow those skilled in the art to easily implement the present invention. The present disclosure may be implemented in various different forms and is not limited to embodiments described herein. Further, parts irrelevant to the present invention are omitted in the drawings to make the present invention clear and the same reference numerals are designated to the same or similar components throughout the specification.

Because the size and thickness of each configuration shown in the drawings are arbitrarily shown for better understanding and ease of description, the present invention is not limited thereto, and the thickness of portions and regions are exaggerated for clarity. In the drawings, the thickness of layers and regions may be exaggerated for clarity. It will be understood that when an element such as a layer, film, region, or substrate is referred to being "on" another element, it can be "directly on" the other element or intervening elements may also be present.

Throughout the specification, unless explicitly described to the contrary, the word "comprise" and variations such as "comprises" or "comprising" will be understood to imply the inclusion of stated elements but not the exclusion of any other elements.

Below, the multi-well included in the protein-protein interaction measuring device according to one embodiment of the present invention will be described in an illustrative manner in conjunction with FIG. 27, but is not limited to the structure shown therein.

FIG. 27 is a schematic perspective view of a multi-well included in a protein-protein interaction measuring device according to an embodiment. Referring to FIG. 27, an example of the multi-well included in the protein-protein interaction measuring device comprises support plates 155, 165, and 175, multiple receiving parts 153, through holes 151, and a substrate 300. In this embodiment, a through-hole 151 is formed in each of the multiple receiving parts 153 formed on the support plates 155, 165, and 175 and one end of the through-hole 151 is covered with a substrate 300 surface treated with biotin.

The support plates 155, 165, and 175 are each a planar member extending in a first direction (X-axis direction). Multiple support plates 155, 165, and 175 may be arranged at a predetermined distance from each other in a third direction (Y-axis direction). In this embodiment, three plates 155, 165, and 175 are illustrated, but only one support plate may be used, or four or more support plates may be arranged.

Opposite ends of the multiple plates 155, 165, and 175 may be fixedly engaged to a couple of support bars 110 and 130, such that the multiple plates 155, 165, and 175 can be fixed at a predetermined distance from each other.

On each of the multiple plates 155, 165, and 175, multiple receiving parts 153 may be arranged. The multiple receiving parts 153 may be arranged at a distance from each other on each of the plates 155, 165, and 175 in the first direction (X-axis direction). In detail, multiple receiving parts 153 may be arranged at a predetermined distance in the first direction (X-axis direction) on plates 155, 165, and 175.

The multiple receiving parts 153 may be in a protruding form. For example, the multiple receiving parts 153 may be formed to protrude out of the plates 155, 165, and 175. As illustrated in FIG. 1, the multiple receiving parts 153 may be in a hexahedral arrangement on the plates 155, 165, and 175. However, the multiple receiving parts 153 are not limited to the form, but may be arranged with various morphologies given thereto.

In the embodiment, the plates 155, 165, and 175 may be integrated with the multiple receiving parts 153. For example, the plates 155, 165, and 175 and the multiple receiving parts 153 may be obtained by processing one planar member with a laser.

Each of the multiple receiving parts 153 may have a through-hole 151 penetrating therethrough. The through-hole 151 may be formed in a second direction (Z-axis direction). In detail, the through-hole 151 may have a form penetrating in the top-down direction as shown in FIG. 1. However, the through-hole 151 may be closed by a substrate 300 at one end thereof. The through-hole 151 may have a circular cross section.

As described above, the receiving part 153 may be in the form of a cylindrical well when one end of the through-hole 151 is closed. The multiple receiving parts 153 can receive a sample, for example, a protein, therein thanks to the through-hole 151 formed in each of the multiple receiving parts 153.

In one embodiment, multiple receiving parts 153 are formed on each of multiple plates 155, 165, and 175 and have respective through-holes 151 formed therein to construct a multi-well structure. The number of wells may be adjusted depending on the sizes of the substrate and the numbers of support plates and/or receiving parts. Although no particular limitations are imposed on the size thereof, each well may have a diameter of about 2 mm or greater, for example, 2 to 10 mm, 2 to 8 mm, 2 to 6 mm, 2 to 5 mm, 2 to 4 mm, or about 3 mm and a depth at least about ½-fold greater than the diameter, for example, ½- to 5-fold, ½- to 3-fold, ½- to 2-fold, 1- to 5-fold, 1- to 3-fold, or 1- to 2-fold greater than the diameter, so as to make it easy to detect interaction between biomolecules. The distance between adjacent wells should be about 5 mm or greater with reference to the distance between two well centers, and may be determined in consideration of the diameter of the well under the condition where the distance between two well centers should be about 5 mm or greater in order to prevent the leakage and/or interference of response signals.

Meanwhile, a substrate 300 may be disposed on the multiple receiving parts 153. The substrate 300 may be made of a transparent material. For example, the substrate 300 may be a glass substrate.

The substrate 300 may cover one end of the through-hole 151 in each of the multiple receiving parts 153. In this condition, one end of the through-hole 151 is closed by the substrate 300 so that the receiving part 153 may have a well form, as described above.

In one embodiment, the substrate 300 and the receiving part 153 may be attached to each other via an adhesive (E). The adhesive (E) may be epoxy.

The adhesive (E) is applied to the vicinity of a region at which the substrate 300 and the receiving part 153 are in contact with each other, surrounding the substrate 300 and the receiving part 153 (for example, the adhesive (E) is applied to the outer rim of the receiving part 153 so as not to penetrate into the through-hole). In the course of combining the receiving part 153 and the substrate 300, the substrate 300 is disposed on the receiving part 153 to realize contact therebetween and the adhesive (E) is applied to surround the substrate 300 and the receiving part 153.

The adhesive (E) is applied in such a way to surround the substrate 300 and the receiving part 153 and thus can be prevented from infiltrating into the through-hole 151. In the case where the adhesive (E) is composed of epoxy as described above, the epoxy, if infiltrating into the through-hole 151, may come into contact with the sample received via the through-hole 151. If so, the sample such as a protein may react with the epoxy and thus may be non-specifically adsorbed. In the embodiment, hence, the sample received within the through-hole 151 can be prevented from coming into contact with the adhesive (E), such as epoxy, and from being modified.

In addition, because the receiving parts 153 are arranged apart from each other on the plates 155, 165, and 175, the adhesive (E) can be easily applied along the circumference of each of the receiving part 153.

In a modified embodiment, an adhesive (E) may be interposed between the receiving part 153 and the substrate 300. In this regard, the receiving part 153 and the substrate 300 may be coated with the adhesive (E) before they come into contact with each other. Then, the receiving part 153 and the substrate 300 may be brought into contact with each other and irradiated with UV to rapidly cure the adhesive. The adhesive (E) may be UV epoxy.

The adhesive (E) disposed between the receiving part 153 and the substrate 300 may not be present within the through-hole 151. That is, the adhesive (E) may be disposed at a position spaced by a certain gap (L1) from the inner surface of the through-hole. Because the adhesive (E) is positioned at a certain distance (L1) from the inner surface, the adhesive (E) can be brought into contact with the sample received within the through hole 151 to a lesser extent. Here, the substrate 300 have a thickness (H) of 0.17 mm-0.19 mm. The detailed process of attaching the receiving part 153 to the substrate 300 via the adhesive (E) will be explained in a method for fabricating a protein-protein interaction.

As described above, the adhesive (E) is applied in such a way to surround the substrate 300 and the receiving part 153, and thus can be prevented from infiltrating into the through-hole 151. When the adhesive (E) is composed of epoxy, the epoxy may come into contact with a sample received within the through-hole 151 if the epoxy infiltrates into the through-hole 151. If so, the sample such as proteins are reacted with the epoxy and modified. In this embodiment, a sample received within the through-hole 151 can be prevented from coming into contact with the adhesive (E) such as epoxy and from being modified.

The adhesive (E) disposed between the substrate 300 and the receiving part 153 is applied only to the receiving part 153 that comes into contact with the substrate 300 in order for the adhesive (E) to exist within the through-hole 151. UV is radiated on UV epoxy so that UV epoxy can be rapidly cured without infiltrating into the through-hole 151. Exposure to UV light can reduce the curing time of the UV epoxy.

In this embodiment, a mask 500 may be used upon exposure to UV light. The mask 500 can block the passage of UV light through the region of the substrate 300 corresponding to the through-hole 151. In greater detail, as shown in FIG. 26, the mask 500 has UV-blocking regions at positions corresponding to respective through-holes 151. These UV blocking regions can prevent UV light from being radiated on the regions of the substrate 300 corresponding to the through-holes 151.

As described above, the surface of the substrate 300 corresponding to the through-hole 151 may be treated with a mixture of polyethylene glycol (PEG) and biotin. For the substrate 300 which has been subjected to surface treatment with PEG and biotin and attached to the receiving part 153 by means of an adhesive (E), UV exposure may alter or damage the surface-treated substrate 300. If UV light is radiated on the substrate 300 disposed in the through-hole 151, the PEG or biotin is damaged by UV so that neutravidin cannot be immobilized on the substrate 300.

If neutravidin is not immobilized on the substrate 300, it is difficult to attach a particular biotin-antibody to the substrate 300. As a result, a particular antibody capable of coupling with the biotin-antibody cannot be captured. According to this modified embodiment, when UV light is used to rapidly cure UV epoxy, blockage of UV illumination on the regions of the substrate 300 corresponding to the respective through-holes 151 makes it easy to attach a sample, for example, a particular protein, received within the through-hole 151 to the surface of the substrate 300.

FIG. 31 shows results obtained from experiments in which UV illumination on the regions of the substrate 300 corresponding to respective through-holes 151 were blocked (Modified Example (A)) and were not blocked (Comparative Example (B)). Result values on the X-axis of FIG. 31 represent amounts of green fluorescent protein (GFP) detected on the surface of the substrate 300 in a comparative manner.

With reference to FIGS. 31(A) and 31(B), it was observed that a greater number of the antigen green fluorescent protein (GFP) was detected upon the blockage of UV illumination on the corresponding regions of the substrate 300, compared to the non-blockage thereof.

As illustrated in FIG. 31(A), the blockage of UV illumination on the regions of the substrate 300 allows the substrate 300 to be coated with PEG or biotin without damage thereto. Accordingly, neutravidin can also be immobilized on the substrate 300. As a result, the antibody (GFP antibody) is immobilized on the substrate 300 and can capture the antigen GFP.

In contrast, as shown in FIG. 31(B), UV illumination on the regions of the substrate 300 may cause damage to the polyethylene glycol (PEG) or biotin to be attached to the substrate 300. Accordingly, it is also difficult to immobilize neutravidin on the substrate 300. As a result, an antibody (GFP antibody) cannot be immobilized on the substrate 300 and cannot capture the antigen, either.

Provided according to another embodiment is a kit for measuring protein-protein interaction, the kit comprising a multi-well that includes a capturing substance binding specifically to a first protein as illustrated above. The protein-protein interaction measuring kit is applicable as a kit for measuring activation of a signaling pathway in a tissue, a kit for predicting and/or monitoring responsiveness to a firstprotein-targeting drug, a kit for selecting an individual suitable for a first-protein-targeting therapy, and/or a kit for screening efficacy of a first-protein-targeting drug.

The protein-protein interaction measuring device provided in the description has the advantage of being able to accurately and effectively observe, analyze, detect, and/or measure interaction between biomolecules even using a small amount of a sample. Therefore, the multi-well and the analysis method using the same can be usefully and effectively applied even to a very small amount of a biopsy (e.g., needle biopsy) sample.

Advantageous Effects

Making it possible to predict which reaction is elicited by a particular targeted therapy in individual patients or to select a targeted therapy suitable for individual patients, the methods provided in the description are expected to be useful as a platform for strategic development of tailored personal therapies.

DESCRIPTION OF DRAWINGS

FIG. 1 is a schematic diagram of a method for measuring a single molecular protein interaction.

FIG. 2 is a graph showing the result of confirming a target protein (first protein) immobilized on the substrate.

FIG. 3 is a fluorescence image showing protein interaction after injection of a fluorescence-labeled interacting protein (a second protein).

FIG. 4 is a graph showing quantified results of the number of PPI complexes observed in FIG. 3.

FIG. 5 is a graph showing changes in the number of PPI complexes according to the amount of injected cell lysate.

FIG. 6 is a schematic diagram showing the process of quantifying the first protein through a single-molecule sandwich ELISA.

FIG. 7 is a graph showing specificities measured by single-molecule sandwich ELISA.

FIG. 8 is a graph showing changes in the number of PPI complexes according to the types of cells (red ① vs light blue ③) and states (red ① vs black ②).

FIG. 9 is a graph showing changes in the number of PPI complexes for various target RTKs (first proteins) according to cell conditions.

FIG. 10 is a graph showing changes of PPI complex according to the EGFR mutation state and the ratio of EGFR activated per each cell based on the changes.

FIG. 11 shows the results of performing the same method for EGFR in FIG. 10 on HER2 and HER3.

FIG. 12 is a heatmap showing the result of measuring the interactions between EGFR, MET, HER2, HER3 (the first protein) and the downstream signal transduction protein (the second protein) in each cell line.

FIG. 13 is a graph quantitatively showing the results shown in FIG. 12 (left and middle), and a graph showing the reactivity results of AZD9291, which is a EGFR targeted anticancer drug (right).

FIG. 14 is a graph showing the correlation between the reactivity (left, y axis) and the activation score (left side, x axis) of the EGFR targeted anticancer drug (AZD9291), and the diversity (right) of the targeted anticancer response according to the genotype.

FIG. 15 is a heatmap showing the intensities of HER2 and HER3 signals in breast cancer cell lines.

FIG. 16 is a graph showing expression level of HER2 (upper) and HER3 (middle), which are conventional biomarkers for predicting the drug response of breast cancer cell line to trastuzumab, and inhibition level of cell growth (bottom) by trastuzumab.

FIG. 17 is a graph showing the correlation between the PPI score measured using the HER2 or HER3 signal and the drug response to trastuzumab (log $GI_{50}$).

FIG. 18 is a heatmap showing the PPI complex signal results of EGFR, MET, HER2, and HER3 with three downstream signal transduction proteins measured in the PDTX mouse model.

FIG. 19 is a graph showing EGFR expression level (upper) and activation score (bottom) calculated using the EGFR expression level in the PDTX mouse model.

FIG. 20 is a graph showing the results of measuring changes in tumor size by administering gefitinib to a PDTX mouse model.

FIG. 21 is a graph showing the correlation between tumor growth inhibition by gefitinib and EGFR activation score in the PDTX mouse model.

FIG. 22 is a graph showing EGFR PPI complex counts measured in tissues before and after being treated with gefitinib in a PDTX mouse model, respectively.

FIGS. 23a to 23i show drug responses to EGFR targeted inhibitor in a lung cancer PDTX model, wherein 23a is a schematic diagram illustrating a process for preparing a PDTX model, 23b is a graph showing tumor volume changes in PDTX model when treated with vehicle or indicated EGFR-specific inhibitor, wherein the tumor volume changes are measured in lung adenocarcinoma PDTXs (PDTX-A1 to A3) treated with osimertinib (5 mg per kg of weight daily) and lung squamous cell carcinoma (SQCC) PDTXs (PDTX-S1~S5) treated with gefitinib (50 mg per kg of weight daily) (population of each PDTX test group is 3 or more), 23c is a graph showing PPI complex counts (the number of PPI complexes) for the downstream signal proteins of the indicated receptor tyrosine kinases (RTK; EGFR, HER2, HER3 and MET), 23d is a graph showing the EGFR expression levels in 8 PDTX (A1 to A3 and S1 to S8) individuals, which are normalized to EGFR expression level in A549 cells (control group), 23e and 23f are graphs with a tumor growth inhibition ratio (%) on the y axis and values obtained by dividing EGFR PPI sum of PDTX models (e) and SQCC PDTX models (f) by the EGFR level on the x axis, 23g is a graph showing changes in PPI complex counts (the number of PPI complexes between EGFR and the second protein indicated on x axis) when treated with gefitinib every day for 15 days, 23h is a graph showing the degree of tumor growth in PDTX-S1 (n=2) with co-treatment of gefitinib and BKM120 for 15 days, compared to single treatment, and 23i is a graph in which x axis shows values obtained by dividing the PPI sum by the EGFR level in all 8 PDTX (A1 to A3 and S1 to S5) individuals, and y axis shows the tumor growth inhibition ration (Error bars: s.d.).

FIGS. 24a to 24d show examples of application of single-molecule co-IP and single-molecule immunolabeling to human tumor samples, wherein 24a shows human tumor tissues obtained by tumor resection surgery of two tumor patients (P1 and P2), 24b is a graph showing expression levels and PTM level (immunolabelling level) of 10 proteins measured by single-molecule immunolabeling, and PPI level of 10 protein-protein pairs obtained by performing single-molecule co-IP to each of the 10 samples using a high-efficiency single molecule imaging system, wherein PC9 cells (for EGFR), HCC827 cells (for MET), and SKBR3 cells (for HER2 and HER3) are respectively used as positive controls, 24c is a graph showing PPI complex counts for the indicated RTK in P1 and P2, and 24d is a graph showing changes in PPI complex counts of PLCgammaSH2 and Grb2 when PGFN1 treatment is performed after pulling-down of EGFR on surface (Error bars: s.d.).

FIGS. 25a to 25h show the characteristics of PDTX-models (n=3), 25a to 25c are graphs showing MET levels (a), HER2 levels (b), and HER3 levels, compared to the levels of MET, HER2, and HER3 in HCC827 cells (for MET) and SKBR3 cells (for HER2 and HER3) (Error bars: s.d.; n=5), indicating that none of the RTKs is overexpressed, 25d is an image showing immunohistochemical staining (IHC) results of EGFR measured representatively in 5 SQCC PDTX models, wherein the expression of EGFR was determined by calculating EGFR H-score by a magnification rule, 25e is a scatter diagram showing the correlation between EGFR level measured by single-molecule immunolabeling and EGFR H-score, indicating that the IHC H-score shows complete linear correlation with total EGFR expression level measured by single-molecule immunolabeling, 25f and 25g are scatter diagrams showing the correlation between tumor growth inhibition and EGFR level (g) and PPI sum (h) in SQCC PDTX models, 25h shows Immunoblot analysis results of PDTX-S2 treated with vehicle or gefitinib, wherein after treatment with gefitinib for 15 days, the phosphorylation (pEGFR) of the $1068^{th}$ residue, tyrosine, of EGFR (pEGFR) is completely removed (disappeared) and phosphorylation of AKT and S6K (pAkt and pS6K) is also inhibited by gefitinib, indicating that the tumor growth inhibitory effect in PDTX-S2 model is obtained by inhibiting the EGFR/AKT/mTOR/S6K signaling pathway by gefitinib treatment.

FIGS. 26a and 26b show the effects of gefitinib treatment on PDTX-S1 and PDTX-S2 models, wherein 26a is a graph showing changes in EGFR level when treated with gefitinib for 15 days (Error bars: s.d.; n=5), 26b is a graph showing the inhibition degree of EGFR PPI by gefitinib treatment, wherein EGFR PPI complex count in A549 cell is used as a negative control (Error bars: s.d.; n=5).

FIG. 27 is a perspective view schematically illustrating a multi-well according to an embodiment.

FIG. 28 is a diagram showing the multi-well turned upside down.

FIGS. 29 and 30 show processes of manufacturing the multi-well.

FIG. 31 is a graph showing GFP counts in the multi-wells manufactured by an example and a comparative example, respectively (Y-axis: GFP counts).

FIGS. 32 and 33 are graphs showing GFP counts in the multi-wells in multi-well A of an embodiment (FIG. 32) and multi-well B of a comparative example (FIG. 33), in which no antibody is immobilized.

FIG. 34 is a graph showing GFP counts in multi-well A of an embodiment depending on immobilization of an antibody on the well.

FIG. 35 is a graph showing GFP counts in multi-well A of an embodiment according to amount of cell sample.

FIGS. 36 and 37 are graphs showing GFP counts in multi-well A of an embodiment depending on immobilization of an antibody on the well.

FIG. 38 illustrates numbered multi-well A of an embodiment.

MODE FOR INVENTION

A better understanding of the present invention may be obtained through the following examples which are set forth to illustrate, but are not to be construed as limiting the present invention.

Example 1: Preparation of First Protein (EGFR, MET, HER2, and HER3)

EGFR, MET, HER2, and HER3 were selected as first proteins. From lysates resulting from the lysis of cell lines (e.g., cancer cell lines) containing the proteins, the first proteins were obtained. This process will be explained in detail below:

1.1. Cell Lysate Preparation 1.1.1. Cell Line Preparation

A cell line was seeded in an amount of $2 \times 10^6$ cells and cultured in a medium (RPMI1640, high glucose (Thermo 11965-092)). When reaching 90% confluency or higher in a 100-pi culture dish, the cells were collected and aliquoted into two 1.5 ml tubes. After centrifugation (5 min×15,000 g), the culture medium was discarded and the cell pellets were frozen at −80° C. for storage.

Cell lines prepared are listed in Table 1, below:

TABLE 1

|  | Cell Line | Source/Accession number |
|---|---|---|
| Lung Cancer Cell Line | PC9 | CVCL_B260 |
|  | HCC4006 | ATCC, CRL-2871 |
|  | HCC827 | ATCC, CRL-2868 |
|  | H1650 | ATCC, CRL-5883 |
|  | HCC4006-ER | CVCL_S746 |
|  | HCC827-GR5 | CVCL_V622 |
|  | H1666 | ATCC, CRL-5885 |
|  | H2291 | ATCC, CRL-5939 |
|  | A549 | ATCC, CCL-185 |
|  | H358 | ATCC, CRL-5807 |
|  | YU-105 | Yonsei University, derived from patient |
|  | HCC827-GR13 | Yonsei University |
|  | PC9-GR | CVCL_S706 |
|  | YU-101 | Yonsei University, derived from patient |
|  | H1975 | ATCC, CRL-5908 |
| Breast Cancer Cell Line | SKBR3 | ATCC, HTB-30 |
|  | BT474 | ATCC, HTB-20 |
|  | HCC1419 | ATCC, CRL-2326 |
|  | HCC2218 | ATCC, CRL-2343 |
|  | MDA-MB-453 | ATCC, HTB-131 |
|  | HCC1954 | ATCC, CCRL-2338 |
|  | SKBR3-HR | Seoul National University Hospital |
|  | SKBR3-LR | Seoul National University Hospital |
|  | MCF7 | ATCC, HTB-22 |
|  | T47D | ATCC, HTB-133 |
|  | MDA-MB-231 | ATCC, HTB-26 |

1.1.2. Cell Lysate Preparation

A cell lysis buffer was prepared to have the composition of 50 mM Tris-HCl (pH 7.4), 1% (v/v) Triton X-100, 150 mM NaCl, 1 mM EDTA, 10% (v/v) glycerol, protease inhibitor cocktail (Sigma, P8340) 100×, and tyrosine phosphatase inhibitor cocktail (Sigma, P5726) 100×.

The cell aggregates of the cell line sample prepared in Example 1.1.1 were broken up by pipetting. The prepared cell lysis buffer was added in an amount of 200 μl per tube to the pipetted cell line sample. The sample was then stored for 30 min in a cold block (0-4° C.) on ice for a reaction during which the cells were physically mixed by pipetting at regular intervals of 10 min to incite the surfactants to perform cell lysis.

After 30 min of the cell lysis reaction, centrifugation was conducted (10 min, 15,000 g, 4° C.). Then, the pellet was discarded and the supernatant was filtered through a membrane having pores with a size of 0.2 µm. The filtrate was transferred into a new tube and stored until a subsequent experiment.

The cell lysate was found to have a total protein concentration of about 5-10 mg/ml as measured by a total protein quantitation method (Bradford, BCA, DC protein assay, etc.).

1.2. Tissue Lysate Preparation 1.2.1. Construction of Patient-Derived Tumor Xenograft Model A lung squamous cell carcinoma (SQCC) patient-derived tumor xenograft was granted from a Yonsei University research team. Patient-derived tumor xenografts (PDTXs) were constructed. In brief, female severe combined immunodeficient mice (NOG) and nude mice (nu/nu mice; Orient Bio), both 6 to 8 weeks old, were prepared. All animal experiments were conducted according to the guidelines set forth by the Institutional Animal Care and Use Committee (IACUC). A clinical tumor sample derived from a patient was cut into a fragment of 3 mm or less in size and subcutaneously implanted to the flank of each of the prepared NOG mice. Tumor growth rates in the subcutaneous tissue were obtained by measuring tumor sizes twice a week with calipers. When grown to have a diameter of about 1.5 cm, the tumor tissue was excised and sectioned into small fragments (hexahedra with each side about 5 mm long). The sectioned tissue was reimplanted into different mice to sequentially acquire individuals subsequently developing tumors. The mice that retained the patient-derived tumor were designated F0 and the mice subsequently developing tumors derived from F0 were designated FI, F2, F3, F4, and the like, sequentially. A vehicle (PBS) or gefitinib was administered to mice having the $3^{rd}$-generation subsequent tumor (F3) before use in experiments. Intraperitoneal injection of gefitinib or a vehicle at a dose of 50 mg/kg into the prepared PDTXs was performed once a day. Fifteen days after gefitinib injection, tumor tissues were collected from the PDTXs and monitored for PPI and expression level change.

1.2.2. Tissue Lysate Preparation

The tumor tissue obtained in Example 1.2.1. was prepared in an amount of about 20 mm$^3$. A greater volume may be acceptable.

The lysis buffer prepared in Example 1.1.2 was added in an amount of about 300 µl per 20 mm$^3$ of the prepared tumor tissue and subjected to a reaction for one hour in a 4° C. refrigerator while rotating. In this regard, the tissue was cut as finely as possible with operating scissors to realize a large surface area per volume, thereby maximizing the efficiency of the chemical reaction with the surfactant in the lysis buffer.

After one hour of the reaction described above, centrifugation was conducted (10 min, 15,000 g, 4° C.). Thereafter, the precipitate (pellet) was discarded and the supernatant was filtered through a membrane having pores with a size of 0.2 µm. The filtrate was transferred into a new tube and stored until a subsequent experiment.

The tissue was found to have a total protein concentration of about 5-10 mg/ml as measured by a total protein quantitation method (Bradford, BCA, DC protein assay, etc.).

Example 2: Preparation of Second Protein

In this Example, illustration is made of a process of preparing a second protein that is in the form of a fluorescent-protein-attached protein downstream of the first protein prepared in Example 1.

The second proteins illustrated in this Example are summarized in Table 2, below.

TABLE 2

| Protein | Accession number | Marker | Expression vector (Source) |
|---|---|---|---|
| PLC-gamma-SH2 | A nucleic acid molecule coding for a sequence of amino acids 545-765 on PLCg (NM_013187.1) or a sequence of amino acids 540-765 on NP_002651.2 was cloned. | eGFP | pEGFP-N1 or pEGFP-C1 vector (Clontech) |
| Grb2 | A nucleic acid molecule coding for a full a. a. sequence of Grb2 (NP_002077.1) or an a. a. sequence of SH2 (57-155), SH3-SH2 (1-154), or SH2-SH3 (57-217) was cloned | | |
| P85-alpha | A nucleic acid sequence coding for a full a. a. sequence of human p85a (NP_852664.1) or an a. a. sequence of N-SH2 (333-428), C-SH2 (624-718), or tandem SH2 (333-718) or for a full a. a. sequence of mouse p85a (P26450) or an a. a. sequence of N-SH2 (333-428), C-SH2 (624-718), or tandem SH2 (333-718) was cloned | | |

For preparing the second proteins, HEK293 cell line (ATCC) and HeLa cell line (ATCC), both of which express low levels of the first proteins prepared in Example 1, were obtained.

An expression vector for each of the second proteins listed in Table 2 was introduced into the prepared HEK293 cells or HeLa cells, which were then cultured to express the second proteins. After cultivation for 24 hours, the cells were harvested and aliquoted in appropriate amounts for storage at −80° C.

To the cells, a lysis buffer (50 mM Tris-HCl (pH 7.4), 1% Triton X-100, 150 mM NaCl, 1 mM EDTA, 10% glycerol, protease inhibitor cocktail (Sigma, P8340) 100×, tyrosine phosphatase inhibitor cocktail (Sigma, P5726) 100×) was added. To begin with, the lysis buffer was added in an amount of 60 µl to 5×10$^5$ cells because a high concentration of the surfactant (Triton X-100) might interfere with interaction between proteins.

Cell aggregates in the reaction mixture thus obtained were broken up by pipetting, and the detached cells were then stored for 30 min in a cold block (0-4° C.) on ice for a reaction during which the cells were physically mixed by pipetting at regular intervals of 10 min to incite the surfactant to do cell lysis.

After 30 min of the cell lysis reaction, centrifugation was conducted (10 min, 15,000 g, 4° C.). Then, the precipitate (pellet) was discarded and the supernatant was transferred into a new tube and stored until a subsequent experiment.

To 140 µl of PBS, 60 µl of the obtained aqueous solution was added. As a result, a solution of the second protein containing 0.3% Triton X-100 could be obtained. Concentrations of the fluorescent protein attached to the second protein were measured using a fluorimeter. As a result, three kinds of the second proteins were found to range in concentration from 400 to 1000 nM.

Example 3: Preparation of Substrate

A coverslip was immersed in a 1 M KOH solution and then washed in a sonicator (20-30 min). Thereafter, the coverslip was washed well with deionized water and then with a piranha solution (sulfuric acid: hydrogen peroxide=2: 1-3:1 (v/v)). The washed coverslip was coated sequentially with aminopropyl silane and PEG.

After reaction for two hours, the coverslip was washed with deionized water and stored at 20° C. in such a way that the PEG-coated surface was not in contact with any matter until use.

Simultaneously, a channel-type quartz substrate or a well-type acryl substrate was prepared. For the quartz substrate, washing and PEG coating processes were carried out with reference to the aforementioned procedure for the coverslip.

After being constructed, the acryl substrate was immersed in deionized water and washed by sonication. The washed acryl substrate was immersed in a 5% BSA solution, reacted for two hours to prevent nonspecific protein adsorption, and then stored at −20° C. until use.

In the following test, the prepared coverslip and acryl substrate were used. The coverslip and the acryl substrate were thawed and assembled before testing. Alternatively, after PEG coating, the coverslip and the acrylate substrate were assembled and stored in an assembled form at −20° C. until use. Immediately before use, the assembly was thawed.

Example 4: Imaging of Protein-Protein Interaction Between $1^{st}$ and $2^{nd}$ Protein To the prepared substrate, the avidin-lineage protein Neutravidin (Thermo, A2666) was fed at a concentration of 0.1 mg/ml. After 5 min of reaction at room temperature, the substrate was washed twice with 30 μl of PBS buffer.

An antibody against the first protein to be targeted was added to the prepared substrate. In this context, the antibody was in a biotinylated form. The concentration of the antibody was suitably controlled according to antigen-antibody affinity (dissociation constant, KD). In this Experimental Example, the antibody was used at a concentration of 2 ug/ml, with a reaction time of 5 min given thereto. In the case where an antibody was not conjugated with biotin, a secondary antibody might be used to attach the anti-first-protein antibody to the substrate.

The anti-first-protein antibodies used are summarized in Table 3, below.

TABLE 3

| First protein | Antibody | Source |
|---|---|---|
| EGER | anti-EGFR antibody | MS-378-B0, Thermo |
| MET | anti-MET antibody | Ab89297, abcam |
| HER2 | anti-HER2 antibody | OP39, Calbiochem |
| HER3 | anti-HER3 antibody | 66201, R&D systems |

The antibody-treated substrate was washed twice with 30 μl of PBS buffer. To the prepared substrate was added the cell lysate solution or tissue lysate solution containing the first protein prepared in Example 1. The reaction time was set to 15 min because an antigen-antibody reaction might increase for 15 min, but might decrease in efficiency over time after 15 min.

After the reaction, the substrate was washed with a PBS buffer containing 0.05% (v/v) Tween 20. The 0.05% Tween 20 helps prevent hydrophobic regions of membrane proteins from collapsing as well as reducing nonspecific binding.

Subsequently, the second protein lysate solution obtained in Example 2 was added to the substrate. The concentration of the second protein in the first protein lysate solution was set to 1-50 nM (about 30 nM) on the basis of the fluorescent protein. A second protein concentration of 100 nM or higher increases background noise in a florescence microscope, acting as a hindrance to the measurement of accurate fluorescent signals.

The substrate was fixed on and imaged by a fluorescence microscope to obtain data for the first protein/second protein, respectively.

Example 5: Protein Complex (PPI Complex) Analysis

A PPI complex was analyzed on the basis of the toolkit provided by the MATLAB program (MathWorks).

The fluorescent images obtained in Example 4 was stored in a 16-bit unsigned integer format. Fluorescent signals came from eGFP (enhanced green fluorescent protein). For use in observing the signals, a laser was given a wavelength of 488 nm. The laser power was adjusted to 2 mW to maintain the luminescence of eGFP for about 11 sec. Of the entire frames (30 frames), early and middle frames were discarded, and an average of the images of three frames ($22^{nd}$-$25^{th}$ frames) was taken to generate one image. This process was repeatedly conducted at various positions within a well to acquire a total of five images with which the following procedures were then performed. The first about 20 frames were discarded in order to select a section where unnecessary signals (autofluorescence) generated from the null surface of the substrate disappears, and eGFP signals are maintained. Such a selected section may vary depending on imaging condition/established equipment state. In this Example, an EMCCD (Electron-multiplying charge-coupled device; Andor iXon Ultra 897 EX2 (DU-897U-CS0-EXF)) camera was used to obtain fluorescence images with an exposure time of 0.1 per frame and an EMCCD gain value of 40.

In order to remove noises, the following procedure was conducted for each frame:

(a) A start is made from the upper left. One frame was composed of 512×512 pixels. A median value was obtained from 11×11 pixels in the region of a distance of 11 pixels in the right direction from the reference pixel by a distance of 11 pixels in the left direction from the reference pixel. This median value was subtracted from the value of the reference pixel [(Intensity_pixel)−(medianIntensity_11×11neighborhood)]. This procedure was conducted for every 512×512-pixel region. Through median filtering, pepper & salt noise was removed.

(b) The processed image was made smooth by Gaussian smoothing at sigma=0.7, size=5×5.

(c) A threshold was set. Thereby, a pixel value less than a threshold is increased to the threshold value (using an algorithm of searching for local maxima in MATLAB toolkit). Through this process, the local maxima that were not created by fluorescent signals can be removed from the image. A threshold value of 70 was used in the imaging condition of this Example.

Signals from a fluorescent protein are detected as a localized point spread function (PSF). A number of PSF (physical value) is a PPI complex score between the first protein and the second protein to be measured (biological value). The PSF value was converted into a PPI complex score, which is a biological value, via the following procedures:

(a) Positions of local maxima were obtained (for example, $i^{th}$ row, $j^{th}$ column pixel). As described above, single-molecule fluorescence signals are localized and formed at a particular position (about 5×5 pixel size, 1 pixel=0.167 micrometers, under the current observation equipment). Hence, the discovery of local maxima allows the selection of individual PSF. This can be obtained using a toolkit provided by MATLAB.

(b) A process of determining whether or not the local maxima obtained in (a) were actually generated from PSF was performed. To begin with, a minimum intensity value of the local maxima was defined. Analysis was conducted only in the case where the local maxima obtained above were greater than the minimum intensity value. The minimum intensity value used in this Example was 75, and may vary depending on laser power/exposure time/established equipment state. Information of 5×5 pixels based on the finally obtained local maximum coordinates was retrieved and the centroid of intensity was determined in the 5×5 pixels. Here, if the obtained centroid of intensity deviated by 0.5 pixels or greater from the existing local maximum coordinate (if 2D symmetry for the PSF pattern disappeared), the fluorescent signal was determined to be abnormal and excluded from analysis.

(c) Only the PSF that passed all test conditions were selected for determination of the coordinates and the total number. Herein, the total number of PSF obtained are the number of the PPI complex.

Every file photographed under the same condition was subjected to the above procedure to obtain numbers of PSF which were then aggregated and used to calculate a mean and standard deviation. This value finally represents the number of PPI complex in a particular condition (expressed as "Number of single PPI complexes" in the drawing).

Example 6: Determination of PPI Strength, PPI Score, and Activation Score

In the graph where concentrations of the cell lysate (see Example 1.1.2) are set forth on the X axis and PPI complex values measured at concentrations of the cell lysate (see Example 5) are set forth on the Y axis, the slope, that is, [(PPI complex)/(number of PPI complex per unit concentration of cell lysate (1 µg/ml))] was defined as PPI strength (or PPI slope) between the first and the second protein in the cell. All PPI strengths obtained for each cell line were summed. The sum of PPI strengths was defined as a PPI score for the cell line. The sum of PPI strengths (or a PPI score) accounts for a total of PPI of the first protein and the second protein tested at a unit concentration of cell lysate of each cell line.

The sum of PPI strengths can be calculated according to the following equation:

$$\text{Sum of } PPI_{cancer\ cell}^{1st\ protein} = \sum_{k=2nd\ protein} (PPI\ \text{strength})_k^{1st\ protein}$$

($1^{st}$ protein: RTK (EGFR, MET, HER2, or HER3 for lung cancer; and HER2 and HER3 for breast cancer);

($2^{nd}$ protein: downstream protein (PLC-gamma-SH2, Grb2, p85-alpha)).

In order to express relative PPI scores among cell lines, the PPI score of a particular cell line (hereinafter referred to as "reference cell line"; PC9 cells among lung cancer cell lines and SKBR3 cells among breast cancer cell lines were used in this Example) was set to 1, on the basis of which PPI scores obtained in other cells (cells other than the reference cell, hereinafter referred to as "test cell") were normalized. In this regard, the value obtained for each cell line was defined as a normalized PPI score for the cell line.

In addition, a total amount of the first protein in each cell lysate (for example, RTK (EGFR, MET, HER2, or HER3) for lung cancer; and HER2 and HER3 for breast cancer) was measured. As the total amount of first protein, a value obtained by dividing a quantitative result from Sandwich ELISA, quantitative western blot, etc. using each antibody (see Table 3) by the weight of the cell lysate (weight of total protein in the cell lysate) was determined.

A value obtained by dividing the PPI score or normalized PPI score by the total amount of the first protein was defined as an activation score. Here, in order to express relative activation scores among cell lines, the activation score of a reference cell line (PC9 cells for lung cancer cell lines and SKBR3 cells for breast cancer cell lines) was set to 1 on the basis of which activation scores obtained in test cell lines were normalized. In this regard, the value obtained for each cell line was defined as a normalized PPI activation for the cell line.

In the case where a PPI score is obtained in a PDTX (patient-derived tumor xenograft) mouse model, a negative background measured may be subtracted from the value obtained in the above-described manner so as to reduce background noise. For the negative background, a normal tissue from the same patient or a cancer cell lysate with a normal EGFR gene may be used. For example, in A549 cells with a normal EGFR gene, interaction between EGFR and each downstream protein is measured to obtain a PPI score. This is set forth as a negative background. A final PPI score is calculated by subtracting the negative background from the PPI score obtained in each PDTX mouse model.

Example 7: Heatmap Construction

In addition to the digitalization of data in Example 5, a heatmap was constructed to give supplemental data for analytical decision. The heatmap is an option for representing data, but is not intended to limit the analysis of data.

Of X and Y axes, one is given to second proteins (downstream proteins) while the other is for kinds of cell lines to create a 3×16 lattice structure (number of second proteins (a total of 3: see Table 2 (p85-alpha, Grb2, and PLC-gamma-SH2))×number of cell lines (a total of 15 (lung cancer cell lines) or a total of 11 (breast cancer cell lines): see Table 1)). This lattice structure was created for each first protein (four lattice structures (EGFR, MET, HER2, and HER3; lung cancer), or two lattice structure (HER2 and HER3; breast cancer) (for HER3, only p85-alpha was used as a second protein). Then, color and brightness were determined for each lattice according to the PPI strength obtained between the first protein and the second protein in corresponding cells to construct a heatmap (for example, a deep black color, a moderately bright red color, and a bright green color may be given in increasing order of PPI strength, but the color and brightness may not be standardized, but arbitrarily determined via tests by a researcher). Regardless of which cell is set forth as a reference, the relative difference between cell lines is not changed.

Example 8: Drug Responsiveness and Correlation Between PPI Score and Activation Score With reference to the drawing, the test results in Examples 1 to 7 are explained as follows:

FIG. 1 is a schematic view of a method for measuring single-molecule protein interaction. The left panel schematically illustrates that neutravidin, an anti-RTK antibody, and a cell or tissue lysate to be analyzed are added in that order to a polyethylene glycol-coated substrate and then washed, through which an RTK protein target is fixed to the substrate, as shown in the middle panel. In the right panel, there is a representation that a fluorescence-labeled interacting protein is added, followed by observing and quantitating a fluorescent signal to measure the level of single-molecule protein interaction.

FIG. 2 gives graphs showing identification results of target proteins (first proteins) immobilized on substrates. Assays were conducted with reference to the methods described in Examples 4 and 5. EGF treatment was performed in an amount of 100 ng/μl for 3 min. The left graph of FIG. 2 shows a result after EGFR in H1666 cells was immobilized on a substrate via an antibody (MA5-13266, ThermoFisher) against an extracellular domain of EGFR and the immobilization was identified with an antibody (#4267, Cell signaling technology) against a cytoplasmic domain of EFGR while the middle graph of FIG. 2 gives a result after an antibody against HER2 was added to identify whether or not EGFR formed a dimer with HER2. In the right graph of FIG. 2, there is a result after an antibody against Shc1 was added to identify whether EGFR formed a dimer with Shc1.

According to the addition of an antibody to a substrate, the target RTK protein (first protein) is (expressed as +) or is not (expressed as −) immobilized on the substrate. Through the results, suitable antibodies can be selected to attach various target proteins to a substrate. Further, it was identified that not only single target proteins, but also protein conjugates existing in the body, like EGFR-HER2 or EGFR-Shc1, can be immobilized on a substrate.

FIG. 3 gives images showing protein interaction after a fluorescence-labeled interacting protein (second protein) was added to a first-protein-immobilized substrate. The PPI complex observed as described in Example 5 is represented as a localized point spread function (PSF) and was selected using a computer algorithm. A fluorescent signal was observed only after a downstream protein was added. Green circles represent observed PPI complexes.

FIG. 4 is a graph in which the amounts of PPI complexes observed in FIG. 3 were quantified. When a downstream protein (second protein) is added (PLCgammaSH2, Grb2, and p85-alpha on x axis), a high level of PPI complex was selectively observed. In contrast, a low level of signals was observed in the absence of an antibody against the target RTK protein (EGFR) (black bar) or a downstream protein (buffer on X axis). The signal observed in both cases can be understood to be background noise.

FIG. 5 shows graphs in which the number of PPI complexes increases with increasing amount of cell lysate. It is observed that the amount of PPI complexes (Y axis) linearly increases as the amount of the cell lysate including a target RTK protein (first protein: EGFR) increases (X axis). This analysis allows quantitative comparison of PPI complexes between samples in a given amount of a particular cell lysate.

FIG. 6 is a schematic view illustrating a process of quantitating a first protein by single-molecule sandwich ELISA. The process of attaching a target RTK protein (first protein) to a substrate is the same as in FIG. 1. Instead of a fluorescence-labeled downstream protein (second protein), a second antibody recognizing the target RTK protein may be added to quantitate the target RTK protein. Here, the RTK protein should have the second antibody (detection antibody) and should have respective different antibody-recognizing sites (epitopes) for the first antibody (pull-down antibody) used to immobilize the RTK protein to the substrate and for the second antibody. From a fluorescence-labeled antibody recognizing the second antibody, the amount of the RTK protein immobilized on the surface can be measured using a single-molecule technique (see Example 5).

FIG. 7 is a graph showing a specificity result obtained through single-molecule sandwich ELISA. It was observed that the absence of even one of the components shown in the schematic view of FIG. 6 resulted in poor single-molecule sandwich ELISA signal results.

FIG. 8 gives graphs showing changes in the number of PPI complexes according to kinds (red ① vs. sky blue ③) and states (red ① vs. black ②) of cell lines. It was observed that the activation of a target RTK protein (first protein; EGFR) existing in cells by a corresponding ligand (EGF+) resulted in a higher level of PPI complexes at the same amount than otherwise. In addition, the presence of an activity mutation in the target RTK (PC9, sky blue) was observed to increase the number of PPI complexes with the target RTK.

FIG. 9 gives graphs showing changes in the number of PPI complexes per unit concentration of a sample (PPI slope) according to various target RTKs (first proteins). A change in the number of PPI complexes between ligand stimulation (gray) and non-stimulation (black) of the target proteins (first proteins) EGFR, MET, HER2, and HER3 was quantitatively measured using the single-molecule co-IP technique described in Example 6. Based on the result, the activity of target RTK can be measured through PPI complex quantitation.

FIG. 10 gives graphs showing changes in the number of PPI complexes according to EGFR mutation states and the ratios of activated EGFR per cell, calculated on the basis of the changes. The upper graph shows interaction results between EGFR and downstream proteins according to individual cell lines as analyzed by the PPI complex measurement method and the lower graph shows quantitated levels of activated EGFR per cell (absolute occupancy (%)) that are obtained by measuring an expression level of EGFR per cell using single-molecule sandwich ELISA (see FIG. 6) and dividing the expression level by the interaction result.

FIG. 11 is a graph showing absolute occupancy (%) obtained by applying the same method as for EGFR in FIG. 10 to HER2 and HER3. Very poor activity was detected for HER2 whereas HER3 shows very high activity.

FIG. 12 is a heatmap showing interaction (signal strength) between EGFR, MET, HER2, and HER3 (first proteins) and proteins downstream thereof (second proteins) for lung cancer cell lines (Example 7). Color indicators for signal strength are given below the heatmaps.

FIG. 13 is a graph showing a sum of quantified values of respective signal strengths between EGFR (first protein) and three different second proteins out of the results of FIG. 12 (left and middle) and responsiveness of individual cell lines to the EGFR-targeted anticancer agent AZD9291 (osimertinib) (IC50; a concentration at which cell viability decreases by 50%, compared to no treatment).

Bar colors account for the groups divided according to EGFR gene mutations at the right side. The activation scores were found to have more significant correlation with drug responsiveness (IC50) than the PPI scores (the higher the activation score, the lower the IC50 value (higher drug responsiveness)).

FIG. 14 is a graph showing correlation between responsiveness (Y axis) and activation scores of an EGFR-targeted anticancer agent (AZD9291) (left) and a variety of responsiveness of the targeted anticancer agent according to gene types (right). In this graph, it is observed that the activation scores exhibit high correlation (r=0.85) with the responsiveness of AZD9291 and although the genes are the same type, different responsiveness may be obtained by conventional EGFR genetic assays.

FIG. 15 is a heatmap showing signal strength (interaction) between HER2 and HER3 (first proteins) and downstream proteins (second proteins) in breast cancer cell lines (Example 7).

FIG. 16 is a graph showing expression levels of HER2 (upper) and HER3 (middle), which are the biomarkers conventionally used to predict the responsiveness of the anticancer agent trastuzumab in breast cancer cell lines and degrees of the trastuzumab-induced cell growth inhibition (lower).

FIG. 17 gives graphs showing correlations between PPI scores measured using HER2 or HER3 signals and trastuzumab responsiveness (log GI50). PPI scores (r=0.91) are found to have higher correlation with trastuzumab responsiveness, compared to expression levels of the conventional biomarkers HER2 (r=0.54) and pHER2 (r=0.44) (lower graphs).

FIG. 18 is a heatmap showing PPI complex signals between EGFR, MET, HER2, and HER3 and three different downstream proteins thereof, as measured in tissue lysates from PDTX mouse models (Example 1.2) (n=5; expressed as PDTX-1, -2, -3, -4, and -5).

FIG. 19 gives graphs showing expression levels of EGFR in tissue lysates obtained from PDTX mouse models (Example 1.2) (upper) and activation scores calculated using the expression levels of EGFR (results of FIG. 18) (lower).

FIG. 20 gives graphs showing changes of tumor size in gefitinib (50 mg/kg)-injected PDTX mouse models (Example 1.2.1) in comparison with results in vehicle (PBS)-administered groups. For PDTX-2, although the expression level of EGFR was low, a high activation score was detected (see FIG. 19) and an excellent anti-tumor effect was obtained (see FIG. 20). These results indicate that the activation scores (that is, activated EGFR ratios) are in closer correlation with drug responsiveness than EGFR expression levels.

FIG. 21 is a graph showing correlation between degrees of gefitinib-induced tumor growth inhibition and EGFR activation scores in PDTX mouse models (Example 1.2.1). As described above, it was observed that there was significant correlation (r=0.96) between degrees of gefitinib-induced tumor growth inhibition and EGFR activation scores.

FIG. 22 is a graph showing numbers of EGFR PPI complexes per unit concentration of each of tissue lysate samples obtained from PDTX mouse models (Example 1.2.1) before and after gefitinib (50 mg/kg) injection. Significantly reduced numbers of EGFR PPI complexes were counted in the tissues after gefitinib injection, indicating that gefitinib induces EGFR signaling suppression.

Example 9

9.1. Preparation of Antibody and Reagent

In order to pull down respective proteins, the following antibodies were employed: anti-EGFR antibody (MS-378-B0 ThermoFisher), anti-MET antibody (ab89297 Abcam), anti-HER2 antibody (BMS120BT ThermoFisher), anti-HER3 antibody (BAM348 R&D systems) mCherry (ab34771 Abcam), and anti-KRas antibody (sc-521 Santa Cruz).

As respective detection antibodies for corresponding proteins and PTMs (post-translational modifications), the following antibodies were employed: anti-EGFR antibody (4267 Cell signaling), anti-EGFR (pTyr 1068) antibody (ab32430 Abcam), anti-EGFR (pTyr 1086) antibody (ab32086 Abcam), anti-EGFR (pTyr 1173) antibody (4407 Cell signaling), anti-MET antibody (8494 Cell signaling), anti-HER2 antibody (MA5-15050 ThermoFisher), anti-HER2 (pTyr1221/1222) antibody (2243 Cell signaling), anti-HER3 antibody (ab32121 Abcam), anti-HER3 (pTyr 1289) antibody (Cell signaling technology, cat. No. 4791), anti-Grb2 antibody (ab32037 Abcam), anti-Shc1 antibody (ab33770 Abcam), anti-Shc1 (pTyr 239/240) antibody (ab109455 Abcam), anti-HSP90 antibody (PA3-013 ThermoFisher), anti-MIG6 antibody (11630-1-AP Proteintech), anti-GAPDH antibody (3906 Cell signaling), and anti-c-Cbl antibody (2179 Cell signaling).

Biotinylated anti-mouse immunoglobulin G (IgG) (405303 BioLegend) and Cy3-conjugated anti-rabbit IgG (111-165-046 Jackson ImmunoResearch) antibodies were used as secondary antibodies.

Western blotting was conducted using the following antibodies: anti-EGFR (pTyr 1068) antibody (2234 Cell signaling), anti-EGFR antibody (2232 Cell signaling), anti-Erk (pThr202/Tyr204) antibody (9106 Cell signaling), anti-Erk antibody (4696 Cell signaling), anti-Akt antibody (4060 Cell signaling), anti-Akt antibody (4691 Cell signaling), anti-S6K (pSer235/236) antibody (4858 Cell signaling), anti-S6K antibody (2217 Cell signaling), and anti-actin antibody (ab8227 Abcam).

EGFR was stimulated (3 min) using 100 ng/ml EGF (PHG0311L Life technologies).

Gefitinib (S1025 Selleckchem), osimertinib (S7297 Selleckchem), BKM120 (S2247 Selleckchem), dabrafenib (S2807 Selleckchem), and trastuzumab (A1046 BioVision) were used to measure PPI changes in lung adenocarcinoma cells and HER2-/HER3-PPI in breast cancer cells, cell viability based on MTT assay, and tumor growth in PDTX models.

9.2. Cell Culture

All cell lines were cultured in an RPMI1640 medium (22400-105 Life technologies) supplemented with 10% (w/v) fetal bovine serum (26140-079 Life technologies), 10 μg/ml gentamicin (15710-063 Life technologies), 100 units/ml penicillin, and 100 μg/ml streptomycin (15140-122 Life technologies). PC9-GR (gefitinib-resistant cell line Accession No. CVCL_S706), HCC827-GR5 (gefitinib-resistant cell line Accession No. CVCL_V622), and HCC4006-ER (erlotinib-resistant cell line Accession No. CVCL_S746) cell lines were cultured in the presence of 100 nM gefitinib or erlotinib. All cell lines were cultured at 37° C. in a 5% $CO_2$ atmosphere in a humidified incubator. The cultured cells were washed with cold phosphate buffered saline (PBS). Cells were rapidly collected using 1 ml of cold PBS and a scraper (90020 SPL Life Science). A cell suspension obtained from one petri dish (diameter 100 mm) was divided into 3-4 aliquots. These aliquots were centrifuged at 4° C.

and 3,000×g for 5 min. The supernatant was discarded and the pellet was stored at −80° C. until use.

9.3. Construction of eGFP-Labeled Prey Protein and Transfections

Rat PLCγ$_{SH2}$ cDNA including a tandem SH2 domain (amino acids 542 to 765 of NM_013187.1) was isolated directly from a Rat cDNA library using BglII and EcoRI. cDNAs of Grb2 (human Grb2; Addgene 46442), p85α (mouse p85α Addgene 1399), Shc1 (human Shc1, Addgene 73255), Eat2 (human Eat2, Addgene 46423), APCS (human APCS, Addgene 46477), Nck1 (human Nck1, Addgene 45903), and SOS1 (human SOS1, Addgene 32920) were excised using restriction enzymes corresponding to restriction sites in their respective plasmids. eGFP-tagged CARM1 (human CARM1) and EGFR genes were provided by Seoul National University (Korea) and KAIST (Korea), respectively. All the cDNAs were cloned into pEGFP-C1 (Clontech Laboratories) to construct corresponding eGFP-labeled prey proteins. W36K, R86M, and W193K point mutations were introduced into a Grb2 gene to afford respective Grb2 mutants N*-, SH2*-, and C*-construct. An EGFR mutant was constructed by deleting E746-A750 from an EGFR gene or substituting a lysine at position 858 with arginine on an EGFR gene.

The plasmids obtained above were introduced into HEK293 cells by electroporation using Neon transfection system (MPK5000 Life technologies) according to the manufacturer's instruction. For this, 30 μg of a plasmid DNA was mixed with 100 μl of a HEK293 cell suspension containing about 2×10$^6$ cells. Two 950V electric pulses were applied to the HEK293 cells (with a duration of 35 ms for each pulse). Twenty four hours after transfection, transfected cells were harvested and stored at −80° C.

9.4. Lung Cancer Patient-Derived Tumor Xenograft Model

All animal studies were conducted according to the guidelines set forth by the Institutional Animal Care and Use Committee (IACUC). Female severe combined immunodeficient mice (NOG) and nude mice (nu/nu mice; Orient Bio), both 6 to 8 weeks old, were prepared. A clinical tumor sample (obtained from a lung adenocarcinoma patient or a lung squamous cell carcinoma (SQCC) patient) was cut into a fragment of about 3 mm in size and subcutaneously implanted to the flank of each of the NOG mice. One to four months after the implantation, a tumor was observed in the implanted region. Tumor growth rates in the subcutaneous tissue were obtained by measuring tumor sizes twice a week with calipers. When grown to have a diameter of about 1.5 cm, the tumor tissue was excised and sectioned into small fragments (each 5 mm$^3$ in volume). The sectioned tissue was reimplanted into different mouse groups to acquire subsequent tumors. The mice that retained the patient-derived tumor were designated F0 and subsequent generations having subsequent tumors derived from F0 were designated FI, F2, F3, and the like, sequentially (see FIG. 23A). The 3$^{rd}$ generation mice (F3) were used in treatment with a vehicle (PBS), osimertinib, or gefitinib.

Of the patient-derived tumor xenografts (PDTXs) thus obtained, the mice (F3; n=3) engrafted with the tumor derived from a lung adenocarcinoma patient were designated PDTX-A1, PDTX-A2, and PDTX-A3 and the mice (F3; n=5) engrafted with the tumor derived from a lung SQCC patient were designated with PDTX-S1, PDTX-52, PDTX-S3, PDTX-S4, and PDTX-S5, respectively.

Osimertinib and gefitinib or a vehicle were intraperitoneally injected once a day at respective doses of 5 and 50 mg/kg into the patient-derived tumor xenografts (PDTXs). Fifteen days after drug injection, tumor tissues were excised from the PDTXs and monitored for PPI and expression level change.

9.5. Single-Molecule Co-IP and Immunolabeling Imaging

For a detailed protocol of single-molecule co-IP and immunolabeling imaging, reference was made to "Lee, H. W. et al. Real-time single-molecule coimmunoprecipitation of weak protein-protein interactions. *Nat. Protoc.* 8, 2045-2060, (2013)". NeutrAvidin (10 μl of 0.1 mg/ml; A2666 Life technologies) was put in individual reaction chambers. After 10 min of incubation, uncoupled NeutrAvidin was removed. A miniaturized imaging chamber was immersed in a PBS-filled reservoir and completely washed by shaking 100 times in lateral directions. After complete removal of PBS, biotinylated pull-down antibodies were incubated for 10 min on the NeutrAvidin-coated surface to form a layer. For a MET antibody, a biotinylated secondary antibody (alpha-mouse IgG) was used to recognize the primary antibody. After the chamber was washed with PBS, a cancer cell or tumor tissue extract was applied to the antibody-coated surface. After 15 min, uncoupled extracts were removed and the chamber was immersed in a PBS-filled reservoir supplemented with 0.05% (v/v) Tween 20.

For single-molecule co-IP imaging, a transformed HEK293 cell extract was diluted with a 30 nM eGFP-tagged probe protein and then loaded to an imaging chamber. The chamber was positioned on a TIRF microscope and eGFP florescence was recorded on EMCCD (20 frames; 100-ms exposure).

In the single-molecule immunolabeling imaging, a dye-labeled detection antibody was used instead of the eGFP-labeled probe protein for five frames. To avoid overlap between the detection antibody and the pull-down antibody, selection was made of a detection antibody that has an epitope at a tyrosine residue on a cytoplasmic kinase region or tail. The detection antibody was labeled directly with Alexa488 (MET antibody) or indirectly with a Cy3-labeled secondary antibody (EGFR, HER2, HER3, and pTyr antibody). After recording fluorescence of 5 or 20 frames (0.1 sec exposure) in a TIFF stack, fluorescent spots were counted to measure numbers of single-molecule PPI complexes or immunolabeled proteins. A mean value and standard deviation of single-molecule counts was obtained from 10 different positions within the same reaction chamber.

9.6. PPI Complex and Immunolabeled Protein Counting

TIFF files obtained by fluorescence imaging were analyzed using a custom GUI (written in MATLAB (MATLAB 2016a, MathWorks)). From three frames (17-19 for eGFP9 and 3-5 for Cy3 and Alexa488), local maxima having an intensity representative of single PPI complexes or immunolabeled proteins were identified. For background correction, an image obtained by spatial median-filtering (11×11 pixel) was subtracted from an original image according to frames. The images thus obtained were averaged and subjected to thresholding before use in detecting local maxima (with custom MATLAB GUI).

Example 10: Prediction of Responsiveness of PDTX to EGFR-Targeted Inhibitor 10.1. Prediction of Responsiveness of Lung Adenocarcinoma Xenograft PDTX to Osimertinib It was ascertained that PPI metrics of the HER-family receptors are tightly correlated with the drug responsiveness of cancers and examination was made to determine whether or not single-molecule immunolabeling or co-IP analysis is applicable to the screening of certain cancer that has responsiveness to HER-family receptor-targeted therapy (that is, on which HER-family receptor-targeted therapy shows an anticancer effect). To this end, lung adenocarcinoma patient-derived tumor xenograft mice (PDTXs: PDTX-A1-PDTX-A3 of FIG. 23) were created.

These lung adenocarcinoma PDTXs were observed to have activation mutation in the EGFR gene (exon 19 or L858R mutation).

After 30 days of treatment of the lung adenocarcinoma PDTXs (PDTX-A1-PDTX-A3; 3 or more mice each, the following results are represented by average values) with osimertinib (5 mg per 1 kg of weight daily), tumor sizes were measured and compared with a control (vehicle administered). The results are depicted in the left panels of FIG. 23b. As is understood from data of the left panels of FIG. 23b, PDTX-A1-PDTX-A3 showed a significant reduction of tumor size by treatment with osimertinib (A1>A2>A3).

In addition, PPI complexes between each of EGFR, HER2, HER3, and MET receptors and each of the downstream proteins PLCgammaSH2, Grb2, and p85-alpha in each PDTX (PDTX-A1-PDTX-A3) were counted, and the results are depicted in the left panels of FIG. 23c (expressed as PPI count in FIG. 23c). As shown in FIG. 23c, PPI complex counts between EGFR and three different downstream proteins were in the order of A1>A2>A3, coinciding with the behavior of tumor size reduction by treatment with the EGFR inhibitor, osimertinib. This result indicates that PPI complex counts between a target protein and a downstream protein in lung adenocarcinoma PDTX models exhibit significant correlation with an anticancer effect of a therapeutic agent targeting the target protein.

In addition, expression levels of EGFR and other receptors (MET, HER2, and HER3) in 8 PDTX (A1-A3 and S1-S5) individuals were measured, and the expression level of each of the receptors was normalized to that of a control (EGFR: A549, MET: HCC827-GR5, and HER2 and HER3: SKBR3). The results are depicted in FIGS. 23d and 25a-c.

As shown in FIG. 23c, the PDTX models (A1-A3) did not exhibit significant PPI complex counts for MET, HER2, or HER3 receptors, but exhibited somewhat significant PPI complex counts for EGFR. This result implies that PDTXs exhibit oncogene addiction to EGFR signaling at protein and PPI levels.

Next, as proven by normalized PPI counts (numbers of PPI complexes per unit concentration of first protein; corresponding to activation scores) in lung adenocarcinoma cell lines, examination was made to determine whether the responsiveness of PDTX to osimertinib therapy can be predicted. In each of the PDTX models (A1-A3) treated for 30 days with osimertinib (5 mg per kg of weight daily), tumor growth inhibition rates (tumor growth inhibition (%)=[($\Delta V_{vehicle}-\Delta V_{gefitinib}$)/|$\Delta V_{vehicle}$|]×100; $\Delta V_{vehicle}$: difference in tumor volume between post- and pre-treatment with a vehicle; $\Delta V_{gefitinib}$: difference in tumor volume between post- and pre-treatment with gefitinib) on the Y-axis were plotted versus PPI sum/EGFR levels (PPI sum: PPI score, PPI sum/EGFR level: Activation score) on the X-axis, and the results are depicted in FIG. 23e. As can be seen in FIG. 23e, normalized PPI counts (PPI sum/EGFR level; activation score) were observed to have high correlation with the tumor growth inhibition of osimertinib (r=1).

10.2. Prediction of Responsiveness to Osimertinib in Lung Squamous Cell Carcinoma (SQCC) Xenograft PDTX As much as 29% of lung adenocarcinoma cases are related to the sensitizing mutation of EGFR, whereas only 0.5% of lung SQCC cases have a sensitizing mutation. Accordingly, there are currently no suitable biomarkers for EGFR-targeted therapy for lung SQCC.

In this Example, five lung SQCC PDTXs (PDTX-S1-PDTX-S5) were created and subjected to single-molecule immunolabeling and co-IP profiling (Example 9.5). All the five PDTXs (PDTX-S1-PDTX-S5) were found to exhibit minimal levels of MET, HER2, and HER3 receptor proteins and PPI complexes related thereto (the right panels of FIG. 23c and FIGS. 25a-c).

Meanwhile, total EGFR counts (EGFR level) and EGFR PPI complex counts were detected at significant levels (FIGS. 23c and 23d, and FIGS. 25d and 25e).

These results are deemed to result from the fact that lung SQCC often depends on EGFR with respect to proliferation signaling.

10.3. Prediction of Responsiveness to Gefitinib in Lung Squamous Cell Carcinoma (SQCC) in PDTX After 15 days of the treatment of five PDTXs (PDTX-S1-PDTX-S5) with gefitinib, tumor growth inhibition rates were measured and are depicted in the right panels of FIG. 23b. Of PDTX-S1-PDTX-S5, S1 and S2 were identified to show significant tumor inhibition effects. In the various PDTX individuals tested, the PPI complex count normalized to an EGFK level (activation score) was identified again to have very high correlation (Spearman correlation of 0.9) with tumor growth inhibition (FIG. 23f and FIG. 25f-h).

The data obtained above suggest that the normalized PPI count is tightly correlated with the responsiveness of non-small cell lung cancer to an EGFR-targeted inhibitor. To understand that a normalized PPI count other than a sum of PPI counts has high correlation with responsiveness to an anti-tumor drug, two lung SQCC PDTXs (PDTX-S1 and PDTX-S2) which had shown characteristic signaling phenotypes and gefitinib responsiveness were particularly observed.

PPI complex counts were measured in PDTX-S1 and PDTX-S2 before gefitinib treatment and 15 days after gefitinib treatment, and are depicted in FIG. 23g and FIG. 26a-b.

As is understood from the data, PDTX-S1 retained a detectable level of EGFR PPI complex counts particularly with the regulatory p85a subunit of PI3K. In contrast, PDTX-S2 showed EGFK PPI complex counts that were reduced or could not be discriminated, compared with a negative control using A549 cells (FIGS. 23g and 26). Accordingly, the gefitinib dose (50 mg/kg) used in the experiments completely regulated a hyperactive but smaller pool of EGFRs in PDTX-S2 to induce the shrinkage of corresponding cancers. In contrast, the same gefitinib dose could not regulate EGFK activity, but allowed significant EGFK overexpression in PDTX-S1. The results account for the reason why PDTX-S2 with a normalized PPI count exhibits a more outstanding responsiveness to gefitinib than PDTX-S1 with a high EGFK level and total PPI count.

Based on the result that PDTX-S1 shows increased EGFR-p85α interaction, PDTX-S1 was treated with the PI3K inhibitor BKM120 (50 mg/kg) (FIG. 23h).

As is understood from the data, BKM120 exhibited a more potent tumor growth inhibition effect at the same dose (50 mg/kg) than gefitinib. A combination therapy of gefitinib and BKM120 (gefitinib (50 mpk (mg per 1 kg weight)/BKM120 (50 mpk)) elicited tumor shrinkage. This result suggests that the single-molecule co-IP profiling, which employs different downstream proteins to examine PPI, can find useful applications in selecting target signaling pathways and designing a combination therapy strategy of two or more drugs.

10.4. Prediction of Responsiveness in Non-Small Cell Cancer Xenograft PDTX

Normalized PPI complex counts obtained from two kinds of non-small cell lung cancer xenograft models PDTX-A1-A3 and PDTX-S1-S5 were pulled down and compared in single plots (FIG. 23*i*).

Despite a difference in genetic alteration and cancer subtype, the data points exhibit a uniform pattern, making a fair coincidence with the tumor growth inhibition with a Spearman correlation of 0.95.

The data suggests that the normalized PPI complex count can be a gauge of EGFR signal strength and thus can act as an efficacy prediction marker for EGFR-targeted therapies.

Example 11. Single-Molecule Immunolabeling and Co-IP Profiling of Human Patient Sample)

Using a micro-chamber and a high-throughput single-molecule imaging system proposed in the present invention, tumor tissues of human patients were characterized (FIG. 24).

A typical cryogenic lysis protocol developed for PDTX specimens was applied to two lung adenocarcinoma patient tissues surgically excised from lung adenocarcinoma patients (Yonsei University Severance Hospital) (P1 and P2 in FIG. 24*a*).

Briefly, the prepared patient tissues were homogenized (about 0.6 cm) and immersed in liquid nitrogen. After further homogenization, PBS was added for complete dissolution. Centrifugation afforded a pellet which was then incubated at 4° C. in PBS while continuously mixing. After centrifugation, the supernatant was taken.

For each of the lysates obtained respectively from the tissues with a size of 15 mm$^3$ (P1) and 18 mm$^3$ (P2) in the above-mentioned manner, 10 different PPI levels (PPI complex values in P1 and P2 relative to the PPI complex of 1.0 in a positive control) and 10 different protein and PTM (post-translational modifications) levels (expression) were measured (see Immunolabeling of Example 9.5) (FIG. 24*b*). As positive controls, use was made of PC9 cells for EGFR, HCC827 cells for MET, and SKBR3 cells for HER2 and HER3.

Although both the tumor tissues (P1 and P2) had an exon19 mutation (exon19 deletion mutation) in the EGFR gene, only sample P1 showed significant EGFR PPI complex counts (FIGS. 24*b* and *c* and Table 4).

TABLE 4

| | Biopsy type | Deposits date | EGFR genotype | Treatment | Response |
|---|---|---|---|---|---|
| Patient P1 | Surgical resection | 2013 Dec. 27 | Δexon19 | Gefitinib | PR: 2014 Nov. 25~2016 Mar. 28 PD: 2016 Jul. 19 |
| Patient P2 | | 2014 Feb. 11 | | Erlotinib | SD: 2014 Apr. 16~2015 May 15 PD: 2015 May 21 |

(PR = Partial response, PD = Progressive disease)

With respect to other receptors, namely HER receptors and MET receptors, significant PPI counts were observed in neither of the two samples (FIGS. 24*b* and *c*).

Patient P1 maintained a partial response (PR: according to response evaluation criteria in solid tumors (RECIST)) for about 1.5 years before progressive disease (PD) designation, whereas Patient P2 maintained stable disease (SD) for one year before PD designation.

Lastly, PDTX-A1, which showed the highest activity of an EGFR signal, and the mutant EGFR (exon 19 deletion) derived from the human patient sample P1 were subjected to in-vitro dephosphorylation by treatment with PIPN1 (FIG. 24*d*).

After dephosphorylation, the binding of eGFP-labeled PLCgamma$_{SH2}$ and Grb2 to the mutant EGFR complex was measured and the measurements are depicted in FIG. 24*d*. As shown in FIG. 24*d*, the dephosphorylation (+PTPN1) almost completely stopped the binding of PLCgamma$_{SH2}$, which reliess fully on the pTyr-SH2 domain interaction, whereas Grb2 binding counts were maintained even after 50% or higher and 80% or higher dephosphorylation. The data suggests that the pTyr-independent signaling mechanism of mutant EGFR works in practice in the PDTX models and surgical tumors.

Example 12: Test for Effect of Adhesive-Application Modality

A multi-well A in which an adhesive E (UV epoxy) was applied to the outer brim of a contact surface between a receiving part 153 and a substrate 300 (test group) and a multi-well B in which an adhesive (UV epoxy) is applied to the entire contact surface between a receiving part 153 and a substrate 300 (comparative group) were each fabricated and the wells were numbered as shown in FIG. 38:

All the wells were surface treated with biotin, with no antibodies immobilized thereto.

A green fluorescent protein (GFP, Clontech)-tagged Grb2 protein (NP_002077.1) was added in an amount of 30 nM to each well, incubated at room temperature (23-27° C.) for 5-10 min, and washed with a washing solution containing PBS (with 0.05% (v/v) Tween 20). GFP counts left in the wells were measured by imaging to quantitate the Grb2 protein. In this regard, a washing solution containing a low concentration (e.g., about 0.1% (v/v) or less) of a non-ionic surfactant (e.g., Tween20, Triton x-100, etc.) is preferred (hereinafter, the same is applicable to protein quantitation). GFP counts were measured by counting fluorescent spots on fluorescence images obtained using an EMCCD (Electron-multiplying charge-coupled device; Andor iXon Ultra 897 EX2 (DU-897U-CS0-EXF)) camera with an exposure time of 0.1 sec per frame and an EMCCD gain value of 40.

Measurements of the GFP counts are depicted in FIG. 32 (multi-well A) and FIG. 33 (multi-well B). In FIGS. 32 and 33, each # number means the position of a well given the corresponding number.

For multi-well A, as shown in FIG. 32, GFP counts that remained in the wells after washing appeared at low levels similarly over the entire well. In contrast, GFP counts that remained in the wells of the multi-well B after washing were measured to be about 15- to 20-fold greater in some wells (#5, #6, and #7) than the other wells.

Because antibodies were not immobilized to the wells, the GFP that remained in the wells after washing were deemed to be attributed to non-specific binding. Therefore, the results of FIGS. 32 and 33 show that the multi-well A in which an adhesive is applied to the outer brim of the receiving part allows the non-specific binding of proteins at a far lower level than the multi-well B in which an adhesive is applied to the entire contact surface between the receiving part and the substrate. A high non-specific binding level of proteins in the multi-well B results from the fact that a part of the adhesive (epoxy) applied to the entire contact surface between the receiving part and the substrate infiltrates into the through-hole so that the adhesiveness of the epoxy exerts an unintended influence to the protein-protein reaction to induce non-specific binding. On the other hand, the adhesive that is applied to the outer brim of the receiving part in the multi-well A cannot infiltrate into the through-hole or only a very small amount of the adhesive infiltrates into the through-hole. Thus, there are no or very slight effects on the protein-protein interaction, thereby resulting in a very low non-specific binding level of proteins.

In order to further identify the induction of specific protein reactions in the multi-well A, a GFP antibody was not immobilized in three wells #1, #5, and #9, but in the remaining nine wells #2, #3, #4, #6, #7, #8, #10, #11, and #12 the above experiment was conducted again to measure GFP counts.

Measurements of GFP counts obtained above are depicted in FIG. 34. As shown in FIG. 34, GFP counts in the nine wells #2, #3, #4, #6, #7, #8, #10, #11, and #12 where a GFP antibody was not immobilized were remarkably higher than those in the three wells #1, #5, and #9 where a GFP antibody was not immobilized. The result identifies again that specific protein interactions are induced in the multi-well A where the adhesive is applied to the outer brim of the receiving part.

Example 13: Protein-Protein Interaction Measurement

A multi-well A was prepared in the same manner as in Example 12 and an anti-EGFR antibody (MS-378-B0, Thermo) was immobilized to the surface of the multi-well A. To each antibody-immobilized well was added a cell sample that was obtained by lysing a cell line having a high expression level of EGFR (H1666; ATCC, #CRL-5885) in a cell lysis buffer (50 mM Tris-HCl (pH 7.4), 1% (v/v) Triton X-100, 150 mM NaCl, 1 mM EDTA, 10% (v/v) glycerol, protease inhibitor cocktail (Sigma, P8340) 100×, tyrosine phosphatase inhibitor cocktail (Sigma, P5726) 100×), followed by incubation at room temperature (23-27° C.) for 15 mM and then by washing with a washing solution containing PBS (with 0.05% (v/v) Tween 20) to capture EGFR on the well surface. GFP-tagged p85-a protein (NP_852664.1) was added to each well having EGFR captured on the surface thereof before imaging.

GFP counts left in the wells were measured with reference to the method of Example 12 to examine protein-protein interaction between EGFR and p85-a.

GFP counts (mean values of five measurements) are plotted against amounts of the cell sample in FIG. 35. GFP counts (mean values of five measurements) and standard deviations are given in Table 5:

TABLE 5

| Cell sample amount (mg/ml) | GFP count (Mean) | Standard deviation |
|---|---|---|
| 0 | 87.5 | 16.90858 |
| 0.03 | 604.8 | 27.67129 |
| 0.05 | 974.8 | 34.54273 |
| 0.08 | 1348 | 68.6343 |
| 0.1087.5 | 1651.8 | 61.36937 |

As shown in FIG. 35 and Table 5, when the multi-well A was used, protein-protein interactions were explicitly measured to have a linear proportional correlation with cell sample concentrations, and the measurements obtained through repeated experiments were observed to have relatively low levels of standard derivations.

Two multi-wells A were prepared in the same manner as in Example 12. Of the two, one was not coated with a GFP antibody (blank) whereas the other was coated (GRB2-GFP). To each well, 100 pM GFP-GRb2 was added and then signals were measured in the same manner as in Example 1.

The results obtained above are depicted in FIGS. 36 and 37. In the multi-well A, as is understood from the data of FIGS. 36 and 37, almost no signals were detected when the well were not coated an antibody for capturing a target protein (GFP) whereas signals were very well detected with low standard deviations (GRB2-GFP) when the antibody was applied. These results indicate that the use of the multi-well A is almost not accompanied by a false positive result.

The invention claimed is:

1. A method for measuring activation of a signaling pathway in a cell or a tissue, comprising steps (1), (2), (3), (4), and (5), or steps (1), (2), (3), (4-1), (4-2), and (5):
    (1) preparing a substrate having a first protein immobilized thereto by adding a test sample containing the first protein to the substrate;
    (2) adding and reacting the prepared first protein-immobilized substrate with a maker-conjugated second protein;
    (3) measuring a signal from the reactant obtained in step (2);
    (4) measuring a signal value per unit amount of the first protein in the test sample added in step (1) based on the signal measured in step (3);
    (4-1) obtaining a signal value per unit amount of the test sample added in step (1) based on the signal measured in step (3);
    (4-2) obtaining a signal value per unit amount of the first protein contained in the test sample based on the signal value per unit amount of the test sample as measured in step (4-1);
    (5) comparing a result obtained in step (4) or (4-2) with that obtained in a reference sample,
    wherein the test sample is the cell, the tissue, lysate, homogenate, or extract of the cell or the tissue, or a body fluid comprising the cell or the tissue, which are all isolated from a mammalian subject,
    the reference sample comprises a normal cell, a cell having a known activation level of a signaling pathway in which the first protein is involved, or a cell isolated from a subject having a known activation level of a signaling pathway in which the first protein is involved, and
    the first protein is involved in the signaling pathway, and the second protein interacts with the first protein,
    wherein the signal value per unit amount of the first protein of step (4) or (4-2) is a quantitative value of a signal or signal intensity obtained by dividing the signal value measured in step (3) or (4-1) by weight or concentration of the first protein in the test sample added in step (1).

2. The method of claim 1, wherein the marker is at least one selected from the group consisting of a small-molecule compound, a protein, a peptide, and a nucleic acid, all of which generate a signal that can be measured through detection of an enzymatic reaction, fluorescence, luminescence, or radiation.

3. The method of claim 1, wherein the marker in the step (2) is at least one selected from the group consisting of a small-molecule compound, a protein, a peptide, and a nucleic acid, all of which generate fluorescence; and the step (3) of measuring a signal is carried out using a total internal fluorescence microscope, a fluorescence camera, or a combination thereof.

4. The method of claim 3, wherein the fluorescence camera is set to have an exposure time of about 0.001 sec to about 1 sec per frame.

5. The method of claim 1, wherein the first protein and the second protein are each independently at least one selected from proteins involved in the signaling pathway in the cell or tissue, and the second protein is a protein that is located downstream of the first protein in the signaling pathway.

6. The method of claim 5, wherein the first protein is a cell membrane protein.

7. The method of claim 6, wherein the first protein is at least one selected from the group consisting of receptor tyrosine kinases, toll-like receptors, G-protein-coupled receptors (GPCR), transferrin receptors, low-density lipoprotein (LDL) receptors, ROS1; BCR-Abl1 fusion proteins; non-receptor kinases; GTPases; hormone receptors; anti-apoptotic proteins; and immune checkpoint proteins.

8. The method of claim 1, wherein:
the first protein and the second protein are each independently of two or more kinds of proteins involved in the signaling pathway in the cell or tissue, the second protein being located downstream of the first protein in the signaling pathway, and
the value, obtained in step (4) or (4-2), per unit amount of the first protein contained in the test sample is a sum of the values respectively obtained for each of the two or more kinds of the first protein and each of the two or more kinds of the second protein.

9. A method for screening a first protein as a target of a therapy suitable for application to a subject, comprising steps (1), (2), (3), (4), and (5), or steps (1), (2), (3), (4-1), (4-2) and (5):(1) preparing a substrate having a first protein immobilized thereto by adding a test sample containing the first protein to the substrate;
   (2) adding and reacting the prepared first protein-immobilized substrate with a maker-conjugated second protein;
   (3) measuring a signal from the reactant obtained in step (2);
   (4) measuring a signal value per unit amount of the protein in the test sample added in step (1) based on the signal measured in step (3), or
   (4-1) obtaining a signal value per unit amount of the test sample added in step (1) based on the signal measured in step (3); and
   (4-2) obtaining a signal value per unit amount of the first protein contained in the test sample based on the signal value per unit amount of the test sample as measured in step (4-1),
wherein the steps (1), (2), (3), and (4), or steps (1), (2), (3), (4-1), and (4-2) are carried out for each of two or more different first proteins; and
(5) comparing the results obtained in steps (4) or (4-2) for the two or more different first proteins,
wherein the test sample is a cell, a tissue, a cell or tissue lysate, homogenate, or extract, or a body fluid, which are all isolated from the subject, and the first protein is involved in the signaling pathway, and the second protein interacts with the first protein,
wherein the signal value per unit amount of the first protein of step (4) or (4-2) is a quantitative value of a signal or signal intensity obtained by dividing the signal value measured in step (3) or (4-1) by weight or concentration of the first protein in the test sample added in step (1).

\* \* \* \* \*